US009164032B2

(12) United States Patent
Islam

(10) Patent No.: US 9,164,032 B2
(45) Date of Patent: Oct. 20, 2015

(54) SHORT-WAVE INFRARED SUPER-CONTINUUM LASERS FOR DETECTING COUNTERFEIT OR ILLICIT DRUGS AND PHARMACEUTICAL PROCESS CONTROL

(71) Applicant: OMNI MEDSCI, INC., Ann Arbor, MI (US)

(72) Inventor: Mohammed N. Islam, Ann Arbor, MI (US)

(73) Assignee: OMNI MEDSCI, INC., Ann Arbor, MI (US)

( * ) Notice: Subject to any disclaimer, the term of this patent is extended or adjusted under 35 U.S.C. 154(b) by 101 days.

(21) Appl. No.: 14/108,986

(22) Filed: Dec. 17, 2013

(65) Prior Publication Data
US 2014/0183362 A1 Jul. 3, 2014

Related U.S. Application Data

(60) Provisional application No. 61/747,487, filed on Dec. 31, 2012.

(51) Int. Cl.
*G01N 21/35* (2014.01)
*G01N 21/359* (2014.01)
(Continued)

(52) U.S. Cl.
CPC ............ *G01N 21/359* (2013.01); *A61B 5/1455* (2013.01); *G01J 3/453* (2013.01);
(Continued)

(58) Field of Classification Search
CPC .. G01N 21/35; A61B 5/0075; A61B 5/14556; H01S 3/302
USPC ...................................................... 250/338.4
See application file for complete search history.

(56) References Cited

U.S. PATENT DOCUMENTS

| 4,063,106 A | 12/1977 | Ashkin et al. |
| 4,158,750 A | 6/1979 | Sakoe et al. |

(Continued)

FOREIGN PATENT DOCUMENTS

| EP | 1148666 | 10/2001 |
| WO | WO9715240 | 5/1997 |

(Continued)

OTHER PUBLICATIONS

"Application Brief AB-070: The role of infrared microprobe analysis in forensic drug analysis," www.smithsdetection.com, Jun. 27, 2005.
(Continued)

*Primary Examiner* — David Porta
*Assistant Examiner* — Abra Fein
(74) *Attorney, Agent, or Firm* — Brooks Kushman P.C.

(57) ABSTRACT

A system and method for using near-infrared or short-wave infrared (SWIR) light sources for identification of counterfeit drugs may perform spectroscopy using a super-continuum laser to provide detection in a non-contact and non-destructive manner at stand-off or remote distances with minimal sample preparation. Also, near-infrared or SWIR light may penetrate through plastic containers and packaging, permitting on-line inspection and rapid scanning. The near-infrared or SWIR spectroscopy may also be used to detect illicit drugs and their chemical composition. Moreover, the spectroscopic techniques may also be applied to quality assessment and control in pharmaceutical manufacturing, thus permitting the implementation of smart manufacturing with feedback control. Fiber super-continuum lasers may emit light in the near-infrared or SWIR between approximately 1.4-1.8 microns, 2-2.5 microns, 1.4-2.4 microns, 1-1.8 microns. In particular embodiments, the detection system may be a dispersive spectrometer, a Fourier transform infrared spectrometer, or a hyper-spectral imaging detector or camera.

19 Claims, 25 Drawing Sheets

(51) Int. Cl.
  *A61B 5/1455* (2006.01)
  *G01J 3/453* (2006.01)
  *A61B 5/00* (2006.01)
  *H01S 3/30* (2006.01)
  *G01J 3/14* (2006.01)
  *G01J 3/18* (2006.01)
  *G01J 3/28* (2006.01)

(52) U.S. Cl.
  CPC .............. *A61B 5/0075* (2013.01); *G01J 3/14* (2013.01); *G01J 3/1838* (2013.01); *G01J 2003/2826* (2013.01); *H01S 3/302* (2013.01)

(56) References Cited

U.S. PATENT DOCUMENTS

| | | |
|---|---|---|
| 4,221,997 A | 9/1980 | Flemming |
| 4,275,266 A | 6/1981 | Lasar |
| 4,374,618 A | 2/1983 | Howard |
| 4,403,605 A | 9/1983 | Tanikawa |
| 4,462,080 A | 7/1984 | Johnstone et al. |
| 4,516,207 A | 5/1985 | Moriyama et al. |
| 4,523,884 A | 6/1985 | Clement et al. |
| 4,605,080 A | 8/1986 | Lemelson |
| 4,641,292 A | 2/1987 | Tunnell et al. |
| 4,704,696 A | 11/1987 | Reimer et al. |
| 4,728,974 A | 3/1988 | Nio et al. |
| 4,762,455 A | 8/1988 | Coughlan et al. |
| 4,776,016 A | 10/1988 | Hansen |
| 4,958,910 A | 9/1990 | Taylor et al. |
| 4,989,253 A | 1/1991 | Liang et al. |
| 5,078,140 A | 1/1992 | Kwoh |
| 5,084,880 A | 1/1992 | Esterowitz et al. |
| 5,086,401 A | 2/1992 | Glassman et al. |
| 5,134,620 A | 7/1992 | Huber |
| 5,142,930 A | 9/1992 | Allen et al. |
| 5,180,378 A | 1/1993 | Kung et al. |
| 5,191,628 A | 3/1993 | Byron |
| 5,218,655 A | 6/1993 | Mizrahi |
| 5,230,023 A | 7/1993 | Nakano |
| 5,267,256 A | 11/1993 | Saruwatari et al. |
| 5,267,323 A | 11/1993 | Kimura |
| 5,300,097 A | 4/1994 | Lerner et al. |
| 5,303,148 A | 4/1994 | Mattson et al. |
| 5,305,427 A | 4/1994 | Nagata |
| 5,313,306 A | 5/1994 | Kuban et al. |
| 5,323,404 A | 6/1994 | Grubb |
| 5,345,538 A | 9/1994 | Narayannan et al. |
| 5,400,165 A | 3/1995 | Gnauck et al. |
| 5,408,409 A | 4/1995 | Glassman et al. |
| 5,458,122 A | 10/1995 | Hethuin |
| 5,544,654 A | 8/1996 | Murphy et al. |
| 5,572,999 A | 11/1996 | Funda et al. |
| 5,617,871 A | 4/1997 | Burrows |
| 5,631,758 A | 5/1997 | Knox et al. |
| 5,687,734 A | 11/1997 | Dempsey et al. |
| 5,695,493 A | 12/1997 | Nakajima et al. |
| 5,696,778 A | 12/1997 | MacPherson |
| 5,704,351 A | 1/1998 | Mortara et al. |
| 5,718,234 A | 2/1998 | Warden et al. |
| 5,747,806 A | 5/1998 | Khalil |
| 5,748,103 A | 5/1998 | Flach et al. |
| 5,792,204 A | 8/1998 | Snell |
| 5,812,978 A | 9/1998 | Nolan |
| 5,855,550 A | 1/1999 | Lai et al. |
| 5,862,803 A | 1/1999 | Besson et al. |
| 5,867,305 A | 2/1999 | Waarts et al. |
| 5,912,749 A | 6/1999 | Harstead et al. |
| 5,944,659 A | 8/1999 | Flach et al. |
| 5,950,629 A | 9/1999 | Taylor et al. |
| 5,957,854 A | 9/1999 | Besson et al. |
| 5,970,457 A | 10/1999 | Brant et al. |
| 6,014,249 A | 1/2000 | Fermann et al. |
| 6,043,927 A | 3/2000 | Islam |
| 6,115,673 A | 9/2000 | Malin |
| 6,181,414 B1 * | 1/2001 | Raz et al. ................. 356/51 |
| 6,185,535 B1 | 2/2001 | Hedin et al. |
| 6,200,309 B1 | 3/2001 | Rice et al. |
| 6,224,542 B1 | 5/2001 | Chang et al. |
| 6,246,707 B1 | 6/2001 | Yin et al. |
| 6,246,896 B1 | 6/2001 | Dumoulin |
| 6,273,858 B1 | 8/2001 | Fox et al. |
| 6,278,975 B1 | 8/2001 | Brant et al. |
| 6,281,471 B1 | 8/2001 | Smart |
| 6,285,897 B1 | 9/2001 | Kilcoyne |
| 6,289,238 B1 | 9/2001 | Besson et al. |
| 6,301,271 B1 | 10/2001 | Sanders et al. |
| 6,301,273 B1 | 10/2001 | Sanders et al. |
| 6,333,803 B1 | 12/2001 | Kurotori et al. |
| 6,337,462 B1 | 1/2002 | Smart |
| 6,340,806 B1 | 1/2002 | Smart et al. |
| 6,350,261 B1 | 2/2002 | Domankevitz et al. |
| 6,364,834 B1 | 4/2002 | Reuss et al. |
| 6,374,006 B1 | 4/2002 | Islam et al. |
| 6,381,391 B1 | 4/2002 | Islam et al. |
| 6,402,691 B1 | 6/2002 | Peddicord et al. |
| 6,407,853 B1 | 6/2002 | Samson et al. |
| 6,436,107 B1 | 8/2002 | Wang et al. |
| 6,441,747 B1 | 8/2002 | Khair et al. |
| 6,442,430 B1 | 8/2002 | Ferek-Petric |
| 6,443,890 B1 | 9/2002 | Schulze et al. |
| 6,450,172 B1 | 9/2002 | Hartlaub et al. |
| 6,453,201 B1 | 9/2002 | Daum et al. |
| 6,454,705 B1 | 9/2002 | Cosentino et al. |
| 6,458,120 B1 | 10/2002 | Shen et al. |
| 6,462,500 B1 | 10/2002 | L'Hegarat et al. |
| 6,463,361 B1 | 10/2002 | Wang et al. |
| 6,480,656 B1 | 11/2002 | Islam et al. |
| 6,512,936 B1 | 1/2003 | Monfre |
| 6,543,012 B1 | 4/2003 | Viswanathan |
| 6,549,702 B2 | 4/2003 | Islam et al. |
| 6,567,431 B2 | 5/2003 | Tabirian et al. |
| 6,587,702 B1 | 7/2003 | Ruchti |
| 6,603,910 B2 | 8/2003 | Islam et al. |
| 6,605,080 B1 | 8/2003 | Altshuler et al. |
| 6,611,643 B2 | 8/2003 | Birk |
| 6,625,180 B2 | 9/2003 | Bufetov et al. |
| 6,631,025 B2 | 10/2003 | Islam et al. |
| 6,640,117 B2 | 10/2003 | Makarewicz |
| 6,659,947 B1 | 12/2003 | Carter et al. |
| 6,659,999 B1 | 12/2003 | Anderson et al. |
| 6,738,652 B2 | 5/2004 | Mattu |
| 6,760,148 B2 | 7/2004 | Islam |
| 6,773,922 B2 | 8/2004 | Jeng |
| 6,788,965 B2 | 9/2004 | Ruchti |
| 6,802,811 B1 | 10/2004 | Slepian |
| 6,816,241 B2 | 11/2004 | Grubisic |
| 6,847,336 B1 | 1/2005 | Lemelson |
| 6,864,978 B1 | 3/2005 | Hazen |
| 6,885,498 B2 | 4/2005 | Islam |
| 6,885,683 B1 | 4/2005 | Fermann et al. |
| 6,943,936 B2 | 9/2005 | Islam et al. |
| 6,990,364 B2 | 1/2006 | Ruchti |
| 7,010,336 B2 | 3/2006 | Lorenz |
| 7,027,467 B2 | 4/2006 | Baev et al. |
| 7,060,061 B2 | 6/2006 | Altshuler et al. |
| 7,105,823 B2 * | 9/2006 | Abrahamsson et al. ...... 250/343 |
| 7,133,710 B2 | 11/2006 | Acosta |
| 7,167,300 B2 | 1/2007 | Fermann et al. |
| 7,209,657 B1 | 4/2007 | Islam |
| 7,233,816 B2 | 6/2007 | Blank |
| 7,259,906 B1 | 8/2007 | Islam |
| 7,263,288 B1 | 8/2007 | Islam |
| 7,294,105 B1 | 11/2007 | Islam |
| 7,299,080 B2 | 11/2007 | Acosta |
| 7,317,938 B2 | 1/2008 | Lorenz |
| 7,395,158 B2 | 7/2008 | Monfre |
| 7,433,116 B1 | 10/2008 | Islam |
| 7,519,253 B2 | 4/2009 | Islam |
| 7,519,406 B2 | 4/2009 | Blank |
| 7,620,674 B2 | 11/2009 | Ruchti |
| 7,697,966 B2 | 4/2010 | Monfre |
| 7,787,503 B2 | 8/2010 | Wadsworth |
| 7,787,924 B2 | 8/2010 | Acosta |

(56) References Cited

U.S. PATENT DOCUMENTS

| | | | |
|---|---|---|---|
| 7,800,818 | B2 | 9/2010 | Mattsson |
| 7,807,718 | B2 | 10/2010 | Hashim |
| 8,000,574 | B2 | 8/2011 | Buchter |
| 8,145,286 | B2 | 3/2012 | Arai |
| 8,472,108 | B2 | 6/2013 | Islam |
| 2002/0013518 | A1 | 1/2002 | West et al. |
| 2002/0019584 | A1 | 2/2002 | Schulze et al. |
| 2002/0032468 | A1 | 3/2002 | Hill et al. |
| 2002/0082612 | A1 | 6/2002 | Moll et al. |
| 2002/0109621 | A1 | 8/2002 | Khair et al. |
| 2002/0115914 | A1 | 8/2002 | Russ |
| 2002/0128846 | A1 | 9/2002 | Miller |
| 2002/0178003 | A1 | 11/2002 | Gehrke et al. |
| 2003/0022126 | A1 | 1/2003 | Buchalla |
| 2004/0174914 | A1 | 9/2004 | Fukatsu |
| 2004/0240037 | A1 | 12/2004 | Harter |
| 2005/0111500 | A1 | 5/2005 | Harter et al. |
| 2006/0223032 | A1 | 10/2006 | Fried |
| 2006/0245461 | A1 | 11/2006 | Islam |
| 2006/0268393 | A1 | 11/2006 | Islam |
| 2006/0283931 | A1* | 12/2006 | Polli et al. ............ 235/375 |
| 2007/0078348 | A1 | 4/2007 | Holman |
| 2008/0105665 | A1 | 5/2008 | Kondo |
| 2009/0028193 | A1 | 1/2009 | Islam |
| 2009/0204110 | A1 | 8/2009 | Islam |
| 2010/0046067 | A1 | 2/2010 | Fermann et al. |
| 2010/0322490 | A1 | 12/2010 | Pan |
| 2010/0331637 | A1 | 12/2010 | Ting |
| 2011/0143364 | A1 | 6/2011 | Kim |
| 2012/0013722 | A1 | 1/2012 | Wong |
| 2012/0239013 | A1* | 9/2012 | Islam ...................... 606/3 |
| 2013/0274569 | A1 | 10/2013 | Islam |
| 2014/0236021 | A1* | 8/2014 | Islam ...................... 600/475 |

FOREIGN PATENT DOCUMENTS

| | | |
|---|---|---|
| WO | WO9749340 | 12/1997 |
| WO | WO0150959 | 7/2001 |
| WO | 0189362 | 11/2001 |
| WO | 0227640 | 4/2002 |
| WO | 0228123 | 4/2002 |

OTHER PUBLICATIONS

Jasco Application Note No. 200DR0188-E, "Rapid Identification of illegal drug using NIR (identification of MDMA tablet)", Sep. 4, 2008.

Palou, A. J. Cruz, M. Blanco, J. Tomas, J. De Los Rios, M. Alcala, "Determination of drug, excipients and coating distribution in pharmaceutical tablets using NIR-CI," Journal of Pharmaceutical Analysis, vol. 2, No. 2, pp. 90-97 (2012).

Arnold, T., M. De Biasio, R. Leitner, "Near-Infrared Imaging Spectroscopy for Counterfeit Drug Detection," Next Generation Spectroscopic Technologies IV, edited by M. A. Druy, R.A. Crocombe, Proceedings of SPIE, vol. 8032, 80320Y-1 to 7, (2011).

Wedding, B.B., C. Wright, S. Grauf, R.D. White, "The application of near infrared spectroscopy for the assessment of avocado quality attributes," Infrared Spectroscopy—Life and Biomedical Sciences, pp. 211-230 (2011).

Michaels, C.A., T. Masiello, P.M. Chu, "Fourier transform spectrometry with a near infrared supercontinuum source," Optical Society of America, CLEO/IQEC Conference, paper CMDD6 (2009).

Michaels, C.A., T. Masiello, P.M. Chu, "Fourier transform spectrometry with a near-infrared supercontinuum source," Applied Spectroscopy, vol. 63, No. 5, pp. 538-543 (2009).

Moros,J., J. Kuligowski, G. Quintas, S. Garrigues, M. DeLa Guardia, "New cut-off criterion for uninformative variable elimination in multivariate calibration of near-infrared spectra for the determination of heroin in illicit street drugs," Analytica Chimica Acta, vol. 630, pp. 150-160 (2008).

Moros, J. N. Gallpienso, R. Vilches, S. Garrigues, M. DeLa Guardia, "Nondestructive direct determination of heroin in seized illicit street drugs by diffuse reflectance near-infrared spectroscopy," Analytical Chemistry, vol. 80, No. 19, pp. 7257-7265 (Oct. 1, 2008).

Roggo, Y. P. Chalus, L. Maurer, C. Lema-Martinez, A. Edmond, N. Jent, "A review of near infrared spectroscopy and chemometrics in pharaceutical technologies," Journal of Pharmaceutical and Biomedical Analysis, vol. 44, pp. 683-700 (2007).

Pojic, M. J. Mastilovic, N. Majcen, "The application of near infrared spectroscopy in wheat quality control," Infrared Spectroscopy—Life and Biomedical Sciences, pp. 167-184 (2012).

Reich, G. "Near-infrared spectroscopy and imaging: basic principles and pharmaceutical applications," Advanced Drug Delivery Reviews, vol. 57, pp. 1109-1143 (2005).

Rodionova, O.Y., L.P. Houmoller, A.L. Pomerantsev, P. Geladi, J. Burger, V.L. Dorofeyev, A.P. Arzamastsev, "NIR spectrometry for counterfeit drug detection: a feasibility study," Analytica Chimica Acta, vol. 549, pp. 151-158 (2005).

Schneider, R.C., K.A. Kovar, "Analysis of ecstasy tablets: comparison of reflectance and transmittance near infrared spectroscopy," Forensic Science International, vol. 134, pp. 187-195 (2003).

Olsen, B.A., M.W. Borer, F.M. Perry, R.A. Forbes, "Screening for counterfeit drugs using near-infrared spectroscopy," Pharmaceutical Technology, pp. 62-71 (Jun. 2002).

Scafi, S.H.F., C. Pasquini, "Identification of counterfeit drugs using near-infrared spectroscopy," Analyst, vol. 126, pp. 2218-2224 (2001).

Sondermann, N., K.A. Kovar, "Identification of ecstasy in complex matrices using near-infrared spectroscopy," Forensic Science International, vol. 102, pp. 133-147 (1999).

Rambla, F.J., S. Garrigues, M. DeLa Guardia, "PLS-NIR determination of total sugar, glucose, fructose and sucrose in aqueous solutions of fruit juices," Analytica Chimica Acta, vol. 344, pp. 41-53 (1997).

Sun, Y., C.F. Booker, S. Kumari, R.N. Day, M. Davidson, A. Periasamy, "Characterization of an orange acceptor fluorescent protein for sensitized spectral fluorescence resonant energy transfer microscopy using a white-light laser," Journal of Biomedical Optics, vol. 14, No. 5, paper 054009 (2009).

Borlinghaus, R., "Colours Count: how the challenge of fluorescence was solved in confocal microscopy," in Modern Research and Educational Topics in Microscopy, A. Mendez-Vilas and J. Diaz, eds, pp. 890-899, Formatex (2007).

Borlinghaus, R., "The White Confocal: Continuous Spectral Tuning in Excitation and Emission," in Optical Fluorescence Microscopy, A. Diaspro (Ed), Chapter 2, pp. 37-54, ISBN 978-3-642-15174-3, Springer-Verlag, Berlin (2011).

Borlinghaus, R.T., L. Kuschel, "White Light Laser: The Ultimate Source for Confocal Microscopy," http://www.leica-microsystems.com/science-lab/white-light-laser (Jun. 27, 2012).

Ziegler, U., A.G. Bittermann, M. Hoechli, "Introduction to Confocal Laser Scanning Microscopy (LEICA)," www.zmb.unizh.ch, May 29, 2013.

Islam, M. N., et al., "Broad bandwidths from frequency-shifting solitons in fibers", Optics Letters, vol. 14, No. 7, Apr. 1, 1989, pp. 370-372.

Islam, M. N., et al., "Femtosecond distributed soliton spectrum in fibers", J. Opt. Soc. Am. B, vol. 6, No. 6, Jun. 1989, pp. 1149-1158.

Busse, Lynda E., et al., "Design Parameters for Fluoride Multimode Fibers", Journal of Lightwave Technology, vol. 9, No. 7, Jul. 1991, pp. 828-831.

Wuthrich, Stefan, et al., "Optical damage thresholds at 2.94 um in fluoride glass fibers", Applied Optics, vol. 31, No. 27, Sep. 20, 1992, pp. 5833-5837.

Inoue, H., et al., "Computer simulation of the vibrational spectra and properties of fluoride glasses based on ZrF4", Journal of Non-Crystalline Solids, vol. 161, 1993, pp. 118-122.

Mizunami, Toru, et al., "Gain saturation characteristics of Raman amplification in silica and fluoride glass optical fibers", Optics Communications 97, 1993, pp. 74-78.

Desthieux, B., et al., "111 kW (0. 5 mJ) pulse amplification at 1.5 um using a gated cascade of three erbium-doped fiber amplifiers," Appl. Phys. Lett. vol. 63, Aug. 2, 1993, pp. 586-588.

Edwards, Glenn, et al., Tissue ablation by a free-electron laser tuned to the amide II band, Nature, vol. 371, Sep. 29, 1994, pp. 416-419.

(56) References Cited

OTHER PUBLICATIONS

Borrelli, N. F., et al., "Resonant and non-resonant effects in photonic glasses", Journal of Non-Crystalline Solids 185, 1995, pp. 109-122.
Asobe, Masaki, et al., "Third-order nonlinear spectroscopy in As2S3 chalcogenide glass fibers", J. Appl. Phys. 77 (11), Jun. 1, 1995, pp. 5518-5523.
Jarman, Richard H., "Novel optical fiber lasers", Current Opinion in Solid State and Materials Science, 1996, pp. 199-203.
Iatridis, James C., et al., "Is the Nucleus Pulposus a Solid or a Fluid? Mechanical Behaviors of the Nucleus Pulposus of the Human Intervertebral Disc", Spine, vol. 21(10), May 15, 1996, pp. 1174-1184.
Asobe, Masaki, "Nonlinear Optical Properties of Chalcogenide Glass Fibers and Their Application to All-Optical Switching", Optical Fiber Technology, vol. 3, Article No. OF970214, 1997, pp. 142-148.
Smektala, F., et al., "Chalcogenide glasses with large non-linear refractive indices", Journal of Non-Crystalline Solids 239, 1998, pp. 139-142.
Hamilton, James D., et al., "High Frequency Ultrasound Imaging with Optical Arrays", IEEE Transactions on Ultrasonics, Ferroelectrics, and Frequency Control, vol. 45, No. 1, Jan. 1998, pp. 216-235.
Hamilton, James D., et al., "High Frequency Ultrasound Imaging Using an Active Optical Detector", IEEE Transactions on Ultrasonics, Ferroelectrics, and Frequency Control, vol. 45, No. 3, May 1998, pp. 719-727.
Nowak, G. A., et al., "Low-power high-efficiency wavelength conversion based on modulational instability in high-nonlinearity fiber," Optics Letters, vol. 23, No. 12, Jun. 15, 1998, pp. 936-938.
Cardinal, T., et al., "Non-linear optical properties of chalcogenide glasses in the system As—S—Se", Journal of Non-Crystalline Solids 256 & 257, 1999, pp. 353-360.
Lucas, Jacques, "Infrared glasses", Current Opinion in Solid State & Materials Science 4, 1999. pp. 181-187.
Sanghera, J. S., et al., Active and passive chalcogenide glass optical fibers for IR applications: A review, Journal of Non-Crystalline Solids 256 & 257, 1999, pp. 6-16.
Nishida, Yoshiki, et al., "Reliability of Fluoride Fiber Module for Optical Amplifier Use", IEEE Photonics Technology Letters, vol. 11, No. 12, Dec. 1999, pp. 1596-1598.
Nowak, George A., et al., "Stable supercontinuum generation in short lengths of conventional dispersion-shifted fiber", Applied Optics, vol. 38, No. 36, Dec. 20, 1999, pp. 7364-7369.
Urban, J. P. G., et al., "The Nucleus of the Intervertebral Disc from Development to Degeneration" Amer. Zool., vol. 40, 2000, pp. 53-61.
Hamilton, James D., et al., "High Frequency Optoacoustic Arrays Using Etalon Detection", IEEE Transactions on Ultrasonics, Ferroelectrics, and Frequency Control, vol. 47, No. 1, Jan. 2000, pp. 160-169.
Ranka, Jinendra K., et al., "Visible continuum generation in air-silica microstructure optical fibers with anomalous dispersion at 800 nm", Optics Letters, vol. 25, No. 1, Jan. 1, 2000, pp. 25-27.
Boult, Maggi, et al., "Systematic Review of Percutaneous Endoscopic Laser Discectomy: Update and Re-appraisal", Australian Safety and Efficacy Register of New Interventional Procedures—Surgical Report No. 5, Feb. 2000, 49 pages.
Boult, Maggi, et al., "Percutaneous Endoscopic Laser Discectomy", Systematic Review, Aust. N.Z.J. Surg., vol. 70, Apr. 7, 2000 pp. 475-479.
Camacho, Nancy P., et al., "FTIR Microscopic Imaging of Collagen and Proteoglycan in Bovine Cartilage," Biopolymers (Biospectroscopy), vol. 62, 2001, pp. 1-8.
Choi, Joon Y., et al, "Thermal, Mechanical, Optical, and Morphologic Changes in Bovine Nucleus Pulposus Induced by Nd:YAG (*=1.32 um) Laser Irradiation", Lasers in Surgery and Medicine, vol. 28, 2001, pp. 248-254.

Hafez, M. I., et al., "The Effect of Irrigation on Peak Temperatures in Nerve Root, Dura, and Intervertebral Disc During Laser-Assisted Foraminoplasty", Lasers in Surgery and Medicine, vol. 29, 2001, pp. 33-37.
Jackson, Stuart D., et al., "Theory and numerical simulation of nth-order cascaded Raman fiber lasers", J. Opt. Soc. Am. B, vol. 18, No. 9, Sep. 2001, pp. 1297-1306.
Werle, Peter, et al., "Near- and mid-infrared laser-optical sensors for gas analysis", Optics and Lasers in Engineering 37, 2002, pp. 101-114.
Beck, Mattias, et al., "Continuous Wave Operation of a Mid-Infrared Semiconductor Laser at Room Temperature," Science vol. 295, www.sciencemag.org, Jan. 11, 2002, pp. 301-305.
Harbold, J. M., et al., "Highly nonlinear As—S—Se glasses for all-optical switching", Optics Letters, vol. 27, No. 2, Jan. 15, 2002, pp. 119-121.
Coen, Stephane, et al., "Supercontinuum generation by stimulated Raman scattering and parametric four-wave mixing in photonic crystal fibers", J. Opt. Soc. Am. B, vol. 19, No. 4, Apr. 2002, pp. 753-764.
Dudley, John M., et al., "Supercontinuum generation in air-silica microstructured fibers with nanosecond and femtosecond pulse pumping", J. Opt. Soc. Am. B, vol. 19, No. 4, Apr. 2002, pp. 765-771.
Harbold, Jeffrey M., et al., "Highly Nonlinear Ge—As—Se and. Ge—As—S—Se Glasses for All-Optical Switching", IEEE Photonics Technology Letters, vol. 14, No. 6, Jun. 2002, pp. 822-824.
Husakou, Anton V., et al, "Supercontinuum generation, four-wave mixing, and fission of higher-order solitons in photonic-crystal fibers", J. Opt. Soc. Am. B, vol. 19, No. 9, Sep. 2002, pp. 2171-2182.
Wadsworth, William J., et al., "Supercontinuum generation in photonic crystal fibers and optical fiber tapers: a novel light source", J. Opt. Soc. Am. B, vol. 19, No. 9, Sep. 2002, pp. 2148-2155.
Kumar, V.V. Ravi Kanth, et al, "Extruded soft glass photonic crystal fiber for ultrabroad supercontinuum generation", Optics Express, vol. 10, No. 25, Dec. 16, 2002, pp. 1520-1525.
Edwards, Glenn S., et al., "Advantage of the Mark-III FEL for biophysical research and biomedical applications", J. Synchrotron Rad. vol. 10, 2003, pp. 354-357.
Nicholson, J. W., et al., "Pulsed and continuous-wave supercontinuum generation in highly nonlinear, dispersion-shifted fibers", Applied Physics B 77, 2003, pp. 211-218.
Sobol, Emil, et al., "Time-resolved, light scattering measurements of cartilage and cornea denaturation due to free electron laser radiation", Journal of Biomedical Optics, vol. 8, No. 2, Apr. 2003, pp. 216-222.
Nicholson, J. W., et al., "All-fiber, octave-spanning supercontinuum", Optics Letters, vol. 28, No. 8, Apr. 15, 2003, pp. 643-645.
Faralli, S., et al., "Impact of Double Rayleigh Scattering Noise in Distributed Higher Order Raman Pumping Schemes", IEEE Photonics Technology Letters, vol. 15, No. 6, Jun. 2003, pp. 804-806.
"New and Emerging Techniques—Surgical, Rapid Review, Laser Discectomy", Australian Safety and Efficacy Register of New Interventional Procedures—Surgical, Jun. 2003, 12 pages.
Avdokhin, A. V., et al, "Continuous-wave, high-power, Raman continuum generation in holey fibers", Optics Letters, vol. 28, No. 15, Aug. 1, 2003, pp. 1353-1355.
Mussot, Arnaud, et al., "Generation of a broadband single-mode supercontinuum in a conventional dispersion-shifted fiber by use of a subnanosecond microchip laser", Optics Letters, vol. 28, No. 19, Oct. 1, 2003, pp. 1820-1822.
Slusher, Richard, et al., "Highly nonlinear composite chalcogenide/polymer fibers", OSA 2004, 1 page.
Thongtrangan, Issada, et al., "Minimally invasive spinal surgery: a historical perspective", Neurosurg. Focus, vol. 16, Article 13, Jan. 2004, pp. 1-10.
Hori, Takashi, et al., "Flatly broadened, wideband and low noise supercontinuum generation in highly nonlinear hybrid fiber", Optics Express, vol. 12, No. 2, Jan. 26, 2004, pp. 317-324.
Wadsworth, W. J., et al., "Supercontinuum and four-wave mixing with Q-switched pulses in endlessly single-mode photonic crystal fibres", Optics Express, vol. 12, No. 2, Jan. 26, 2004, pp. 299-309.
Hilligsoe, Karen Marie, et al., "Supercontinuum generation in a photonic crystal fiber with two zero dispersion wavelengths", Optics Express, vol. 12, No. 6, Mar. 22, 2004, pp. 1045-1054.

(56) References Cited

OTHER PUBLICATIONS

Venugopalan, V., "Optical Society of America BIOMED Topical Meeting Tutorial on Tissue Optics", Apr. 27, 2004, pp. 1-32.
Slusher, Richart E., et al., "Large Raman gain and nonlinear phase shifts in high-purity As2So3 chalcogenide fibers", J. Opt. Soc. Am. B, vol. 21, No. 6, Jun. 2004, pp. 1146-1155.
Leon-Saval, S. G., et al., "Supercontinuum generation in submicron fibre waveguides", Optics Express, vol. 12, No. 13, Jun. 28, 2004, pp. 2864-2869.
Nicholson, J. W., et al., "High power, single mode, all-fiber source of femtosecond pulses at 1550 nm and its use in supercontinuum generation", Optics Express, vol. 12, No. 13, Jun. 28, 2004, pp. 3025-3034.
Genty, G., et al., "Enhanced bandwidth of supercontinuum generated m microstructured fibers", Optics Express, vol. 12, No. 15, Jul. 26, 2004, pp. 3471-3480.
Champert, Pierre-Alain, et al., "White-light supercontinuum generation in normally dispersive optical fiber using original multi-wavelength pumping system", Optics Express, vol. 12, No. 19, Sep. 20, 2004, pp. 4366-4371.
Nicholson, J. W., "Supercontinuum generation in ultraviolet-irradiated fibers", Optics Letters, vol. 29, No. 20, Oct. 15, 2004, pp. 2363-2365.
Hori, Takashi, et al., "Experimental and numerical analysis of widely broadened supercontinuum generation in highly nonlinear dispersion-shifted fiber with a femtosecond pulse", J. Opt. Soc. Am. B, vol. 21, No. 11, Nov. 2004, pp. 1969-1980.
Demircan, Ayhan, et al., "Supercontinuum generation by the modulation instability", Optics Communications 244, 2005, pp. 181-185.
Papernyi, S. B., et al., "Sixth-Order Cascaded Raman Amplification", OFC/NFOEC, 2005, 3 pages.
Tanaka, Keiji, "Optical nonlinearity in photonic glasses", Journal of Materials Science: Materials in Electronics 16, 2005, pp. 633-643.
Westbrook, Paul S., "Improved Supercontinuum Generation Through UV Processing of Highly Nonlinear Fibers", Journal of Lightwave Technology, vol. 23, No. 1, Jan. 2005, pp. 13-18.
Abeeluck, Akheelesh K., et al., "Continuous-wave pumping in the anomalous- and normal dispersion regimes of nonlinear fibers for supercontinuum generation", Optics Letters, vol. 30, No. 1, Jan. 1, 2005, pp. 61-63.
Kutz, J. Nathan, et al., Enhanced Supercontinuum Generation through Dispersion-Management, Optics Express, vol. 13, No. 11, May 30, 2005, pp. 3989-3998.
Lee, Ju Han, et al., "Experimental performance comparison for various continuous-wave supercontinuum schemes: ring cavity and single pass structures", Optics Express, vol. 13, No. 13, Jun. 27, 2005, pp. 4848-4853.
Saliminia, A., et al., "Ultra-broad and coherent white light generation in silica glass by focused femtosecond pulses at 1.5pm", Optics Express, vol. 13, No. 15, Jul. 25, 2005, pp. 5731-5738.
Takushima, Yuichi, High average power, depolarized super-continuum generation using a 1.55-um ASE noise source, Optics Express, vol. 13, No. 15, Jul. 25, 2005, pp. 5871.-5877.
Travers, J. C., et al., "Extended continuous-wave supercontinuum generation in a low-water-loss holey fiber", Optics Letters, vol. 30, No. 15, Aug. 1, 2005, pp. 1938-1940.
Kobtsev, Serguei M., et al., "Modelling of high-power supercontinuum generation in highly nonlinear, dispersion shifted fibers at CW pump", Optics Express, vol. 13, No. 18, Sep. 5, 2005, pp. 6912-6918.
Falk, Peter, et al., "Supercontinuum generation in a photonic crystal fiber with two zero-dispersion wavelengths tapered to normal dispersion at all wavelengths", Optics Express, vol. 13, No. 19, Sep. 19, 2005, pp. 7535-7540.
Tombelaine, Vincent, et al., "Ultra wide band supercontinuum generation in air-silica holey fibers by SHG-induced modulation instabilities", Optics Express, vol. 13, No. 19, Sep. 19, 2005, pp. 7399-7404.

Lee, Ju Han, et al., "Continuous-wave supercontinuum laser based on an erbium-doped fiber ring cavity incorporating a highly nonlinear optical fiber", Optics Letters, vol. 30, No. 19, Oct. 1, 2005, pp. 2599-2601.
Genty, G., et al., "Supercontinuum generation in large mode-area microstructured fibers", Optics Express, vol. 13, No. 21, Oct. 17, 2005, pp. 8625-8633.
Schreiber, T., et al., "Supercontinuum generation by femtosecond single and dual wavelength pumping in photonic crystal fibers with two zero dispersion wavelengths", Optics Express, vol. 13, No. 23, Nov. 14, 2005, pp. 9556-9569.
Travers, J. C., et al., "Extended blue supercontinuum generation in cascaded holey fibers", Optics Letters, vol. 30, No. 23, Dec. 1, 2005, pp. 3132-3134.
Hagen, C. L., et al., "Generation of a Continuum Extending to the Midinfrared by Pumping ZBLAN Fiber With an Ultrafast 1550-nm Source", IEEE Photonics Technology Letters, vol. 18, No. 1, Jan. 1, 2006, pp. 91-93.
Moon, Sucbei, et al., "Generation of octave-spanning supercontinuum with I550-nm amplified diode-laser pulses and a dispersion-shifted fiber", Optics Express, vol. 14, No. 1, Jan. 9, 2006, pp. 270-278.
Fedotova, O., et al., "Supercontinuum generation in planar rib waveguides enabled by anomalous dispersion", Optics Express, vol. 14, No. 4, Feb. 20, 2006, pp. 1512-1517.
Harrington, James A., "Infrared Fiber Optics", OSA Handbook, vol. III, white paper, to be published by McGraw Hill, Undated, 13 pages.
Aaviksoo, J., et al., "Observation of optical precursors at pulse propagation in GaAs", Physical Review A, vol. 44, No. 9, Nov. 1, 1991, pp. R5353-R5356.
Boppart, Stephen A., et al., "Imaging developing neural morphology using optical coherence tomography", Journal of Neuroscience Methods 70, 1996, pp. 65-72.
Boppart, Stephen A., et al., "Noninvasive assessment of the developing Xenopus cardiovascular system using optical coherence tomography", Prec. Natl. Acad. Sci. USA, vol. 94, Apr. 1997, pp. 4256-4261.
Tearney, Guillermo J., et al., "In vivo Endoscopic Optical Biopsy with Optical Coherence Tomography", Science, New Series, vol. 276, Jun. 27, 1997, pp. 2037-2039.
de Boer, Johannes F., et al., "Imaging thermally damaged tissue by polarization sensitive optical coherence tomography", Optics Express 212, vol. 3, No. 6, Sep. 14, 1998, pp. 212-218.
Roggan, Andre, et al., "Optical Properties of Circulating Human Blood in the Wavelength Range 400-2500 NM", Journal of Biomedical Optics, vol. 4, No. 1, Jan. 1999, pp. 36-46.
de Boer, Johannes F., et al., "Determination of the depth-resolved Stokes parameters of light backscattered from turbid media by use of polarization-sensitive optical coherence tomography", Optics Letters, vol. 24, No. 5; Mar. 1, 1999, pp. 300-302.
Rollins, Andrew M., et al., "Real-time in vivo imaging of human gastrointestinal ultrastructure by use of endoscopic optical coherence tomography with a novel efficient interferometer design", Optics Letters, vol. 24, No. 19, Oct. 1, 1999, pp. 1358-1360.
D'Amico, Anthony V., et al., "Optical Coherence Tomography as a Method for Identifying Benign and Malignant Microscopic Structures in the Prostate Gland", Basic Science, Urology 55 (5), 2000, pp. 783-787.
Li, Xingde, et al., "Imaging needle for optical coherence tomography", Optics Letters, vol. 25, No. 20, Oct. 15, 2000, pp. 1520-1522.
Oughstun, Kurt E., "Influence of precursor fields on ultrashort pulse autocorrelation measurements and pulse width evolution", Optics Express, vol. 8, No. 8, Apr. 9, 2001, pp. 481-491.
Kowalevicz, Andrew M., et al., "Ultrahigh resolution optical coherence tomography using a superluminescent light source" Optics Express 349, vol. 10, No. 7, Apr. 8, 2002, pp. 349-353.
Povazay, B., et al., "Submicrometer axial resolution optical coherence tomography", Optics Letters, vol. 27, No. 20, Oct. 15, 2002, pp. 1800-1802.

(56) References Cited

OTHER PUBLICATIONS

Xie, T.-Q., et al., "Detection of tumorigenesis in urinary bladder with optical coherence tomography: optical characterization of morphological changes", Optics Express, vol. 10, No. 24, Dec. 2, 2002, 2003, pp. 1431-1443.
Seefeldt, Michael, et al., "Compact white-light source with an average output power of 2.4 Wand 900 nm spectral bandwidth", Optics Communications 216, pp. 199-202.
Wang, Yimin, et al., "Ultrahigh-resolution optical coherence tomography by broadband continuum generation from a photonic crystal fiber", Optics Letters, vol. 28, No. 3, Feb. 1, 2003, pp. 182-184.
Bizheva, K, et al., "Compact, broad-bandwidth fiberlaserforsub-2-pm axial resolution optical coherence tomography in the 1300-nm wavelength region," Optics Letters, vol. 28, No. 9, May 1, 2003, pp. 707-709.
Pan, Yingtian, et al., "Hand-held arthroscopic optical coherence tomography for in vivo high-resolution imaging of articular cartilage", Journal of Biomedical Optics 8(4), Oct. 2003, pp. 648-654.
Xie, Tuqiang, et al., "Endoscopic optical coherence tomography with a modified microelectromechanical systems mirror for detection of bladder cancers", Applied Optics, vol. 42, No. 31, Nov. 1, 2003, pp. 6422-6426.
Dubois, A., et al., "Three-dimensional cellular-level imaging using full-field optical coherence tomography", Physics in Medicine and Biology, Phys. Med. Biol. 49, 2004, pp. 1227-1234.
Park, Jesung, et al., "Analysis of birefringent image in the retinal nerve fiber layer by polarization sensitive optical coherence tomography", Ophthalmic Technologies XIV, Proceedings of SPIE, vol. 5314, 2004, pp. 188-194.
Unterhuber, A., et al., "Advances in broad bandwidth light sources for ultrahigh resolution optical coherence tomography", Physics in Medicine and Biology, Phys. Med. Biol. 49, 2004, pp. 1235-1246.
Drexler, Wolfgang, "Ultrahigh-resolution optical coherence tomography", Journal of Biomedical Optics, vol. 9, No. 1, Jan./Feb. 2004, pp. 47-74.
Schmitt, Joseph, et al., "Intravascular Optical Coherence Tomography Opens a Window Onto Coronary Artery Disease", Optics & Photonics News, Feb. 2004, pp. 20-25.
Nassif, N.A., et al., "In vivo high-resolution video-rate spectral-domain optical coherence tomography of the human retina and optic nerve", Optics Express, vol. 12, No. 3, Feb. 9, 2004, pp. 367-376.
Choi, Seung-Ho, et al., "Observation of Optical Precursors in Water", Physical Review Letters, vol. 92, No. 19, May 14, 2004, pp. 193903-1-193903-.3.
Pierce, Mark C., et al., "Advances in Optical Coherence Tomography imaging for Dermatology", Optical Coherence Tomography Advances, The Journal of Investigative Dermatology, Sep. 3, 2004, pp. 458-463.
"State-Specific Trends in Chronic Kidney Failure—United States, 1990-2001", Morbidity and Mortality Weekly Report, Department of Health and Human Services Centers for Disease Control and Prevention, vol. 53, No. 39, copied from internet: file://C:\Documents and Settings\eturlo\Desktop\State-Specific Trends in Chronic Kidney ... Feb. 12, 2010, Oct. 8, 2004, pp. 918-920.
I.B. Ads, A.A.E. Wagie, N.B. Mariun, A.B.E. Jammal, "An Internet-based blood pressure monitoring system for patients," Journal of Telemedicine and Telecare, 2001, pp. 51-53.
R.H. Istepanian, B. Woodward, P.A. Bales, S. Chen, B. Luk, "The comparative performance of mobile telemediCal systems based on the IS-54 and GSM cellular telephone standards," Journal of Telemedicine and Telecare, 1999, pp. 97-104.
Shaw, et al, IR Supercontinuum Generation in As—Se Photonic Crystal Fiber, Optical Society of America, Copyright 2005, 3 pages.
PCT/US06/44451, Notification of Transmittal of the International Search Report and the Written Opinion of the International Searching Authority, or the Declaration, Nov. 29, 2007, 12 pages.
G.S. Edwards et al., "Free-electron-laser-based biophysical and biomedical instrumentation," American Institute of Physics, vol. 74, No. 7, Jul. 2003, pp. 3207-3245.

Computer Motion, Inc., "501(k) Summary—Zeus® MicroWrist™ Surgical System and Accessories," Sep. 24, 2002, 6 pages.
Computer Motion, Inc. "Hermes™ O.R. Control Center—510(k) Summary of Safety and Effectiveness," Oct. 11, 2002, 5 pages.
K.M. Joos, et al. "Optic Nerve Sheath Fenestration with a Novel Wavelength Produced by the Free Electron Laser (FEL)," Lasers in Surgery and Medicine, 27: 2000,191-205.
J. Sanghera, I. Aggarwal, "IR Fiber Optics at NRL," undated, 10 pages.
J. Sanghera, L.B. Shaw, I.D. Aggarwal, "Applications of chalcogenide glass optical fibers," Academic of Science, 2003, pp. 1-11.
B. Rigas, P.T.T. Wong, "Human Colon Adenocarcinoma Cell Lines Display Infrared Spectroscopic Features," Cancer Research, Jan. 1, 1992, pp. 84-88.
G. Edwards, et al., "Comparison of OPA and Mark-III Fel for Tissue Ablation at 6.45 Microns," Department of Physics and Free Electron Laser Laboratory, Duke University, 2002, 7 pages.
Glenn Edwards, "Biomedical and potential clinical applications for pulsed lasers operating near 6.45 um," Society of Photo-Optical Instrumentation Engineers, 1995, 2 pages.
Passat, "Solid-State Lasers and Optical Components," Jul. 14, 2003, 5 pages.
P.A. Thielen and L.B. Shaw, et al., "Small-core As—Se fiber for Raman amplification," Optics LETI-ERS, vol. 28, No. 16, Aug. 15, 2003, 3 pages.
R.Rox Anderson, et al., "Selective Photothermolysis: Precise Microsurgery by Selective Absorption of Pulsed Radiation," Department of Dermatology, Harvard Medical School, Science, vol. 220, Apr. 29, 1983, 4 pages.
U.S. Appl. No. 10/652,276, "System and Method for Voice Control of Medical devices," by Mohammed N. Islam, abandoned, filed Aug. 29, 2003.
U.S. Appl. No. 10/757,341, "System and Method for Voice Control of Medical devices," by Mohammed N. Islam, issued, filed Jan. 13, 2004.
U.S. Appl. No. 12/206,432, "System and Method for Voice Control of Medical Devices," by Mohammed N. Islam, pending, filed Sep. 8, 2008.
U.S. Patent and Trademark Office, Office Action for U.S. Appl. No. 12/206,432, filed Sep. 8, 2008, Mohammed N, Islam, Date filed: Mar. 12, 2009.
U.S. Patent and Trademark Office, Notice of Allowance and Fee(s) Due for U.S. Appl. No. 12/206,432, filed Sep. 8, 2008, Mohammed N. Islam, Date filed: Aug. 28, 2009.
Hazen, K.H., M.A. Arnold, G.W. Small, "Measurement of glucose and other analytes in undiluted human serum with near-infrared transmission spectroscopy," Analytica Chimica Acta, vol. 371, pp. 255-267 (1998).
Malin, S.F., T.L. Ruchti, T.B. Blank, S.N. Thennadil, S.L. Monfre, "Noninvasive prediction of glucose by near-infrared diffuse reflectance spectroscopy," Clinical Chemistry, vol. 45, No. 9, pp. 1651-1658 (1999).
Thennadil, S.N., J.L. Rennert, B.J. Wenzel, K.H. Hazen, T.L. Ruchti, M.B. Block, "Comparison of glucose concentration in interstitial fluid, and capillary and venous blood during rapid changes in blood glucose levels," Diabetes Technology & Therapeutics, vol. 3, No. 3, pp. 357-365 (2001).
Troy, T.L., S.N. Thennadil, "Optical properties of human skin in the near infrared wavelength range of 1000 to 2200nm," Journal of Biomedical Optics, vol. 6, No. 2, pp. 167-176, (2001).
Blank, T.B., T.L. Ruchti, A.D. Lorenz, S.L. Monfre, M.R. Makarewicz, M. Mattu, K.H. Hazen, "Clinical results from a non-invasive blood glucose montior," Optical Diagnostics and Sensing of Biological Fluids and Glucose and Cholesterol Monitoring II, A.V. Priezzhev and G.L. Cote, Editors, Proceedings of SPIE, vol. 4624, pp. 1019 (2002).
Yeh, S-J, C.F. Hanna, O.S. Khalil, "Monitoring blood glucose changes in cutaneous tissue by temperature-modulated localized reflectance measurements," Clinical Chemistry, vol. 49, No. 6, pp. 924-934 (2003).

(56) References Cited

OTHER PUBLICATIONS

Marbach, R., T. Koschinsky, F.A. Gries, H.M. Heise, "Noninvasive blood glucose assay by near-infrared diffuse reflectance spectroscopy of the human inner lip," Applied Spectroscopy, vol. 47, No. 7, pp. 875-881 (1993).
Enejder, A.M.K., T.G. Scecina, J. Oh, M. Hunter, W.C. Shih, S. Sasic, G.L. Horowitz, M.S. Feld, "Raman spectroscopy for noninvasive glucose measurements," Journal of Biomedical Optics, vol. 10, No. 3, 031114 (2005).
Olesberg, J.T., L. Liu, V.V. Zee, M.A. Arnold, "In vivo near-infrared spectroscopy of rat skin tissue with varying blood glucose levels," Analytic Chemistry, vol. 78, No. 1, pp. 215-223 (2006).
Olesberg, J.T., M.A. Arnold, C. Mermelstein, J. Schmitz, J. Wagner, "Tunable laser diode system for noninvasive blood glucose measurements," Applied Spectroscopy, vol. 59, No. 12, pp. 1480-1484 (2005).
Harman-Boehm, I. A. Gal, A.M. Raykhman, J.D. Zahn, E. Naidis, Y. Mayzel, "Noninvasive glucose monitoring: a novel approach," Journal of Diabetes Science and Technology, vol. 3, No. 2 pp. 253-260 (2009).
Kim-K.D., G.S. Son, S.S. Lim, S.S. Lee, "Measurement of glucose level exploiting a relative optical absorption at discrete probe wavelengths," Japanese Journal of Applied Physics, vol. 48, 077001 (2009).
Smith, J.L., "The Pursuit of Noninvasive Glucose: Hunting the Deceitful Turkey," 2nd Edition, pp. 1-141 (2011).
Pezzaniti, J.L., T.W. Jeng, L. McDowell, G.M. Oosta, "Preliminary investigation of near-infrared spectroscopic measurements of urea, creatinine, glucose, protein and ketone in urine," Clinical Biochemistry, vol. 34, pp. 239-246 (2001).
Lussi, A., R. Hibst, R. Paulus, "Diagnodent: An optical method for caries detection," Journal of Dental Research, vol. 83, special issue C, pp. C80-C83 (2004).
Reese, E.L, E.E. Fisher, D.A. Horowitz, "Photoelectric densitometry of the circulation of the human dental pulp," The Journal of the Baltimore College of Dental Surgery, vol. 26, No. 1, pp. 6-18 (1971).
Zakian, C., I. Pretty, R. Ellwood, "Near-infrared hyperspectral imaging of teeth for dental caries detection," Journal of Biomedical Optics, vol. 16, No. 6, 064047 (2009).
Belikov, A.V., A.V. Skripnik, K.V. Shatilova, "Study of the dynamics of the absorption spectra of human tooth enamel and dentine under heating and ablation by submillisecond pulse radiation of an erbium laser with a generation wavelength of 2.79 um," Optics and Spectroscopy, vol. 109, No. 2, pp. 211-216 (2010).
Karlsson, L. "Caries detection methods based on changes in optical properties between healthy and carious tissue," International Journal of Dentistry, vol. 2010, Article ID 270729, 9 pages (2010).
Fried, D. M. Staninec, C.L. Darling, "Near-infrared imaging of dental decay at 1310nm," Journal of Laser Dentistry, vol. 18, No. 1, pp. 8-16 (2010).
Burmen, M. P. Usenik, A. Fidler, F. Pernus, B. Likar, "A construction of standardized near infrared hyper-spectral teeth database—a first step in the development of reliable diagnostic tool for quantification and early detection of caries," Lasers in Dentistry XVII, edited by P. Rechmann, D. Fried, Proceedings of SPIE, vol. 7884, Paper 78840E (2011).
Maia, A., L. Karlsson, W. Margulis, A. Gomes, "Evaluation of two imaging techniques: near-infrared transillumination and dental radiographs for the detection of early approximal enamel caries," Dentomaxillofacial Radiology, vol. 40, pp. 429-433 (2011).
Chung, S., D. Fried, M. Staninec, C.L. Darling, "Multispectral near-IR reflectance and transillumination imaging of teeth," Biomedical Optics Express, vol. 2, No. 10, pp. 2804-2814 (2011).
Chung, S., D. Fried, M. Staninec, C.L. Darling, "Near infrared imaging of teeth at wavelengths between 1200 and 1600nm," Proceedings of the Society of Photo Optical Instrument Engineering, paper 7884 (2011).
Staninec, M., S.M. Douglas, C.L. Darling, K. Chan, H. Kang, R. C. Lee, D. Fried, "Nondestructive clinical assessment of occlusal caries lesions using near-IR imaging methods," Lasers in Surgery and Medicine, vol. 43, No. 10, pp. 951-959 (2011).
Nishizawa, N., "Generation and application of high-quality supercontinuum sources," Optical Fiber Technology, vol. 18, pp. 394-402 (2012).
Istepanian, Robert H., "The Comparative Performance of Mobile Telemedical Systems based on the IS-54 and GSM Cellular Telephone Standards"; Journal of Telemedicine and Telecare 1999; pp. 97-104.
Aris, Ishak Bin, "An Internet-Based Blood Pressure Monitoring System for Patients"; Journal of Telemedicine and Telecare 2001; pp. 51-53.

* cited by examiner

| TENTATIVE FREQUENCIES OF HEROIN BANDS (nm) | ACTUALLY MEASURED PEAK FREQUENCIES (nm) | FORMS OF MODES OF VIBRATION ASSIGNMENT |
|---|---|---|
| 1160 | 1157 | C—O STRETCH FOURTH OVERTONE |
| 1195 | 1190 | C—H SECOND OVERTONE |
|  | 1200 | C—H SECOND OVERTONE |
| 1360 | 1357 | C—H COMBINATION |
| 1395 | 1391 | C—H COMBINATION |
| 1420 | 1425 | O—H FIRST OVERTONE |
| 1570 | 1570 | N—H STRETCH FIRST OVERTONE |
| 1685 | 1684 | C—H STRETCH FIRST OVERTONE |
| 1705 | 1709 | C—H STRETCH FIRST OVERTONE |
| 1725 | 1727 | C—H STRETCH FIRST OVERTONE |
| 1765 | 1767 | C—H STRETCH FIRST OVERTONE |
| 1780 | 1780 | C—H STRETCH FIRST OVERTONE |
| 1920 | 1914 | C—O STRETCH SECOND OVERTONE |
| 1950 | 1936 | C—O STRETCH SECOND OVERTONE |
| 1990 | 2000 | N—H STRETCH/N—H BEND COMBINATION |
| 2070 | 2074 | N—H DEFORMATION OVERTONE |
| 2090 | 2100 | C—H COMBINATION |
| 2140 | 2135 | C—H STRETCH/C—O STRETCH COMBINATION OR SYM C—H DEFORMATION |
|  | 2144 | C—H STRETCH/C—O STRETCH COMBINATION OR SYM C—H DEFORMATION |

FROM FIG. 9A

| | | |
|---|---|---|
| 2170 | 2172 | ASYMMETRIC C—H STRETCH/C—H DEFORMATION COMBINATION |
| 2180 | 2178 | N—H BEND SECOND OVERTONE OR C—H STRETCH/C—O STRETCH COMBINATION, OR C—O STRETCH C—N STRETCH; N—H IN-PLANE BEND. |
| 2200 | 2194 | CH STRETCH/C—O STRETCH COMBINATION |
| 2280 | 2284 | C—H STRETCH/CH$_2$ DEFORMATION |
| 2300 | 2300 | C—H BEND SECOND OVERTONE |
| 2325 | 2320 | CH STRETCH/CH$_2$ DEFORMATION COMBINATION |
| 2352 | 2352 | CH$_2$ BEND SECOND OVERTONE |
| 2380 | 2384 | C—H STRETCH/C—C STRETCH COMBINATION |
| 2470 | 2454 | C—H COMBINATION OR SYM C—N—C STRETCH OVERTONE |
| 2488 | 2485 | C—H STRETCH/C—C STRETCH COMBINATION |
| 2530 | 2524 | ASYMMETRIC C—N—C STRETCH FIRST OVERTONE |
| 2530 | 2537 | ASYMMETRIC C—N—C STRETCH FIRST OVERTONE |

FIG. 9B

SHORT-WAVE INFRARED SUPER-CONTINUUM LASERS FOR DETECTING COUNTERFEIT OR ILLICIT DRUGS AND PHARMACEUTICAL PROCESS CONTROL

CROSS-REFERENCE TO RELATED APPLICATIONS

This application claims the benefit of U.S. provisional application Ser. No. 61/747,487 filed Dec. 31, 2012, the disclosure of which is hereby incorporated in its entirety by reference herein.

This application is related to U.S. provisional application Ser. Nos. 61/747,477 filed Dec. 31, 2012; Ser. No. 61/747,481 filed Dec. 31, 2012; Ser. No. 61/747,485 filed Dec. 31, 2012; Ser. No. 61/747,472 filed Dec. 31, 2012; Ser. No. 61/747,492 filed Dec. 31, 2012; Ser. No. 61/747,553 filed Dec. 31, 2012; and Ser. No. 61/754,698 filed Jan. 21, 2013, the disclosures of which are hereby incorporated in their entirety by reference herein This application is being filed concurrently with International Application No. PCT/US2013/075700 (Publication No. WO/2014/105520) entitled Near-Infrared Lasers For Non-Invasive Monitoring Of Glucose, Ketones, HBA1C, And Other Blood Constituents; International Application PCT/US2013/075736 (Publication No. WO/2014/105521) entitled Short-Wave Infrared Super-Continuum Lasers For Early Detection Of Dental Caries; U.S. application Ser. No. 14/108,995 (Publication No. 2014/0188092) entitled Focused Near-Infrared Lasers For Non-Invasive Vasectomy And Other Thermal Coagulation Or Occlusion Procedures; International Application PCT/US2013/075767 (Publication No. WO/2014/143276) entitled Short-Wave Infrared Super-Continuum Lasers For Natural Gas Leak Detection, Exploration, And Other Active Remote Sensing Applications; U.S. application Ser. No. 14/108,974 (Publication No. 2014/0188094) entitled Non-Invasive Treatment Of Varicose Veins; and U.S. application Ser. No. 14/109,007 (Publication No. 2014/0236021) entitled Near-Infrared Super-Continuum Lasers For Early Detection Of Breast And Other Cancers, the disclosures of which are hereby incorporated in their entirety by reference herein.

TECHNICAL FIELD

This disclosure relates to lasers and light sources for remote or stand-off identification of counterfeit drugs, detection of illicit drugs, or process control in the pharmaceutical industry including systems and methods for using near-infrared or short-wave infrared light sources for remote detection of counterfeit or illicit drugs and process control at remote or stand-off distances in the pharmaceutical industry.

BACKGROUND AND SUMMARY

Counterfeiting of pharmaceuticals is a significant issue in the healthcare community as well as for the pharmaceutical industry worldwide. For example, according to the World Health Organization, in 2006 the market for counterfeit drugs worldwide was estimated at around $43 Billion. Moreover, the use of counterfeit medicines may result in treatment failure or even death. For instance, in 1995 dozens of children in Haiti and Nigeria died after taking counterfeit medicinal syrups that contained diethylene glycol, an industrial solvent. As another example, in Asia one report estimated that 90% of Viagra sold in Shanghai, China, was counterfeit. With more pharmaceuticals being purchased through the internet, the problem of counterfeit drugs coming from across the borders into the United States has been growing rapidly.

A rapid, non-destructive, non-contact optical method for screening or identification of counterfeit pharmaceuticals is needed. Spectroscopy using near-infrared or short-wave infrared (SWIR) light may provide such a method, because most pharmaceuticals comprise organic compounds that have overtone or combination absorption bands in this wavelength range (e.g., between approximately 1-2.5 microns). Moreover, most drug packaging materials are at least partially transparent in the near-infrared or SWIR, so that drug compositions may be detected and identified through the packaging non-destructively. Also, using a near-infrared or SWIR light source with a spatially coherent beam permits screening at stand-off or remote distances. Beyond identifying counterfeit drugs, the near-infrared or SWIR spectroscopy may have many other beneficial applications. For example, spectroscopy may be used for rapid screening of illicit drugs or to implement process analytical technology in pharmaceutical manufacturing. There are also a wide array of applications in assessment of quality in the food industry, including screening of fruit, vegetables, grains and meats.

In one embodiment, a near-infrared or SWIR super-continuum (SC) source may be used as the light source for spectroscopy, active remote sensing, or hyper-spectral imaging. One embodiment of the SWIR light source may be an all-fiber integrated SWIR SC source, which leverages the mature technologies from the telecommunications and fiber optics industry. Exemplary fiber-based super-continuum sources may emit light in the near-infrared or SWIR between approximately 1.4-1.8 microns, 2-2.5 microns, 1.4-2.4 microns, 1-1.8 microns, or any number of other bands. In particular embodiments, the detection system may be a dispersive spectrometer, a Fourier transform infrared spectrometer, or a hyper-spectral imaging detector or camera. In addition, reflection or diffuse reflection light spectroscopy may be implemented using the SWIR light source, where the spectral reflectance can be the ratio of reflected energy to incident energy as a function of wavelength.

In one embodiment, a measurement system includes a light source configured to generate an output optical beam comprising one or more semiconductor sources configured to generate an input beam, one or more optical amplifiers configured to receive at least a portion of the input beam and to deliver an intermediate beam to an output end of the one or more optical amplifiers, and one or more optical fibers configured to receive at least a portion of the intermediate beam and to deliver at least the portion of the intermediate beam to a distal end of the one or more optical fibers to form a first optical beam. A nonlinear element is configured to receive at least a portion of the first optical beam and to broaden a spectrum associated with the at least a portion of the first optical beam to at least 10 nm through a nonlinear effect in the nonlinear element to form the output optical beam with an output beam broadened spectrum, wherein at least a portion of the output beam broadened spectrum comprises a short-wave infrared wavelength between approximately 1400 nanometers and approximately 2500 nanometers, and wherein at least a portion of the one or more fibers is a fused silica fiber with a core diameter less than approximately 400 microns. A measurement apparatus is configured to receive a received portion of the output optical beam and to deliver a delivered portion of the output optical beam to a sample for a non-destructive and non-contact measurement, wherein the delivered portion of the output optical beam is configured to generate a spectroscopy output beam from the sample. A receiver is configured to receive at least a portion of the spectroscopy output beam having a bandwidth of at least 10 nanometers and to process the portion of the spectroscopy output beam to generate an output signal, and wherein at least a part of the delivered portion of the output optical beam is at least partially transmitting through a packaging material covering at least a part of the sample, and wherein the output signal is based on a chemical composition of the sample.

In another embodiment, a measurement system includes a light source configured to generate an output optical beam comprising a plurality of semiconductor sources configured to generate an input optical beam, a multiplexer configured to receive at least a portion of the input optical beam and to form an intermediate optical beam, and one or more fibers configured to receive at least a portion of the intermediate optical beam and to form the output optical beam, wherein the output optical beam comprises one or more optical wavelengths. A measurement apparatus is configured to receive a received portion of the output optical beam and to deliver a delivered portion of the output optical beam to a sample, wherein the delivered portion of the output optical beam is configured to generate a spectroscopy output beam from the sample. A receiver is configured to receive at least a portion of the spectroscopy output beam and to process the portion of the spectroscopy output beam to generate an output signal, wherein the receiver comprises a Fourier transform infrared (FTIR) spectrometer or a dispersive spectrometer, and wherein at least a part of the delivered portion of the output optical beam is at least partially transmitting through a packaging material covering at least a part of the sample.

In yet another embodiment, a method of measuring includes generating an output optical beam comprising generating an input optical beam from a plurality of semiconductor sources, multiplexing at least a portion of the input optical beam and forming an intermediate optical beam, and guiding at least a portion of the intermediate optical beam and forming the output optical beam, wherein the output optical beam comprises one or more optical wavelengths. The method may also include receiving a received portion of the output optical beam and delivering a delivered portion of the output optical beam to a sample, wherein the sample comprises an organic compound with an overtone or combinational absorption band in the wavelength range between approximately 1 micron and approximately 2.5 microns. The method may further include generating a spectroscopy output beam having a bandwidth of at least 10 nanometers from the sample using a Fourier transform infrared (FTIR) spectrometer or a dispersive spectrometer, receiving at least a portion of the spectroscopy output beam, and processing the portion of the spectroscopy output beam and generating an output signal.

BRIEF DESCRIPTION OF THE DRAWINGS

For a more complete understanding of the present disclosure, and for further features and advantages thereof, reference is now made to the following description taken in conjunction with the accompanying drawings, in which:

FIG. 9 lists possible band assignments for the various spectral features in pure heroin.

DETAILED DESCRIPTION

Figure 1:
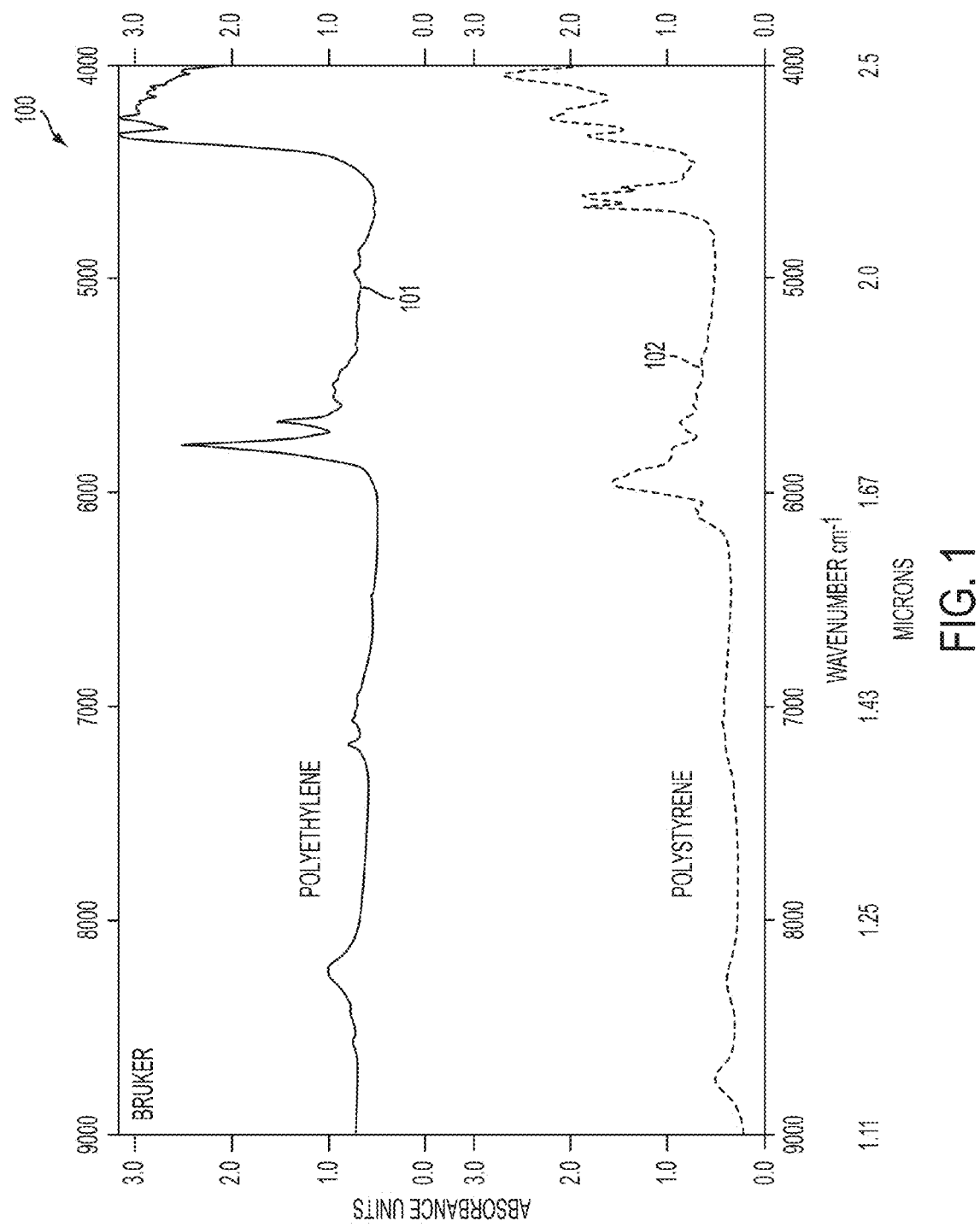
FIG. 1 shows the absorbance for two common plastics, polyethylene and polystyrene.

As required, detailed embodiments of the present disclosure are described herein; however, it is to be understood that the disclosed embodiments are merely exemplary of the disclosure that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

One advantage of optical systems is that they can perform non-contact, stand-off or remote sensing distance spectroscopy of various materials. As an example, optical systems can be used for identification of counterfeit drugs, detection of illicit drugs, or process control in the pharmaceutical industry, especially when the sensing is to be done at remote or stand-off distances in a non-contact, rapid manner. In general, the near-infrared region of the electromagnetic spectrum covers between approximately 0.7 microns (700 nm) to about 2.5 microns (2500 nm). However, it may also be advantageous to use just the short-wave infrared (SWIR) between approximately 1.4 microns (1400 nm) and about 2.5 microns (2500 nm). One reason for preferring the SWIR over the entire NIR may be to operate in the so-called "eye safe" window, which corresponds to wavelengths longer than about 1400 nm. Therefore, for the remainder of the disclosure the SWIR will be used for illustrative purposes. However, it should be clear that the discussion that follows could also apply to using the near infrared—NIR—wavelength range, or other wavelength bands.

In particular, wavelengths in the eye safe window may not transmit down to the retina of the eye, and therefore, these wavelengths may be less likely to create permanent eye damage from inadvertent exposure. The near-infrared wavelengths have the potential to be dangerous, because the eye cannot see the wavelengths (as it can in the visible), yet they can penetrate and cause damage to the eye. Even if a practitioner is not looking directly at the laser beam, the practitioner's eyes may receive stray light from a reflection or scattering some surface. Hence, it can always be a good practice to use eye protection when working around lasers. Since wavelengths longer than about 1400 nm are substantially not transmitted to the retina or substantially absorbed in the retina, this wavelength range is known as the eye safe window. For wavelengths longer than 1400 nm, in general only the cornea of the eye may receive or absorb the light radiation.

The SWIR wavelength range may be particularly valuable for identifying materials based on their chemical composition because the wavelength range comprises overtones and combination bands for numerous chemical bonds. For example, in the SWIR numerous hydro-carbon chemical compounds have overtone and combinational bands, along with oxygen-hydrogen and carbon-oxygen compounds. Thus, gases, liquids and solids that comprise these chemical compounds may exhibit spectral features in the SWIR wavelength range. In a particular embodiment, the spectra of organic compounds may be dominated by the C—H stretch. The C—H stretch fundamental occurs near 3.4 microns, the first overtone is near 1.7 microns, and a combination band occurs near 2.3 microns.

One embodiment of remote sensing that is used to identify and classify various materials is so-called "hyper-spectral imaging." Hyper-spectral sensors may collect information as a set of images, where each image represents a range of wavelengths over a spectral band. Hyper-spectral imaging may deal with imaging narrow spectral bands over an approximately continuous spectral range. As an example, in hyper-spectral imaging a lamp may be used as the light source. However, the incoherent light from a lamp may spatially diffract rapidly, thereby making it difficult to perform spectroscopy at stand-off distances or remote distances. Therefore, it would be advantageous to have a broadband light source covering the SWIR that may be used in place of a lamp to identify or classify materials in remote sensing or stand-off detection applications.

As used throughout this document, the term "couple" and or "coupled" refers to any direct or indirect communication between two or more elements, whether or not those elements are physically connected to one another. As used throughout this disclosure, the term "spectroscopy" means that a tissue or sample is inspected by comparing different features, such as wavelength (or frequency), spatial location, transmission, absorption, reflectivity, scattering, fluorescence, refractive index, or opacity. In one embodiment, "spectroscopy" may mean that the wavelength of the light source is varied, and the transmission, absorption, fluorescence, or reflectivity of the tissue or sample is measured as a function of wavelength. In another embodiment, "spectroscopy" may mean that the wavelength dependence of the transmission, absorption, fluorescence or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this document, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or light-pipe. In one embodiment, the gain fiber may be doped with rare earth material, such as ytterbium, erbium, and/or thulium. In another embodiment, the mid-infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam is coupled to a gain medium to excite the gain medium, which in turn may amplify another input optical signal or beam. In one particular example, the gain medium may be a doped fiber, such as a fiber doped with ytterbium, erbium and/or thulium. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and or "supercontinuum" and or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth of at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, parametric amplification, the Raman effect, modulational instability, and self-phase modulation.

As used throughout this disclosure, the terms "optical light" and or "optical beam" and or "light beam" refer to photons or light transmitted to a particular location in space. The "optical light" and or "optical beam" and or "light beam" may be modulated or unmodulated, which also means that they may or may not contain information. In one embodiment, the "optical light" and or "optical beam" and or "light beam" may originate from a fiber, a fiber laser, a laser, a light emitting diode, a lamp, a pump laser, or a light source.

As used throughout this disclosure, the term "remote sensing" may include the measuring of properties of an object from a distance, without physically sampling the object, for example by detection of the interactions of the object with an electromagnetic field. In one embodiment, the electromagnetic field may be in the optical wavelength range, including the infrared or SWIR. One particular form of remote sensing may be stand-off detection, which may range exemplary from non-contact up to hundreds of meters away.

Identification of Counterfeit Drugs

Pharmaceutical counterfeiting is a growing and significant issue for the healthcare community as well as the pharmaceutical industry worldwide. As a result of counterfeiting, users may be threatened by substandard drug quality or harmful ingredients, and legitimate companies may lose significant revenues. The definition for "counterfeit drug" by the World Health Organization was as follows: "A counterfeit medicine is one which is deliberately and fraudulently mislabeled with respect to identity and/or source. Counterfeiting can apply to both branded and generic products and counterfeit products may include products with the correct ingredients or with the wrong ingredients, without active ingredients, with insufficient active ingredient or with fake packaging." Later this definition was slightly modified, "Counterfeiting in relation to medicinal products means the deliberate and fraudulent mislabeling with respect to the identity, composition and/or source of a finished medicinal product, or ingredient for the preparation of a medicinal product."

A rapid screening technique such as near-infrared or SWIR spectroscopy could aid in the search for and identification of counterfeit drugs. In particular, using a non-lamp based light source could lead to contact-free control and analysis of drugs. In a particular embodiment, remote sensing, stand-off detection, or hyper-spectral imaging may be used for process control or counterfeit drug identification in a factory or manufacturing setting, or in a retail, wholesale, or warehouse setting. In one embodiment, the light source for remote sensing may direct the light beam toward the region of interest (e.g., conveyor belt, stocking shelves, boxes or cartons, etc), and the diffuse reflected light may then be measured using a detection system. Various kinds of SWIR light sources will be discussed later in this disclosure. The detection system may comprise, in one embodiment, a spectrometer followed by one or more detectors. In another embodiment, the detection system may be a dispersive element (examples include prisms, gratings, or other wavelength separators) followed by one or more detectors or detector arrays. In yet another embodiment, the detection system may comprise a Fourier transform infrared spectrometer. These are merely specific examples of the detection system, but combinations of these or other detection systems may also be used and are contemplated within the scope of this disclosure.

For monitoring drugs, the SWIR light source and the detection system could be used in transmission, reflection, fluorescence, or diffuse reflection. Also, different system configurations may also be used and are included in the scope of this disclosure. For example, the light source and detection system may be placed in a fixed location, and for reflection the light source and detectors may be close to one another, while for transmission the light source and detectors may be at different locations. The region of interest may be surveyed, and the light beam may also be scanned to cover an area larger than the light source beam. In yet another embodiment, the system could be placed on a vehicle such as an automobile or a truck, or the light source could be placed on one vehicle, while the detection system is on another vehicle. If the light source and detection system are compact and lightweight, they might even be carried by a person in the field, either in their hands or in a backpack.

Another advantage of using the near-infrared or SWIR is that most drug packaging materials are at least partially transparent in this wavelength range, so that drug compositions may be detected and identified through the packaging non-destructively. As an example, SWIR light could be used to see through plastics, since the signature for plastics can be subtracted off and there are large wavelength windows where the plastics are transparent. FIG. 1 illustrates the absorbance 100 for two common plastics: polyethylene 101 and polystyrene 102. Because of the hydro-carbon bonds, there are absorption features near 1.7 microns and 2.2-2.5 microns. In general, the absorption bands in the near infrared are due to overtones and combination bands for various functional group vibrations, including signals from C—H, O—H, C=O, N—H, —COOH, and aromatic C—H groups. It may be difficult to assign an absorption band to a specific functional group due to overlapping of several combinations and overtones. However, with advancements in computational power and chemometrics or multivariate analysis methods, complex systems may be better analyzed. In one embodiment, using software analysis tools the absorption spectrum may be converted to its second derivative equivalent. The spectral differences may permit a fast, accurate, non-destructive and reliable identification of materials. Although particular derivatives are discussed, other mathematical manipulations may be used in the analysis, and these other techniques are also intended to be covered by this disclosure.

Spectroscopy in the near-infrared or SWIR may be sensitive to both the chemical and physical nature of the sample composition and may be performed rapidly with minimal sample preparation. For example, near-infrared or SWIR spectroscopy may be used to study the homogeneity of powder samples, particle size determinations, product composition, the determination of the concentrations and distribution of components in solid tablets and content uniformity, among other applications. In yet other embodiments, applications include tablet identification, determination of moisture, residual solvents, active ingredient potency, the study of blending operations, and the detection of capsule tampering.

Figure 2:
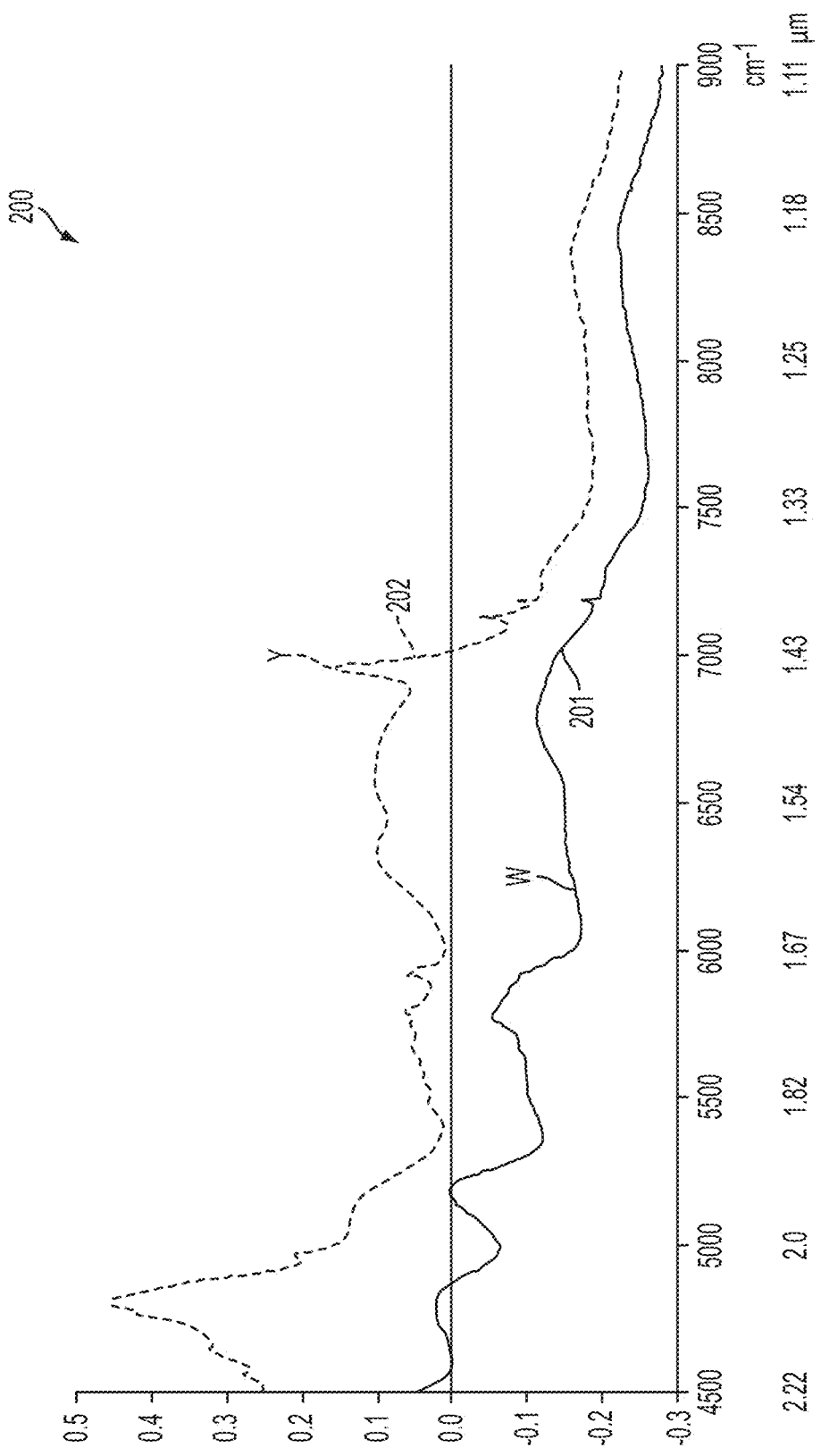
FIG. 2 illustrates one example of the difference in near-infrared spectrum between an authentic tablet and a counterfeit tablet.

FIG. 2 illustrates one example of the difference in near-infrared spectrum 200 between an authentic tablet and a counterfeit tablet. Two grades of film coated tablets comprising drugs were investigated: curve 201 is the genuine drug, while 202 is a counterfeit drug. These two grades of capsules have noticeably different contents, and the differences are apparent in the near-infrared or SWIR spectra. In some cases the differences may not be as distinct. For these cases, more signal processing may be necessary to distinguish between samples.

Figure 3:
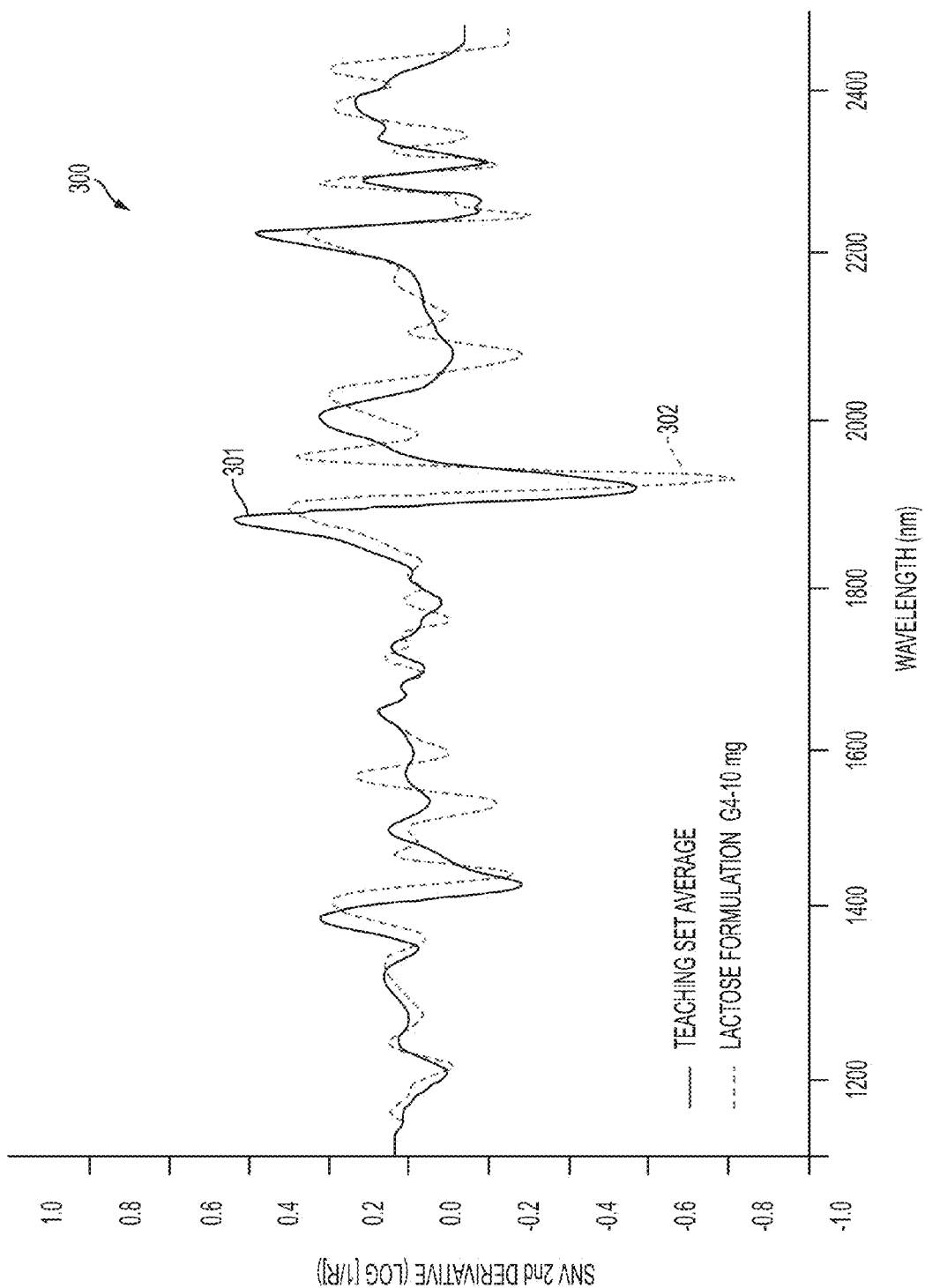
FIG. 3 shows the second derivative of the spectral comparison of Prozac and a similarly formulated generic.

In another embodiment, it may be advantageous to take a first, second or higher order derivative to elucidate the difference between real and counterfeit drugs. For example, FIG. 3 shows the second derivative 300 of the spectral comparison of Prozac 301 and a similarly formulated generic 302, which had a fluoxetine hydrochloride (10 mg). Although the reflectance curves from the two samples are close and, therefore, difficult to distinguish, the second derivative of the data helps to bring out the differences more clearly. Although a second derivative is used in this example, any number of signal processing algorithms and methods may be used, and these are also intended to be covered by this disclosure. For example, partial least square algorithms, multivariate data analysis, principal component analysis, or chemometric software may be implemented without departing from the scope of this disclosure.

In yet another embodiment, near-infrared or SWIR spectroscopy may be used to measure and calibrate various pharmaceutical formulations based on the active pharmaceutical ingredients and excipients. An excipient may be a pharmacologically inactive substance used as a carrier for the active ingredients of a medication. In some cases, the active substance may not be easily administered and/or absorbed by the human body; in such cases the active ingredient may be dissolved into or mixed with an excipient. Also, excipients are also sometimes used to bulk up formulations that contain very potent active ingredients, to allow for convenient and accurate dosage. In addition to their use in the single-dosage quantity, excipients can be used in the manufacturing process to aid in the handling of the active substance concerned.

Figure 4:
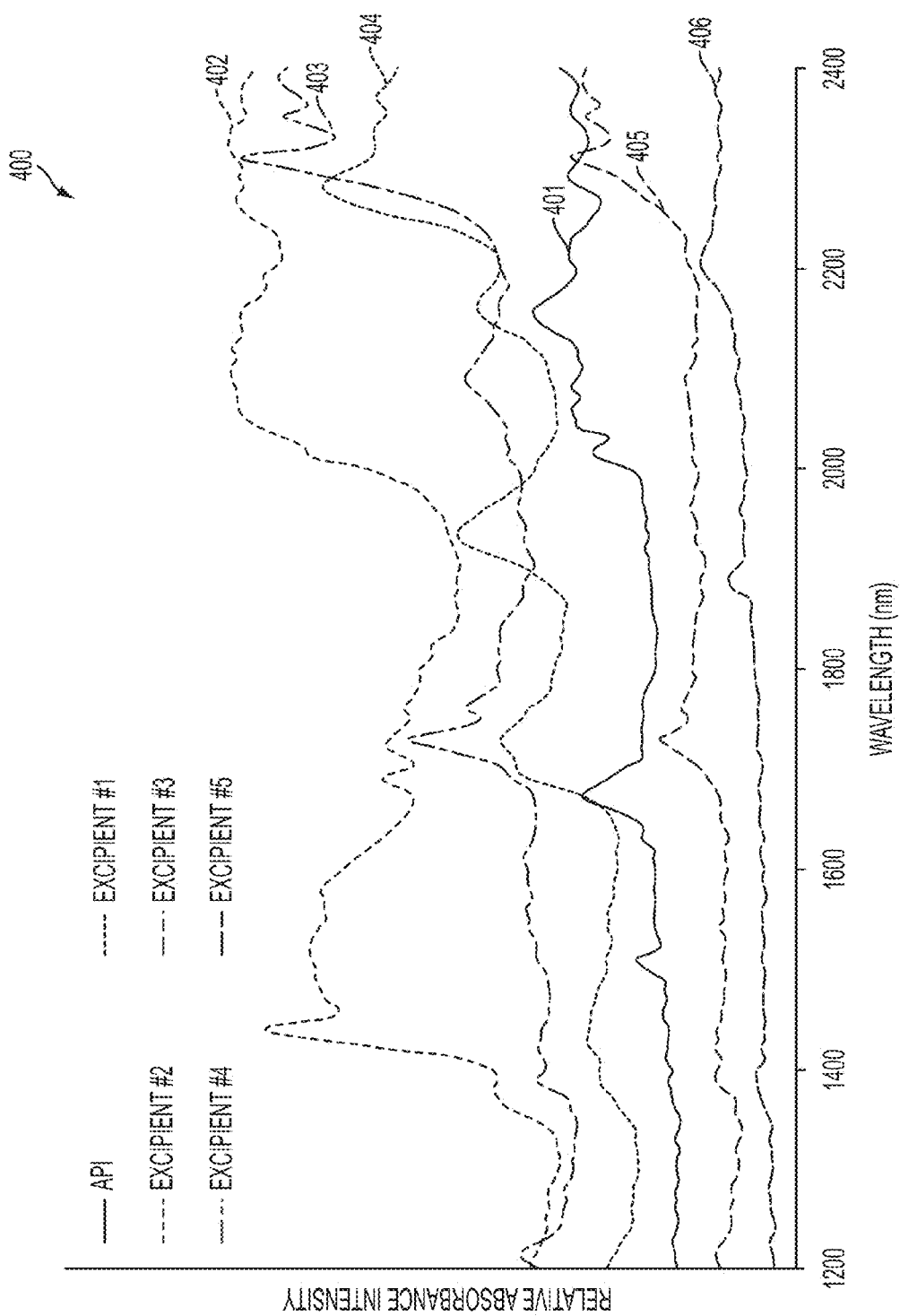
FIG. 4 illustrates an example of the near infrared spectra for different pure components of a studied drug.

FIG. 4 shows an example of the near-infrared spectra 400 for different pure components of a studied drug. The spectrum for the active pharmaceutical ingredient (API) 401 is plotted, along with the spectra for five different excipients 402, 403, 404, 405 and 406. Each spectrum has been baseline shifted to avoid overlapping. The near-infrared spectra have been obtained by averaging the spectra of each pixel of an area of a hyper-spectral image. As FIG. 4 shows, each of the chemical compositions have a distinct spectrum, and the composition of a drug may be decomposed into its constitutive ingredients. These are just some examples of how near-infrared or SWIR spectroscopy may be applied to counterfeit drug detection, but other methods and analysis techniques may also be used without departing from the scope of this disclosure. As one other example, once the active pharmaceutical ingredient and the excipients spectral distribution of a drug formulation are understood, feedback may be provided of this information to the drug development stages.

Rapid Screening for Illicit Drugs

Figure 5:
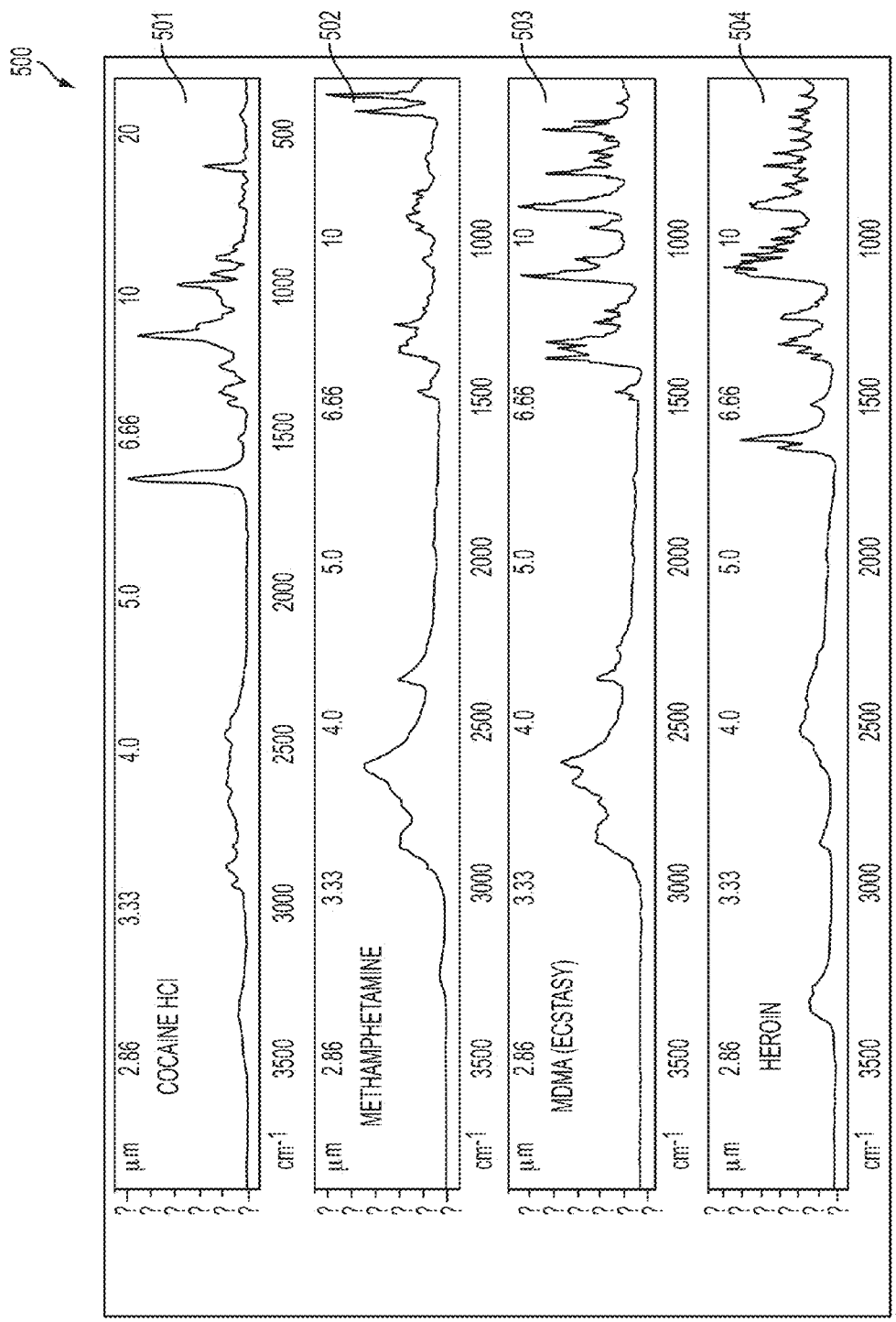
FIG. 5 shows the mid-wave infrared and long-wave infrared absorption spectra for various illicit drugs.

Thus, FIGS. 2-4 show that near-infrared or SWIR spectroscopy may be used to identify counterfeit drugs. More generally, various materials including illicit drugs, explosives, fertilizers, vegetation, and paints have features in the near-infrared and SWIR that can be used to identify the various samples, and these applications are also intended to be within the scope of this disclosure. Although stronger features may be found in the mid-infrared, the near-infrared may be easier to measure due to higher quality detection systems, more mature fiber optics and light sources, and transmission through atmospheric transmission windows. Because of these distinct spectral signatures, these materials could also be detected using active remote sensing, hyper-spectral imaging, or near-infrared or SWIR spectroscopy. As just another example, illicit drugs may be detectable using remote sensing, hyper-spectral imaging, or near-infrared spectroscopy. FIG. 5 shows the mid-wave infrared and long-wave infrared absorption spectra 500 for various illicit drugs. The absorbance for cocaine 501, methamphetamine 502, MDMA (ecstasy) 503, and heroin 504 are plotted versus wavelength from approximately 2.5-20 microns. Although the fundamental resonances for these drugs may lie in the longer wavelength regions, there are corresponding overtones and combination bands in the SWIR and near-infrared wavelength range. Therefore, the active remote sensing, hyper-spectral imaging, or near-infrared or SWIR spectroscopy techniques described herein may also be applicable to detecting illicit drugs from aircraft, vehicles, or hand held devices.

Figure 6:
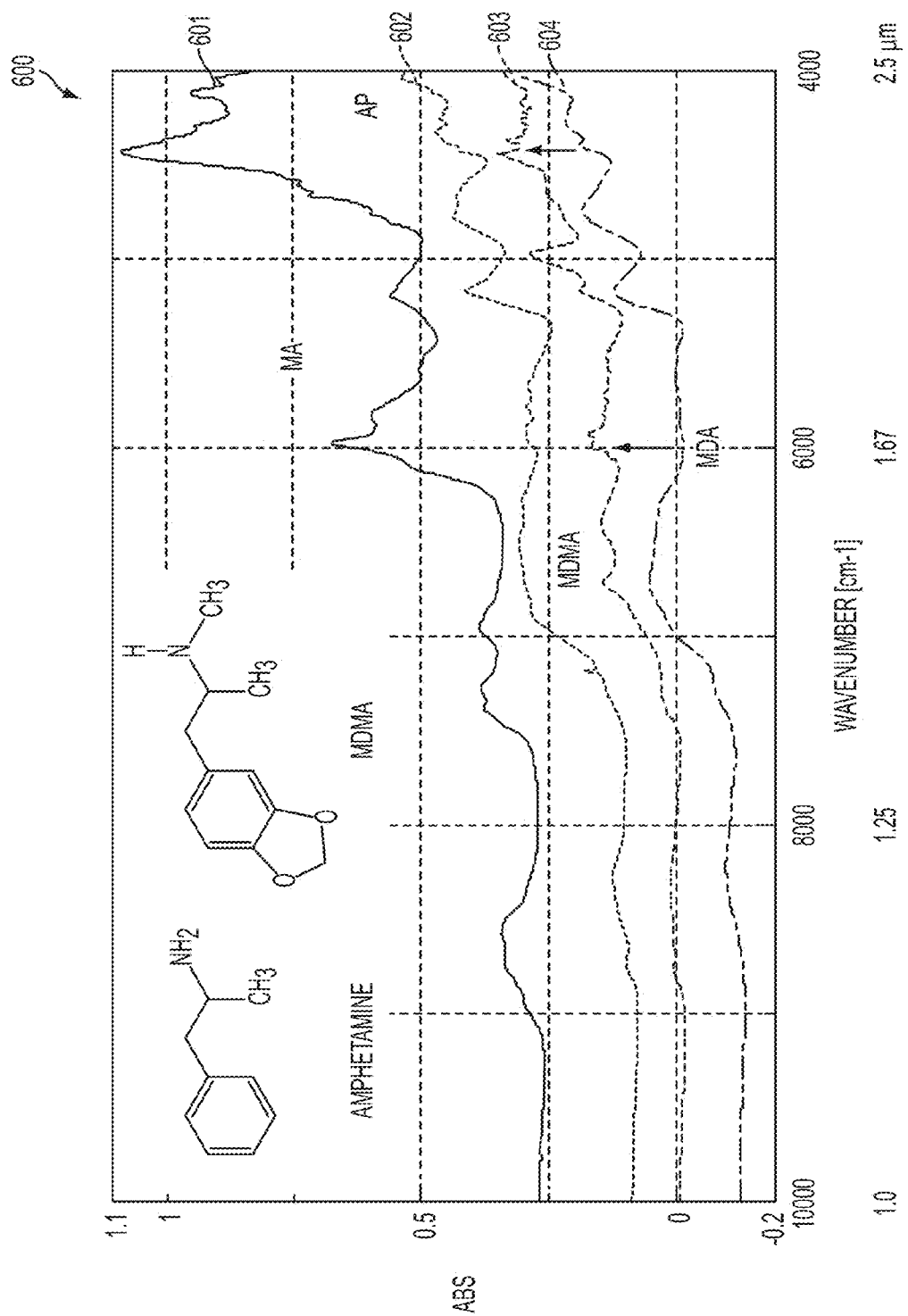
FIG. 6 shows the absorbance versus wavelength in the near-infrared region for four classes of illegal drugs.

The diffuse reflectance technique may be useful with near-infrared or SWIR spectroscopy for rapid identification of illegal drugs due to simple handling and simple use of a search data library created using near-infrared diffuse reflectance. For instance, FIG. 6 illustrates the absorbance 600 versus wavelength in the near-infrared region for four classes of illegal drugs. In particular, the spectra are shown for methamphetamine (MA) 601, amphetamine (AP) 602, MDMA (street name: ecstasy) 603, and MDA (street name: the love drug) 604. Each of the illegal drugs have unique spectral features in the near-infrared and SWIR. Also, comparing the mid-infrared spectrum for MDMA (503 in FIG. 5) with the near-infrared spectrum for MDMA (603 in FIG. 6), it seems clear that the near-infrared region shows overtones and combination bands that should be discernible. Referring to FIG. 6, sample identification may be accomplished by using the region (indicated by the arrows) where the spectral absorptions may provide specific peaks depending on the drug component.

Figure 7:
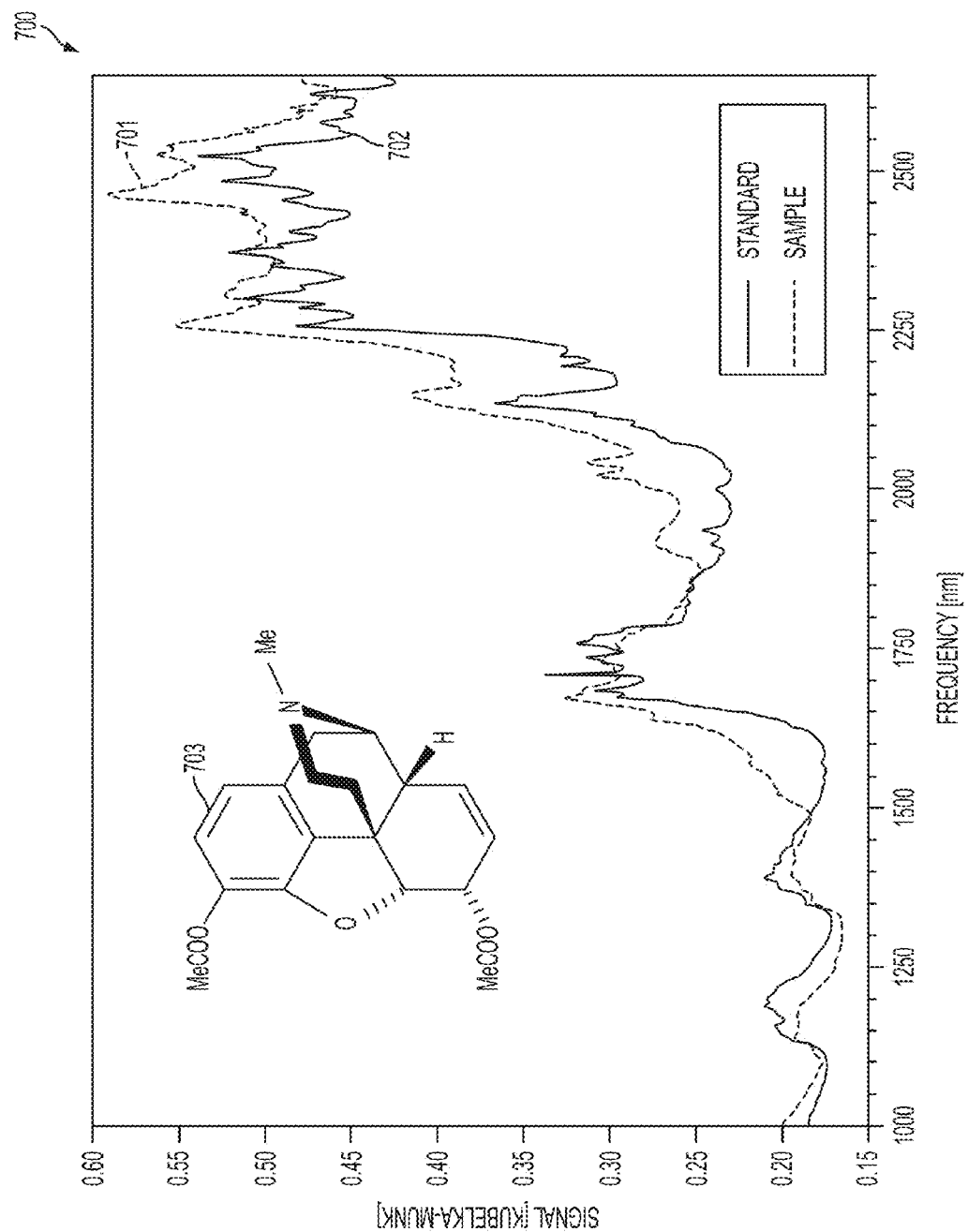
FIG. 7 illustrates the diffuse reflectance near-infrared spectrum of heroin samples.

In another embodiment, FIG. 7 shows the diffuse reflectance near-infrared spectrum 700 of heroin samples. Heroin, the 3,6-diacetyl derivative of morphine (hence diacetyl-morphine) is an opiate drug synthesized from morphine, which is usually a naturally occurring substance extracted from the seedpod of certain varieties of poppy plants. In particular, 701 is the near-infrared spectrum for an illicit street drug sample, while 702 is the spectra for a pure heroin standard. The difference between the spectra may arise at least in part from cutting agents. The inset 703 shows the molecular structure for heroin. As in the other examples, the absorption in the near-infrared range is caused by overtone and combination vibrations of O—H, C—H, N—H and C=O groups, which exhibit their fundamental molecular stretching and bending absorption in the mid-infrared range (c.f., the mid-infrared spectrum for heroin is shown 504 in FIG. 5). These overtone and combination bands do not behave in a simple way, making the near-infrared spectra complex and harder to directly interpret. Also, although the near-infrared signatures may be weaker in magnitude, they are probably easier to detect in the near-infrared, and the sample preparation may also be much simpler in the near-infrared. Moreover, for remote sensing, the near-infrared may be preferable because of atmospheric transmission windows between approximately 1.4-1.8 microns and 2-2.5 microns.

Figure 8:
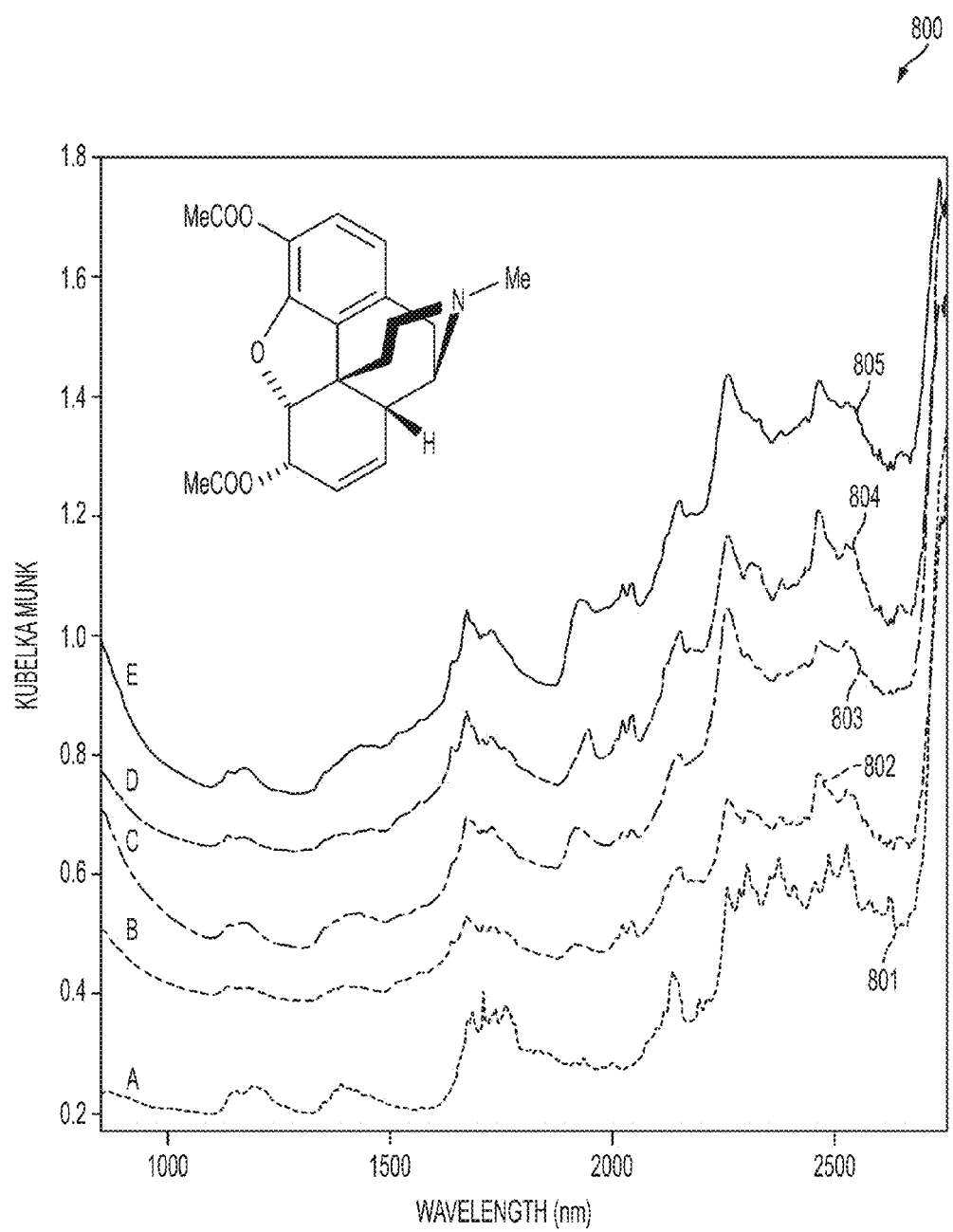
FIG. 8 illustrates the diffuse reflectance near-infrared spectra of different seized illicit drugs containing heroin of different concentrations, along with the spectrum for pure heroin.

Pure heroin may be a white powder with a bitter taste that is rarely sold on the streets, while illicit heroin may be a powder varying in color from white to dark brown due to impurities left from the manufacturing process or the presence of additives. The purity of street heroin may also vary widely, as the drug can be mixed with other white powders. The impurity of the drug may often make it difficult to gauge the strength of the dosage, which runs the risk of overdose. One nice feature of near-infrared or SWIR spectroscopy is that the technique may be used in a non-destructive, non-contact manner to determine rapidly the concentration of compounds present in complex samples at percentage levels with very little sample preparation. In a particular embodiment, FIG. 8 illustrates the diffuse reflectance near-infrared spectra 800 of different seized illicit drugs containing heroin (between 10.7 and 21.8%) compared with the spectrum of pure heroin 801. Curve 802 is for 21.8% by weight, curve 803 is 13.2% by weight, curve 804 is 17% by weight, and curve 805 is 10.7% by weight of heroin. The spectra have been shifted along the vertical axis to better illustrate the differences.

Although quite complex in the near-infrared, it may be possible to identify from the pure heroin near-infrared spectrum (801 in FIG. 8 or 702 in FIG. 7) the main wavelengths related to the most common functional groups in heroin. For example, FIG. 9 lists possible band assignments 900 for the various spectral features in pure heroin. As can be seen from FIG. 9, the absorption in the near-infrared may be mainly due to overtone and combination bands associated with O—H, C—H, N—H and C=O groups.

Figure 10:
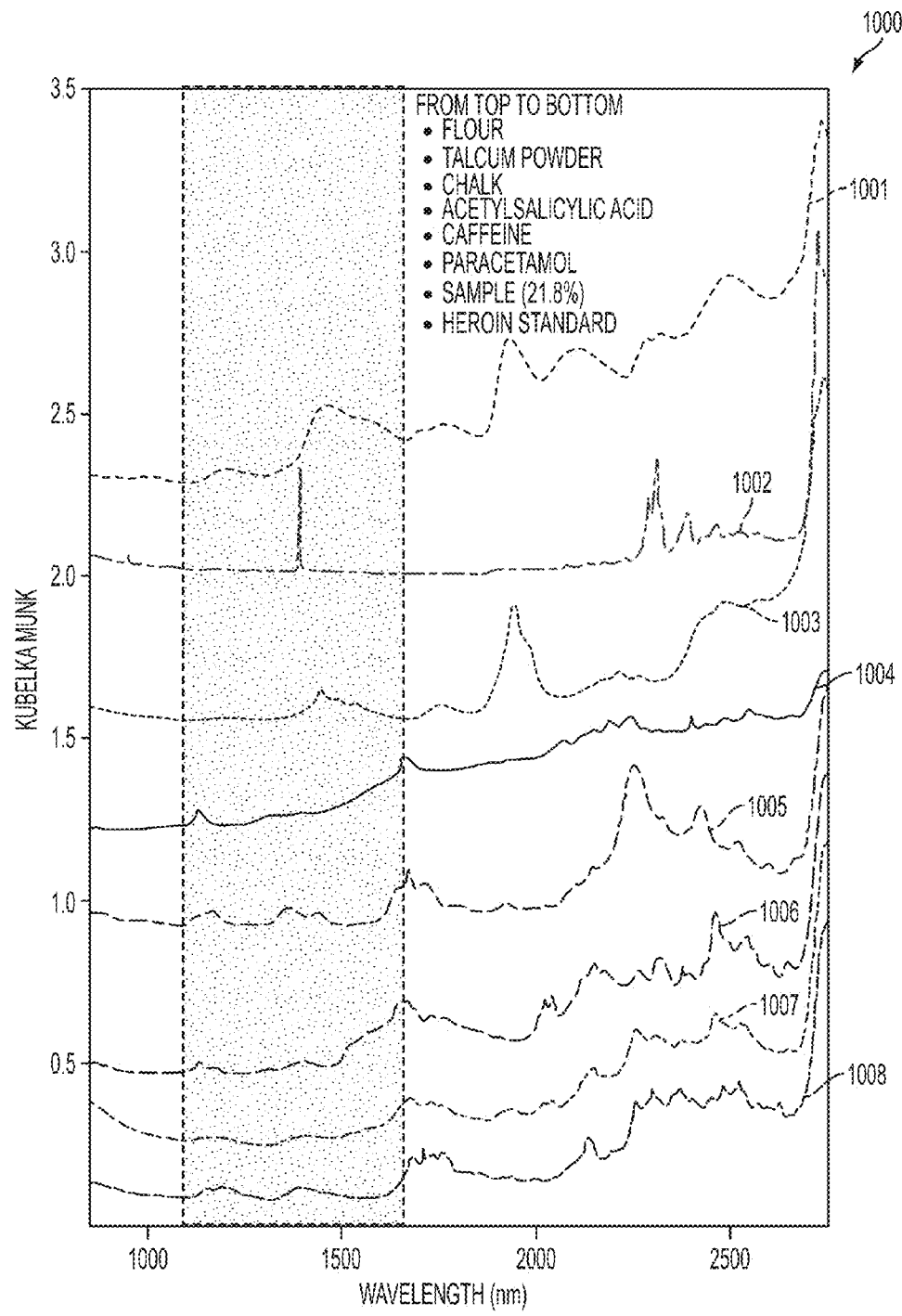
FIG. 10 shows the diffuse reflectance near-infrared spectra of different compounds that may be frequently employed as cutting agents.

As can be appreciated from FIG. 8, there may be significant differences between the spectrum of pure heroin and sample spectra. These differences may be due to the presence of different compounds used as cutting agents, which can affect the shape and intensity of the near-infrared signals. FIG. 10 illustrates the diffuse reflectance near-infrared spectra 1000 of different compounds that may be frequently employed as cutting agents. In the bottom of FIG. 10 are shown the spectra 1008 for pure heroin and the spectra 1007 for a seized illicit street drug sample comprising 21.8% of heroin. The spectra for various cutting agents include: 1001 for flour, 1002 for talcum powder, 1003 for chalk, 1004 for acetylsalicylic acid, 1005 for caffeine, and 1006 for paracetamol. Thus, near-infrared or SWIR spectroscopy may be used to work back to the composition of an unknown drug. Although particular examples of counterfeit and illicit drugs have been described, the near-infrared or SWIR spectroscopy (including diffuse reflectance, reflectance, fluorescence or transmission) may also be applied to the identification of other drugs and substances without departing from the scope of this disclosure. This spectroscopy may be used non-destructively and non-contact over stand-off distances or in remote sensing distances, whether from an airborne, vehicle, hand-held, or stationary platform.

Process Analytical Technology (PAT)

One definition of process analytical technology, PAT, is "a system for designing, analyzing and controlling manufacturing through timely evaluations (i.e., during processing) of significant quality and performance attributes of raw and in-process materials and processes, with the goal of ensuring final product quality." Near-infrared or SWIR spectroscopy may have applications in the PAT of the pharmaceutical industry by providing, for example, quantitative analysis of multiple components in a sample and in pack quantification of drugs in formulation, as well as quality of a drug and quality control of complex excipients used in formulation. The PAT process may benefit from near-infrared or SWIR spectroscopy for some steps, such as: raw material identification, active pharmaceutical ingredient applications, drying, granulation, blend uniformity and content uniformity. Some of the strengths of near-infrared or SWIR spectroscopy include: radiation has good penetration properties, and, thus, minimal sample preparation may be required; measurement results may be obtained rapidly, and simultaneous measurements may be obtained for several parameters; non-destructive methods with little or no chemical waste; and organic chemicals that comprise most pharmaceutical products have unique spectra in the near-infrared and SWIR ranges, for example.

Figure 11:
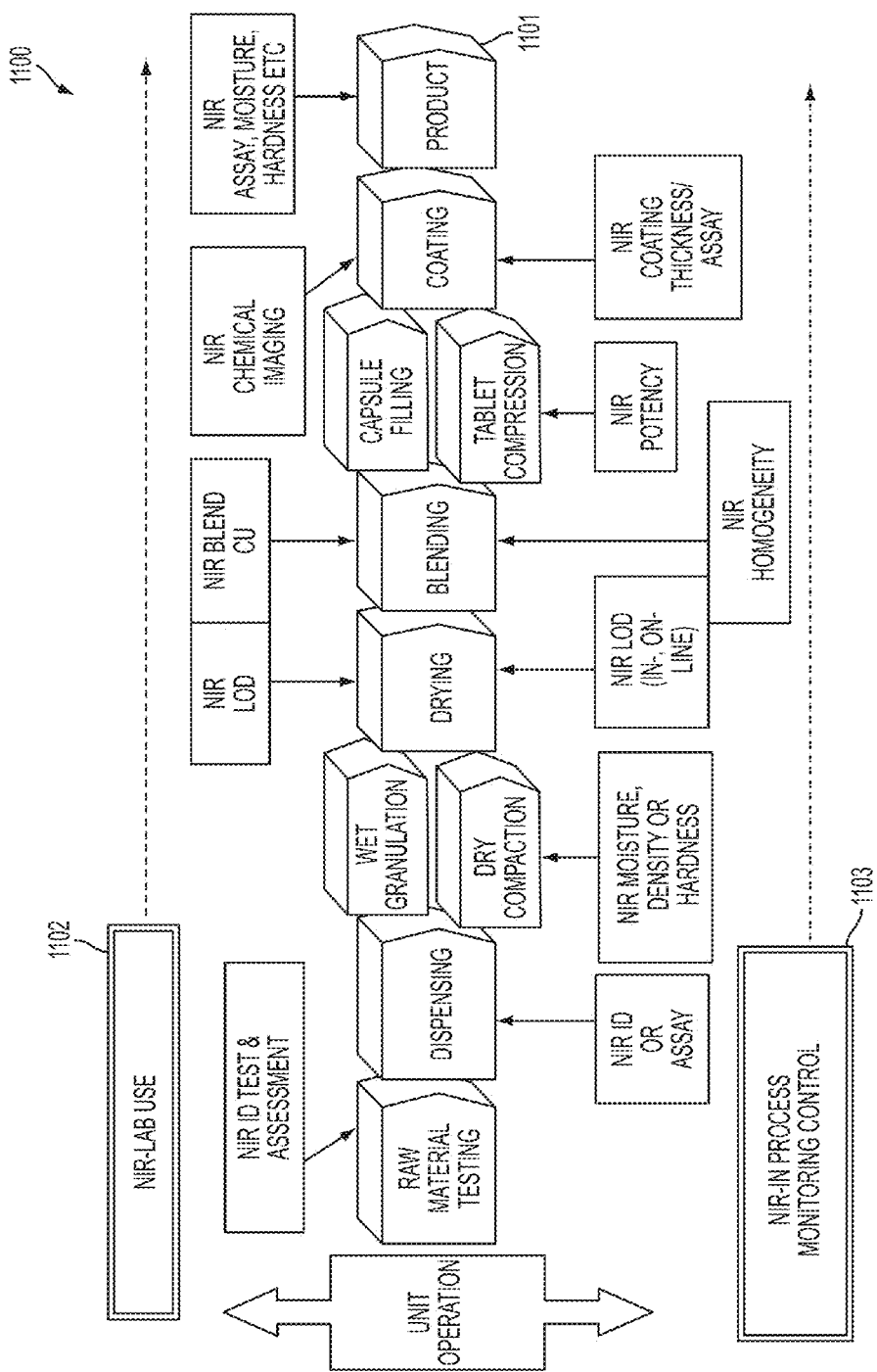
FIG. 11 provides one example of a flow-chart in the process analytical technology for the pharmaceutical industry.

FIG. 11 shows one example of a flow-chart 1100 in the PAT for the pharmaceutical industry. While the center shows the steps of the manufacturing process 1101, the top and bottom sides show where near-infrared spectroscopy could be applicable for lab use 1102 (top) or in process monitoring control 1103 (bottom). Indeed, near-infrared or SWIR spectroscopy has the potential to benefit almost every step in the manufacturing process. Just to provide a few examples of using near-infrared or SWIR spectroscopy in the PAT process, the raw material testing and blending process will be examined briefly.

Figure 12:
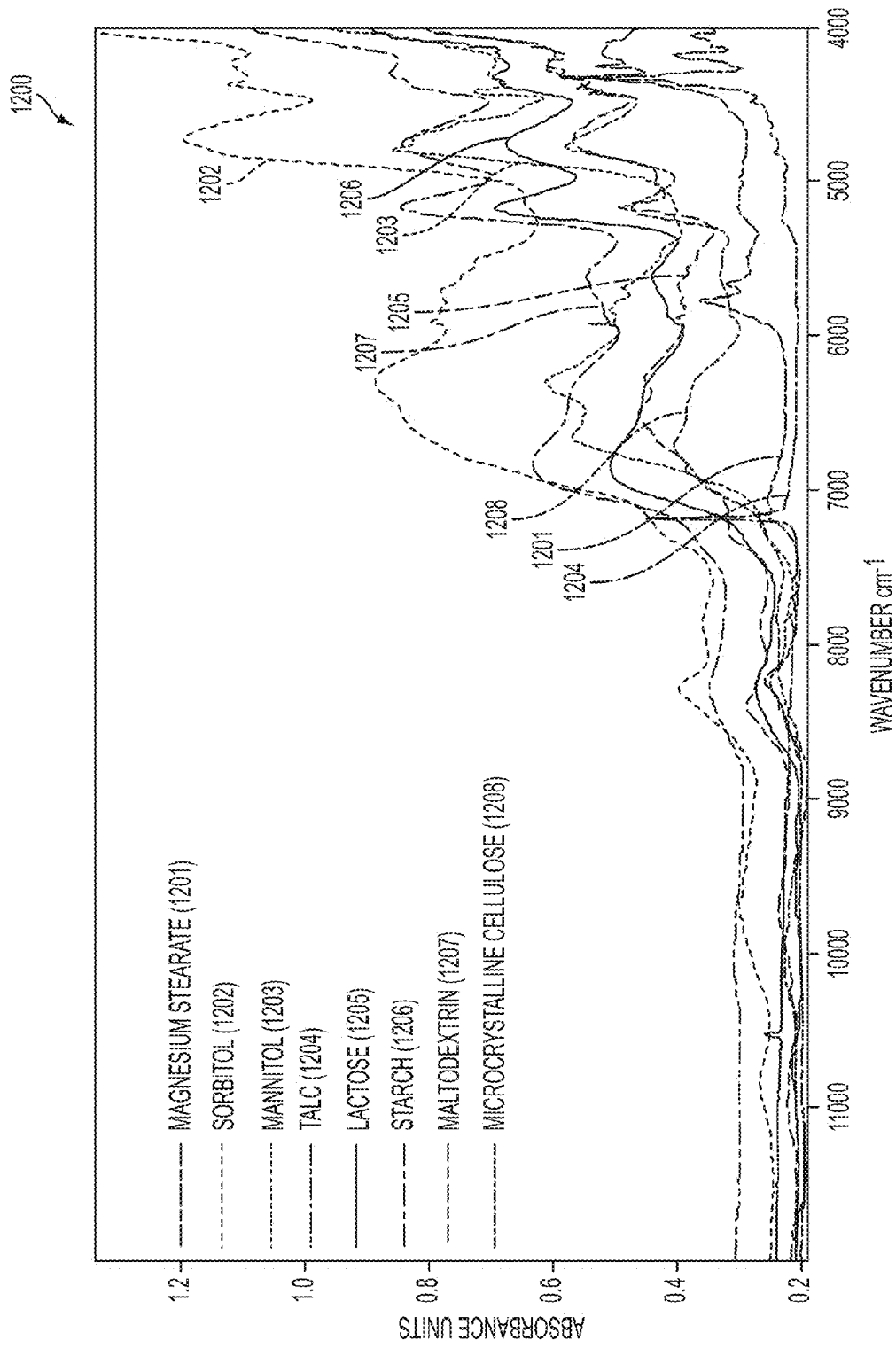
FIG. 12 illustrates the typical near-infrared spectra of a variety of excipients.

At the commencement of manufacture of a drug product, it may be required to identify the correct material and grade of the pharmaceutical excipients to be used in the formulation. FIG. 12 illustrates the typical near-infrared spectra 1200 for a variety of excipients. Included in the graph 1200 are spectra for: magnesium stearate 1201, sorbitol 1202, mannitol 1203, talc 1204, lactose 1205, starch 1206, maltodextrin 1207, and microcrystalline cellulose 1208. A suitable spectral database may be used to rapidly identify and qualify excipients. One nice aspect of the spectroscopy is that the near-infrared and SWIR are sensitive to both the physical and chemical characteristics of the samples.

Figure 13:
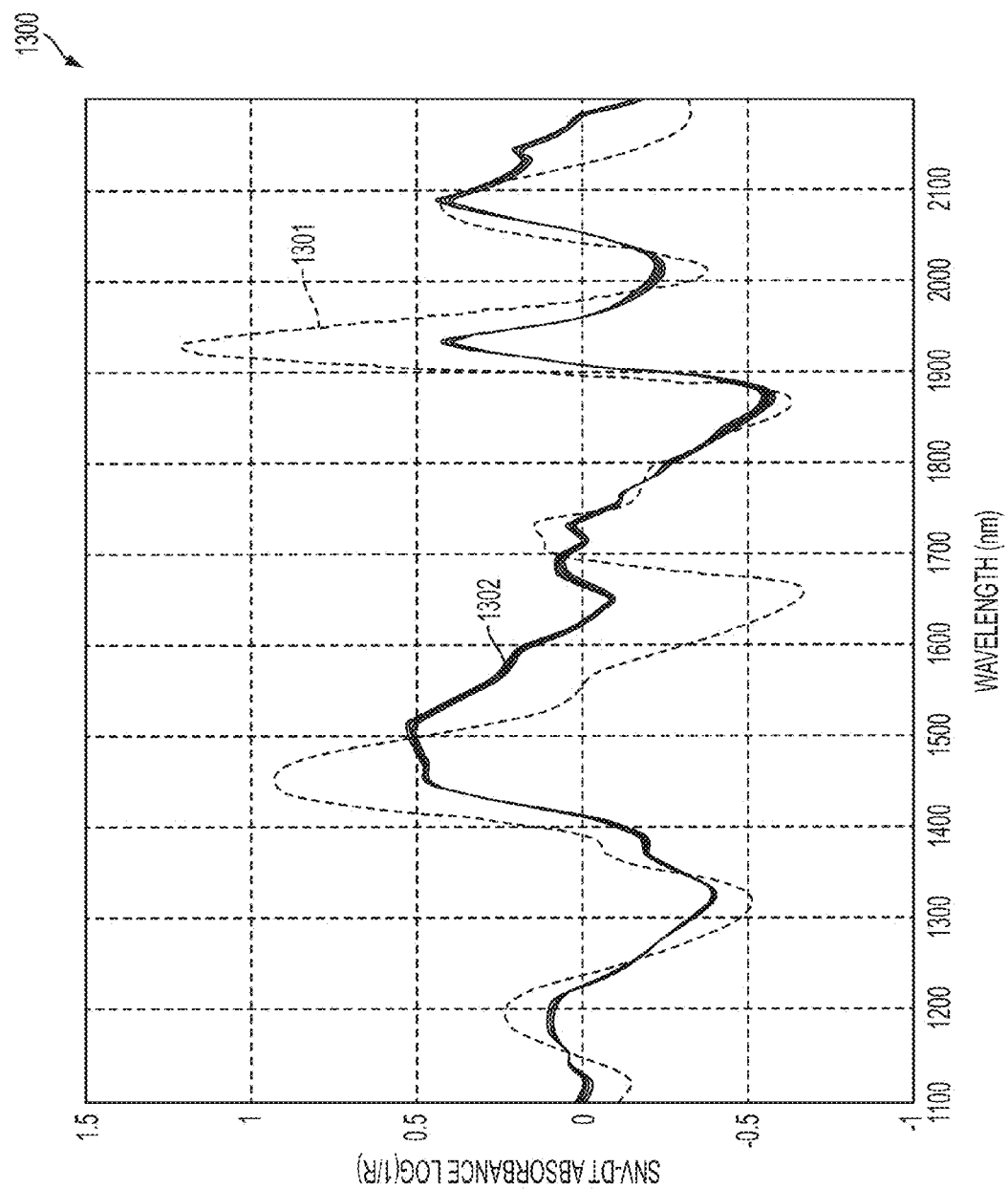
FIG. 13 exemplifies the absorbance from the blending process of a pharmaceutical compound.

One of the next steps in the manufacture of a dosage form is the blending together of the active component with the excipients to produce a homogeneous blend. In one embodiment, the near-infrared or SWIR spectroscopy apparatus may comprise a fiber-optic probe, which may, for example, interface with the blending vessel. For such a fiber-optic probe, near infrared or SWIR spectra may be collected in real-time from a blending process. FIG. 13 exemplifies the absorbance 1300 from the blending process. Although the initial spectra 1301 shows differences from the eventual spectra, as the process continues the blend converges to the final spectra 1302 and continues to overlap that spectra. Similar converging or overlapping spectra may also be used to check the product uniformity at the end of the process. The near-infrared spectra may be acquired in real-time; and, using appropriate data pre-processing and chemometric analysis, blend homogeneity plots may be derived, such as 1300.

One goal of the manufacturing process and PAT may be the concept of a "smart" manufacturing process, which may be a system or manufacturing operation responding to analytical data generated in real-time. Such a system may also have an in-built "artificial intelligence" as decisions may be made whether to continue a manufacturing operation. For example, with respect to the raw materials, integration of the quality measurement into smart manufacturing processes could be used to improve manufacturing operations by ensuring that the correct materials of the appropriate quality are used in the manufacture. Similarly, a smart blender would be under software control and would respond to the real-time spectral data collected.

Figure 14:
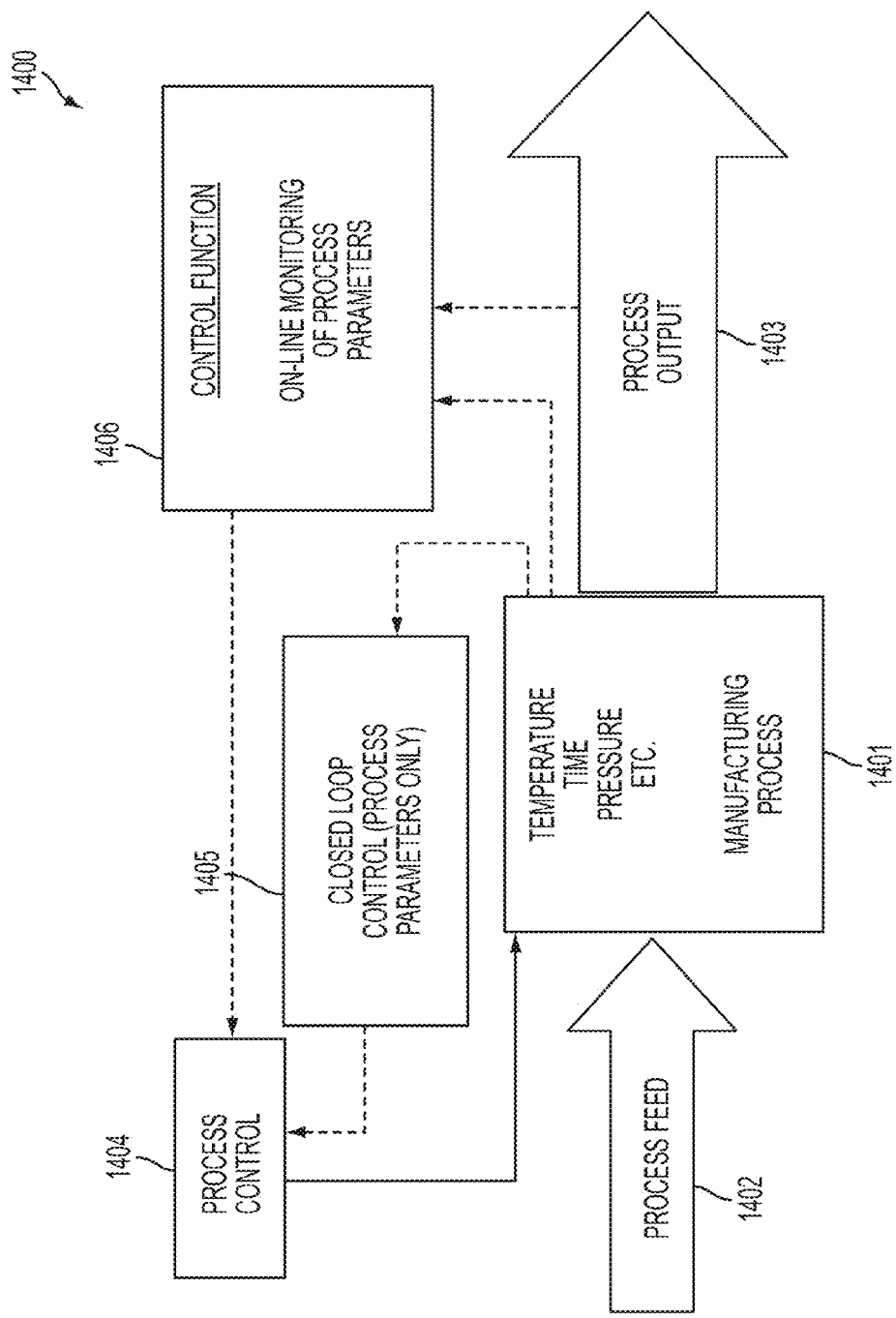
FIG. 14 shows what might be an eventual flow-chart of a smart manufacturing process.

FIG. 14 illustrates what might be an eventual flow-chart 1400 of a smart manufacturing process. The manufacturing process 1401 may have as input the process feed 1402 and result in a process output 1403. A process controller 1404 may at least partially control the manufacturing process 1401, and the controller 1404 may receive inputs from the closed loop control (process parameters) 1405 as well as the on-line monitoring of process parameters 1406. The feedback loops in the process could refine the manufacturing process 1401 and improve the quality of the process output 1403. These are particular embodiments of the use of near-infrared or SWIR spectroscopy in the PAT of the pharmaceutical industry, but other variations, combinations, and methods may also be used and are intended to be covered by this disclosure.

The discussion thus far has centered on use of near-infrared or SWIR spectroscopy in applications such as identification of counterfeit drugs, detection of illicit drugs, and pharmaceutical process control. Although drugs and pharmaceuticals are one example, many other fields and applications may also benefit from the use of near infrared or SWIR spectroscopy, and these may also be implemented without departing from the scope of this disclosure. As just another example, near-infrared or SWIR spectroscopy may also be used as an analytic tool for food quality and safety control. Applications in food safety and quality assessment include contaminant detection, defect identification, constituent analysis, and quality evaluation. The techniques described in this disclosure are particularly valuable when non-destructive testing is desired at stand-off or remote distances.

Figure 15A:
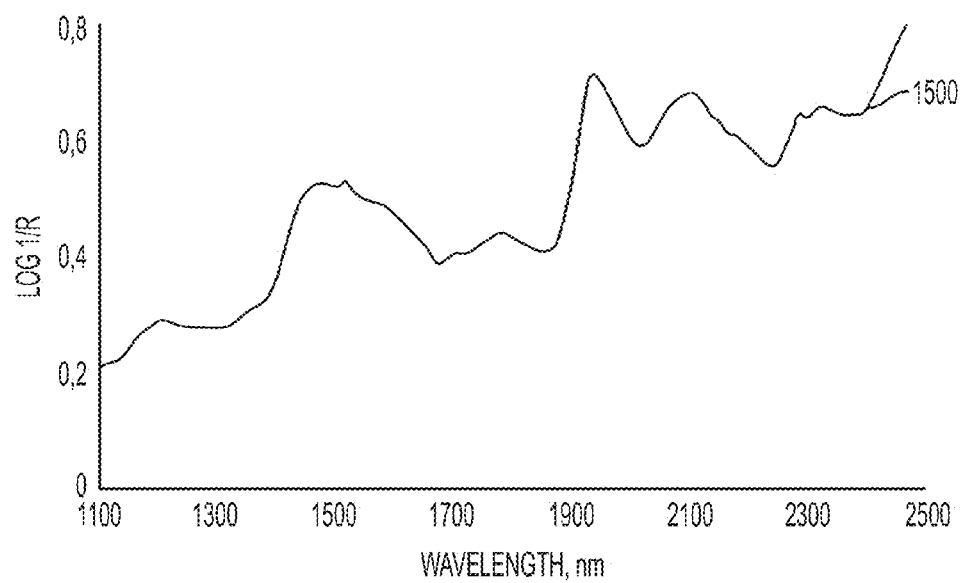
FIG. 15A illustrates the near-infrared reflectance spectrum of wheat flour.

In one example, near-infrared or SWIR spectroscopy may be used in cereal breeding. The breeding purposes may require knowledge on both composition and functional properties of grain, while the functionality of wheat grain is an issue for wheat breeders. Most of the wheat functionality parameters depend on the protein-proteinase complex of wheat grain, as well as the condition of the carbohydrate complex. FIG. 15A illustrates the near-infrared reflectance spectrum 1500 of wheat flour. Since these samples are complex in composition, several organic bonds involving hydrogen vibrate to produce overlapped spectral bands. Thus, the resulting spectrum 1500 appears like a wavy line without clearly defined features. Analytical methods based on this type of spectroscopy may have the potential to improve the quality of final cereal products by testing the products through the entire production process in the processing industry.

Figure 15B:
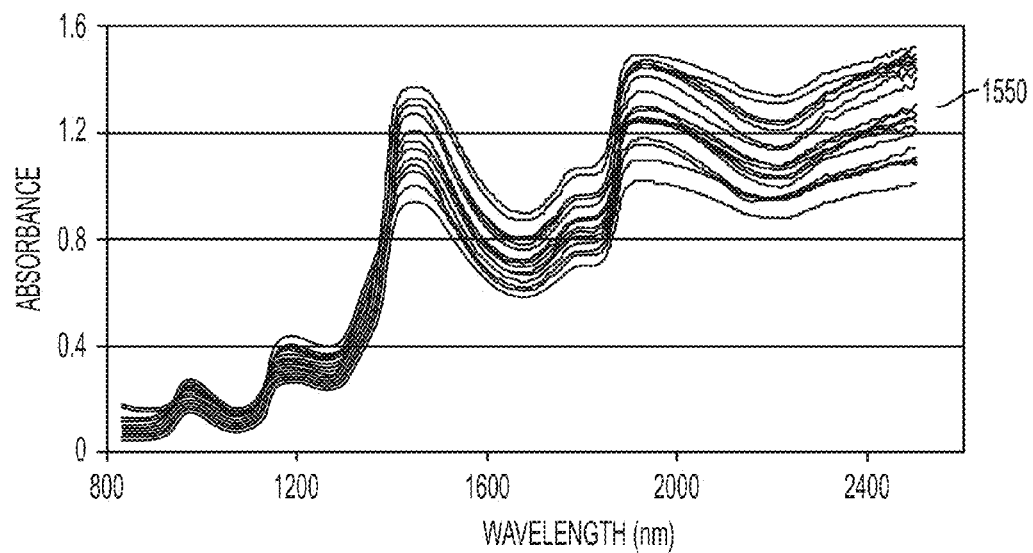
FIG. 15B shows the near-infrared absorbance spectra obtained in diffusion reflectance mode for a series of whole 'Hass' avocado fruit.

In yet another embodiment, near-infrared or SWIR spectroscopy may be used for the assessment of fruit and vegetable quality. Most commercial quality classification systems for fruit and vegetables are based on external features of the product, such as shape, color, size, weight and blemishes. However, the external appearance of most fruit is generally not an accurate guide to the internal eating quality of the fruit. As an example, for avocado fruit the external color is not a maturity characteristic, and its smell is too weak and appears later in its maturity stage. Analysis of the near-infrared or SWIR absorption spectra may provide qualitative and quantitative determination of many constituents and properties of horticulture produce, including oil, water, protein, pH, acidity, firmness, and soluble solids content or total soluble solids of fresh fruits. FIG. 15B shows the near-infrared absorbance spectra 1550 obtained in diffusion reflectance mode for a series of whole 'Hass' avocado fruit. Four oil absorption bands are near 2200-2400 nm ($CH_2$ stretch bend and combinations), with weaker absorption around 750 nm, 1200 nm, and 900-930 nm ranges. On the other hand, near 1300-1750 nm range may be useful for determining the protein and oil content. The 900-920 nm absorbance band may be useful for sugar determination. Although described in the context of grains, fruits, and vegetables, the near-infrared or SWIR spectroscopy may also be valuable for other food quality control and assessment, such as measuring the properties of meats. These and other applications also fall within the scope of this disclosure.

Detection Systems

The near-infrared or SWIR spectroscopy system, remote sensing system or hyper-spectral imaging system may be on an airborne platform, mounted on a vehicle, a stationary transmission or reflection set-up, or even held by a human for a compact system. For such a system, there are fundamentally two hardware parts: the transmitter or light source and the detection system. Between the two, perhaps in a transmission or reflection setting, may be the sample being tested or measured. Moreover, the output from the detection system may go to a computational system, comprising computers or other processing equipment. The output from the computational system may be displayed graphically as well as with numerical tables and perhaps an identification of the material composition. These are just some of the parts of the systems, but other elements may be added or be eliminated, and these modified configurations are also intended to be covered by this disclosure.

By use of an active illuminator, a number of advantages may be achieved. First, stand-off or remote distances may be achieved if a non-lamp system is used—i.e., if the beam does not rapidly diffract. Also, higher signal-to-noise ratios may be achieved. For example, one way to improve the signal-to-noise ratio would be to use modulation and lock-in techniques. In one embodiment, the light source may be modulated, and then the detection system would be synchronized with the light source. In a particular embodiment, the techniques from lock-in detection may be used, where narrow band filtering around the modulation frequency may be used to reject noise outside the modulation frequency. In another embodiment, change detection schemes may be used, where the detection system captures the signal with the light source on and with the light source off Again, for this system the light source may be modulated. Then, the signal with and without the light source is differenced. Change detection may help to identify objects that change in the field of view. In the following some exemplary detection systems are described.

In one embodiment, a SWIR camera or infrared camera system may be used to capture the images. The camera may include one or more lenses on the input, which may be adjustable. The focal plane assemblies may be made from mercury cadmium telluride material (HgCdTe), and the detectors may also include thermo-electric coolers. Alternately, the image sensors may be made from indium gallium arsenide (InGaAs), and CMOS transistors may be connected to each pixel of the InGaAs photodiode array. The camera may interface wirelessly or with a cable (e.g., USB, Ethernet cable, or fiber optics cable) to a computer or tablet or smart phone, where the images may be captured and processed. These are a few examples of infrared cameras, but other SWIR or infrared cameras may be used and are intended to be covered by this disclosure.

Figure 16A:
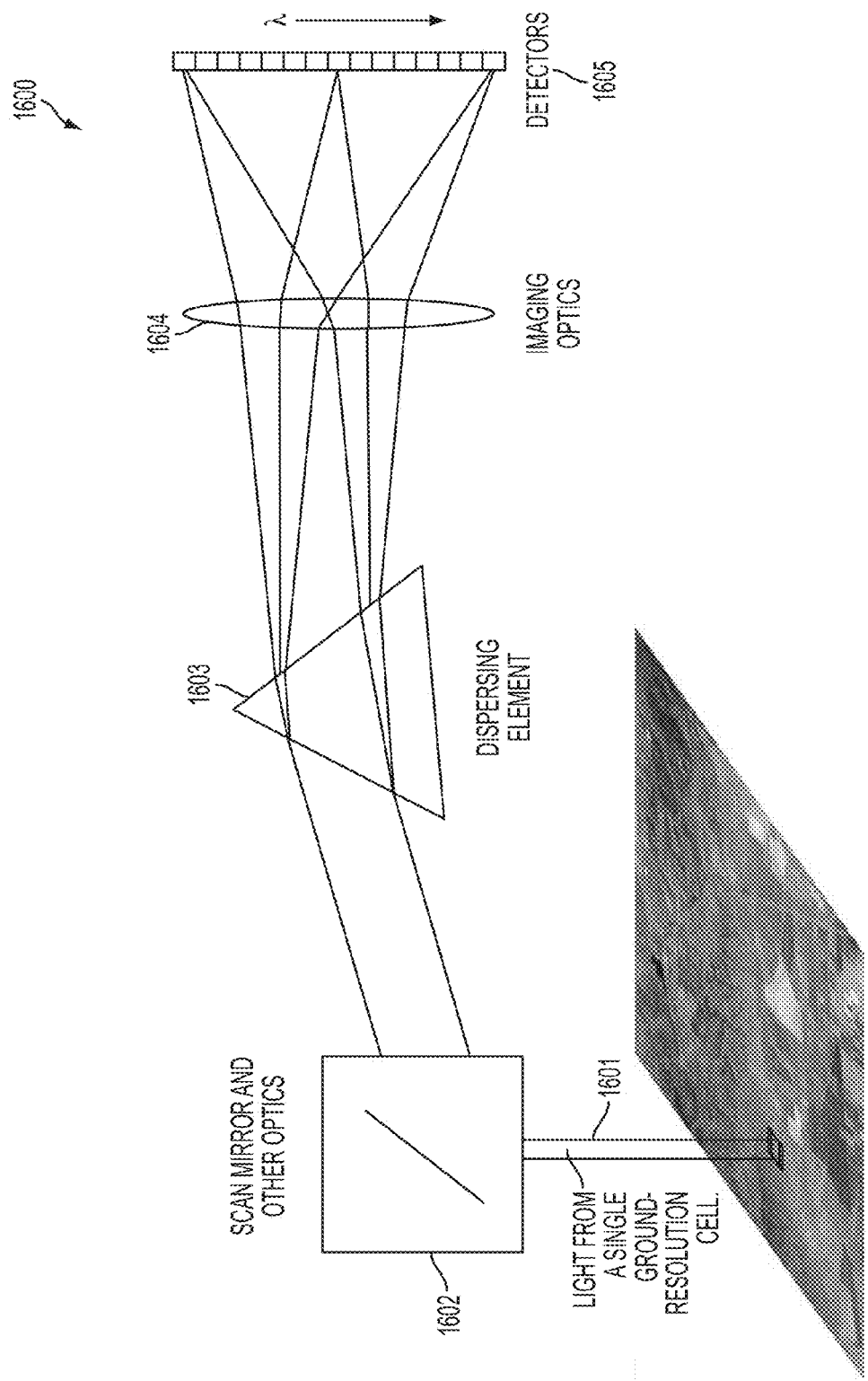
FIG. 16A is a schematic diagram of the basic elements of an imaging spectrometer.

In another embodiment, an imaging spectrometer may be used to detect the light received from the sample. For example, FIG. 16A shows a schematic diagram 1600 of the basic elements of an imaging spectrometer. The input light 1601 from the sample may first be directed by a scanning mirror and/or other optics 1602. An optical dispersing element 1603, such as a grating or prism, in the spectrometer may split the light into many narrow, adjacent wavelength bands, which may then be passed through imaging optics 1604 onto one or more detectors or detector arrays 1605. Some sensors may use multiple detector arrays to measure hundreds of narrow wavelength bands.

Figure 16B:
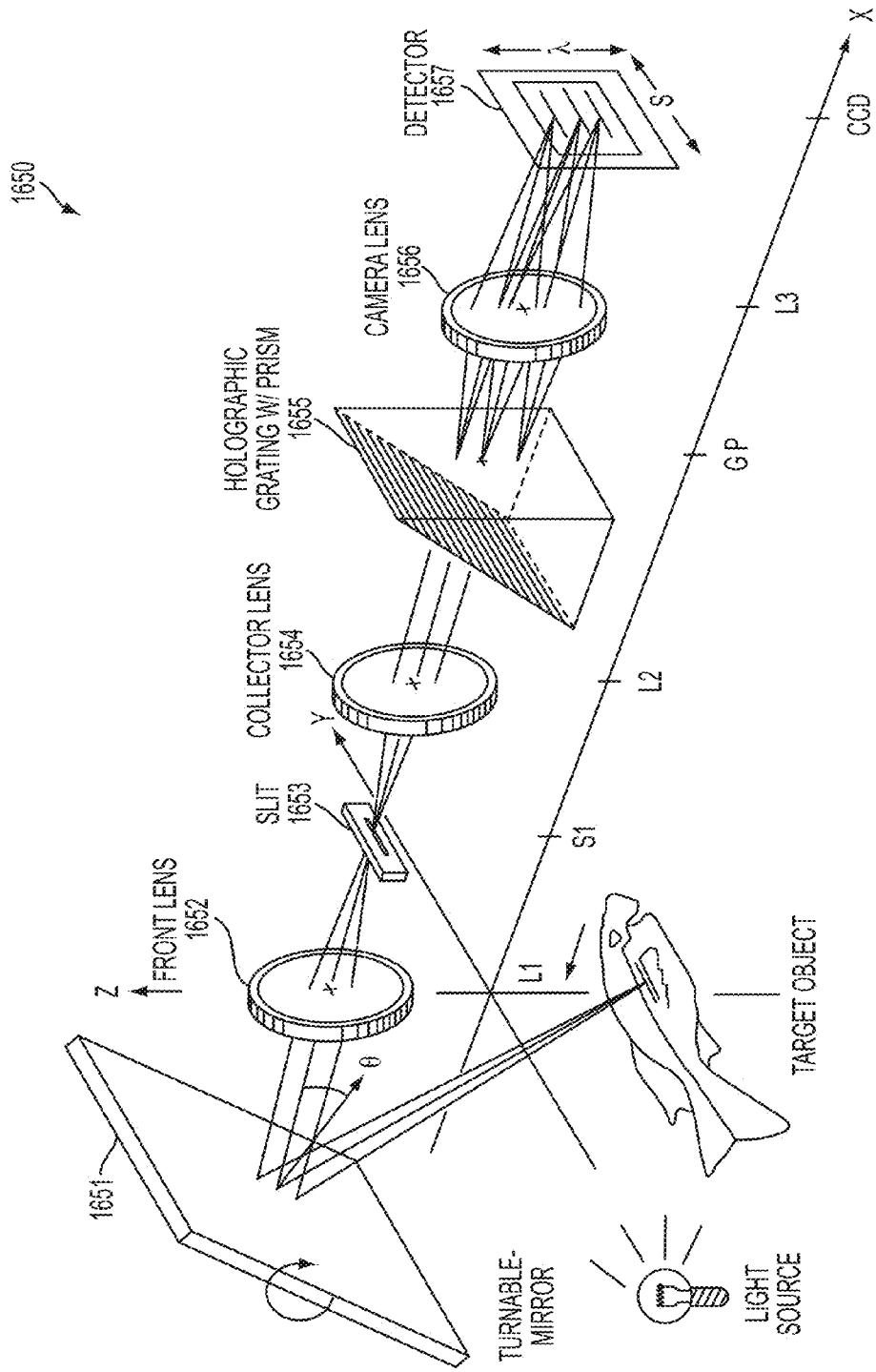
FIG. 16B illustrates one example of a typical imaging spectrometer used in hyper-spectral imaging systems.

An example of a typical imaging spectrometer 1650 used in hyper-spectral imaging systems is illustrated in FIG. 16B. In this particular embodiment, the input light may be directed first by a tunable mirror 1651. A front lens 1652 may be placed before the entrance slit 1653 and the collector lens 1654. In this embodiment, the dispersing element is a holographic grating with a prism 1655, which separates the different wavelength bands. Then, a camera lens 1656 may be used to image the wavelengths onto a detector or camera 1657.

FIG. 16 provide particular examples, but some of the elements may not be used, or other elements may be added, and these are also intended to be covered by this disclosure. For instance, a scanning spectrometer may be used before the detector, where a grating or dispersive element is scanned to vary the wavelength being measured by the detector. In yet another embodiment, filters may be used before one or more detectors to select the wavelengths or wavelength bands to be measured. This may be particularly useful if only a few bands or wavelengths are to be measured. The filters may be dielectric filters, Fabry-Perot filters, absorption or reflection filters, fiber gratings, or any other wavelength selective filter. In one embodiment, a wavelength division multiplexer, WDM, may be used followed by one or more detectors or detector arrays. One example of a planar wavelength division multiplexer may be a waveguide grating router or an arrayed waveguide grating. The WDM may be fiber coupled, and detectors may be placed directly at the output or the detectors may be coupled through fibers to the WDM. Some of these components may also be combined with the configurations in FIG. 16.

While the above detection systems could be categorized as single path detection systems, it may be advantageous in some cases to use multi-path detection systems. In one embodiment, a detection system from a Fourier transform infrared spectrometer, FTIR, may be used. The received light may be incident on a particular configuration of mirrors, called a Michelson interferometer, that allows some wavelengths to pass through but blocks others due to wave interference. The beam may be modified for each new data point by moving one of the mirrors, which changes the set of wavelengths that pass through. This collected data is called an interferogram. The interferogram is then processed, typically on a computing system, using an algorithm called the Fourier transform. One advantageous feature of FTIR is that it may simultaneously collect spectral data in a wide spectral range.

Figure 17:
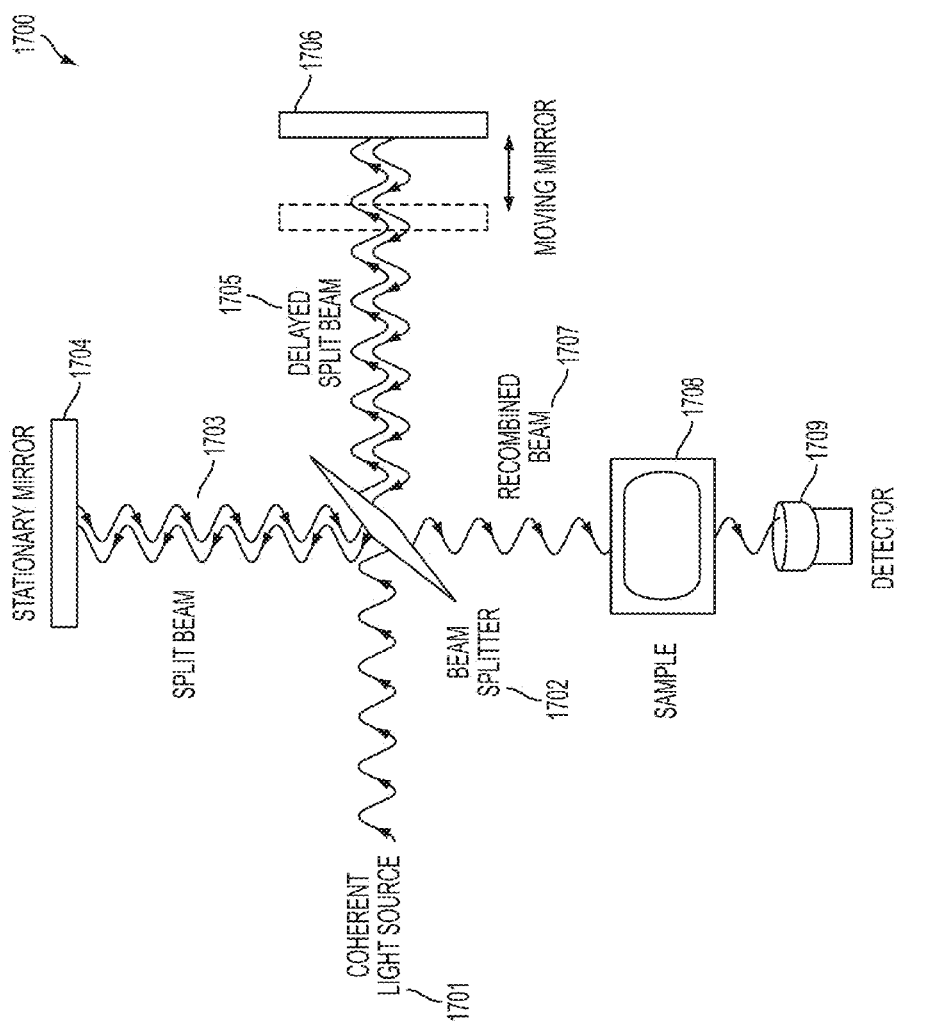
FIG. 17 shows one example of the Fourier transform infrared spectrometer.

FIG. 17 illustrates one example of the FTIR spectrometer 1700. Light from the near-infrared or SWIR light source 1701 may be collimated and directed to a beam splitter 1702. In one embodiment, the beam splitter 1702 may be a 50:50 beam splitter. One portion of the beam 1703 may be reflected toward a stationary mirror 1704, while the other portion of the beam 1705 may be transmitted towards a moving mirror 1706. Light may be reflected from the two mirrors 1704, 1706 back to the beam splitter 1702, and then a portion of the recombined beam 1707 may be directed toward the sample 1708. The recombined beam 1707 may be focused onto the sample 1708, in one embodiment. On leaving the sample 1708, the light may be refocused or at least collected at a detector 1709. A background interferogram may be obtained by using the set-up 1700 without a sample in the chamber 1708. When a sample is inserted into 1708, the background interferogram may be modulated by the presence of absorption bands in the sample. The FTIR spectrometer may have several advantages compared to a scanning (dispersive) spectrometer. Since all the wavelengths may be collected simultaneously, the FTIR may result in a higher signal-to-noise ratio for a given scan time or a shorter scan time for a given resolution. Moreover, unlike a spectrometer where a slit may limit the amount of the beam detected, the FTIR may accommodate the entire diameter of the beam coming from the light source 1701. The configuration 1700 is one example of an FTIR, but other configurations may also be used, and these are also intended to be covered by this disclosure.

Figure 18:
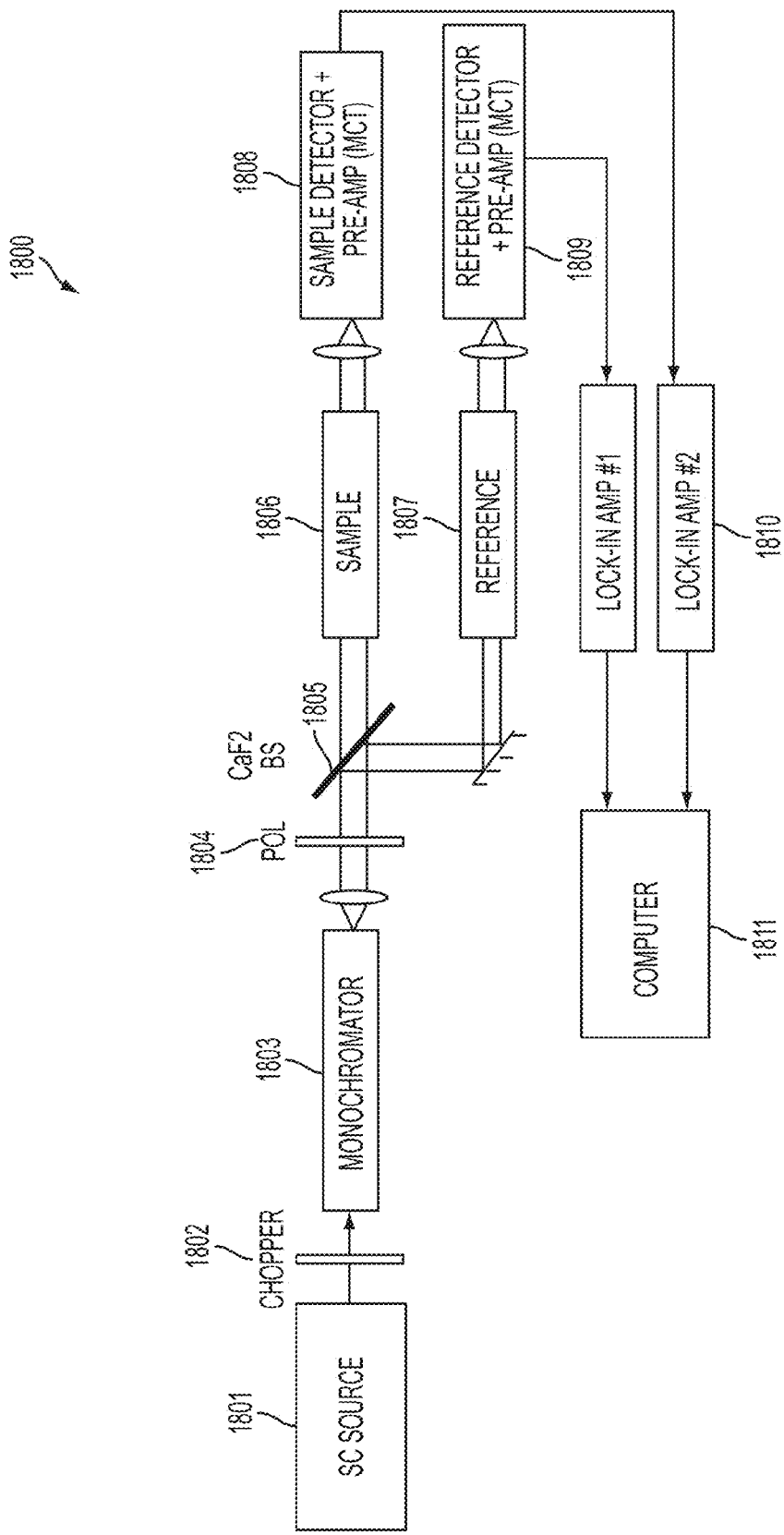
FIG. 18 exemplifies a dual-beam experimental set-up that may be used to subtract out (or at least minimize the adverse effects of) light source fluctuations.

In yet another example of multi-beam detection systems, a dual-beam set-up 1800 such as in FIG. 18 may be used to subtract out (or at least minimize the adverse effects of) light source fluctuations. In one embodiment, the output from an SC source 1801 may be collimated using a CaF$_2$ lens 1802 and then focused into the entrance slit of the monochromator 1803. At the exit slit, light at the selected wavelength is collimated again and may be passed through a polarizer 1804 before being incident on a calcium fluoride beam splitter 1805. After passing through the beam splitter 1805, the light is split into a sample 1806 and reference 1807 arm to enable ratiometric detection that may cancel out effects of intensity fluctuations in the SC source 1801. The light in the sample arm 1806 passes through the sample of interest and is then focused onto a HgCdTe detector 1808 connected to a pre-amp. A chopper 1802 and lock-in amplifier 1810 setup enable low noise detection of the sample arm signal. The light in the reference arm 1807 passes through an empty container (cuvette, gas cell etc.) of the same kind as used in the sample arm. A substantially identical detector 1809, pre-amp and lock-in amplifier 1810 is used for detection of the reference arm signal. The signal may then be analyzed using a computer system 1811. This is one particular example of a method to remove fluctuations from the light source, but other components may be added and other configurations may be used, and these are also intended to be covered by this disclosure.

Although particular examples of detection systems have been described, combinations of these systems or other systems may also be used, and these are also within the scope of this disclosure. As one example, environmental fluctuations (such as turbulence or winds) may lead to fluctuations in the beam for active remote sensing or hyper-spectral imaging. A configuration such as FIG. 18 may be able to remove the effect of environmental fluctuations. Yet another technique may be to "wobble" the light beam after the light source using a vibrating mirror. The motion may lead to the beam moving enough to wash out spatial fluctuations within the beam waist at the sample or detection system. If the vibrating mirror is scanned faster than the integration time of the detectors, then the spatial fluctuations in the beam may be integrated out. Alternately, some sort of synchronous detection system may be used, where the detection is synchronized to the vibrating frequency.

Light Sources for SWIR and Near Infrared

There are a number of light sources that may be used in the near infrared. To be more specific, the discussion below will consider light sources operating in the short wave infrared (SWIR), which may cover the wavelength range of approximately 1400 nm to 2500 nm. Other wavelength ranges may also be used for the applications described in this disclosure, so the discussion below is merely provided for exemplary types of light sources. The SWIR wavelength range may be valuable for a number of reasons. The SWIR corresponds to a transmission window through water and the atmosphere. Also, the so-called "eye-safe" wavelengths are wavelengths longer than approximately 1400 nm as previously described.

Different light sources may be selected for the SWIR based on the needs of the application. Some of the features for selecting a particular light source include power or intensity, wavelength range or bandwidth, spatial or temporal coherence, spatial beam quality for focusing or transmission over long distance, and pulse width or pulse repetition rate. Depending on the application, lamps, light emitting diodes (LEDs), laser diodes (LD's), tunable LD's, super-luminescent laser diodes (SLDs), fiber lasers or super-continuum sources (SC) may be advantageously used. Also, different fibers may be used for transporting the light, such as fused silica fibers, plastic fibers, mid-infrared fibers (e.g., tellurite, chalcogenides, fluorides, ZBLAN, etc), or a hybrid of these fibers.

Lamps may be used if low power or intensity of light is required in the SWIR, and if an incoherent beam is suitable. In one embodiment, in the SWIR an incandescent lamp that can be used is based on tungsten and halogen, which have an emission wavelength between approximately 500 nm to 2500 nm. For low intensity applications, it may also be possible to use thermal sources, where the SWIR radiation is based on the black body radiation from the hot object. Although the thermal and lamp based sources are broadband and have low intensity fluctuations, it may be difficult to achieve a high signal-to-noise ratio due to the low power levels. Also, the lamp based sources tend to be energy inefficient.

In another embodiment, LED's can be used that have a higher power level in the SWIR wavelength range. LED's also produce an incoherent beam, but the power level can be higher than a lamp and with higher energy efficiency. Also, the LED output may more easily be modulated, and the LED provides the option of continuous wave or pulsed mode of operation. LED's are solid state components that emit a wavelength band that is of moderate width, typically between about 20 nm to 40 nm. There are also so-called super-luminescent LEDs that may even emit over a much wider wavelength range. In another embodiment, a wide band light source may be constructed by combining different LEDs that emit in different wavelength bands, some of which could preferably overlap in spectrum. One advantage of LEDs as well as other solid state components is the compact size that they may be packaged into.

In yet another embodiment, various types of laser diodes may be used in the SWIR wavelength range. Just as LEDs may be higher in power but narrower in wavelength emission than lamps and thermal sources, the LDs may be yet higher in power but yet narrower in wavelength emission than LEDs. Different kinds of LDs may be used, including Fabry-Perot LDs, distributed feedback (DFB (LDs, distributed Bragg reflector (DBR) LDs. Since the LDs have relatively narrow wavelength range (typically under 10 nm), in one embodiment a plurality of LDs may be used that are at different wavelengths in the SWIR. The various LDs may be spatially multiplexed, polarization multiplexed, wavelength multiplexed, or a combination of these multiplexing methods. Also, the LDs may be fiber pig-tailed or have one or more lenses on the output to collimate or focus the light. Another advantage of LDs is that they may be packaged compactly and may have a spatially coherent beam output. Moreover, tunable LDs that can tune over a range of wavelengths are also available. The tuning may be done by varying the temperature, or electrical current may be used in particular structures such as distributed Bragg reflector LDs. In another embodiment, external cavity LDs may be used that have a tuning element, such as a fiber grating or a bulk grating, in the external cavity.

In another embodiment, super-luminescent laser diodes may provide higher power as well as broad bandwidth. An SLD is typically an edge emitting semiconductor light source based on super-luminescence (e.g., this could be amplified spontaneous emission). SLDs combine the higher power and brightness of LDs with the low coherence of conventional LEDs, and the emission band for SLD's may be 5 nm to 100 nm wide, preferably in the 60 nm to 100 nm range. Although currently SLDs are commercially available in the wavelength range of approximately 400 nm to 1700 nm, SLDs could and may in the future be made that cover a broader region of the SWIR.

Figure 19:
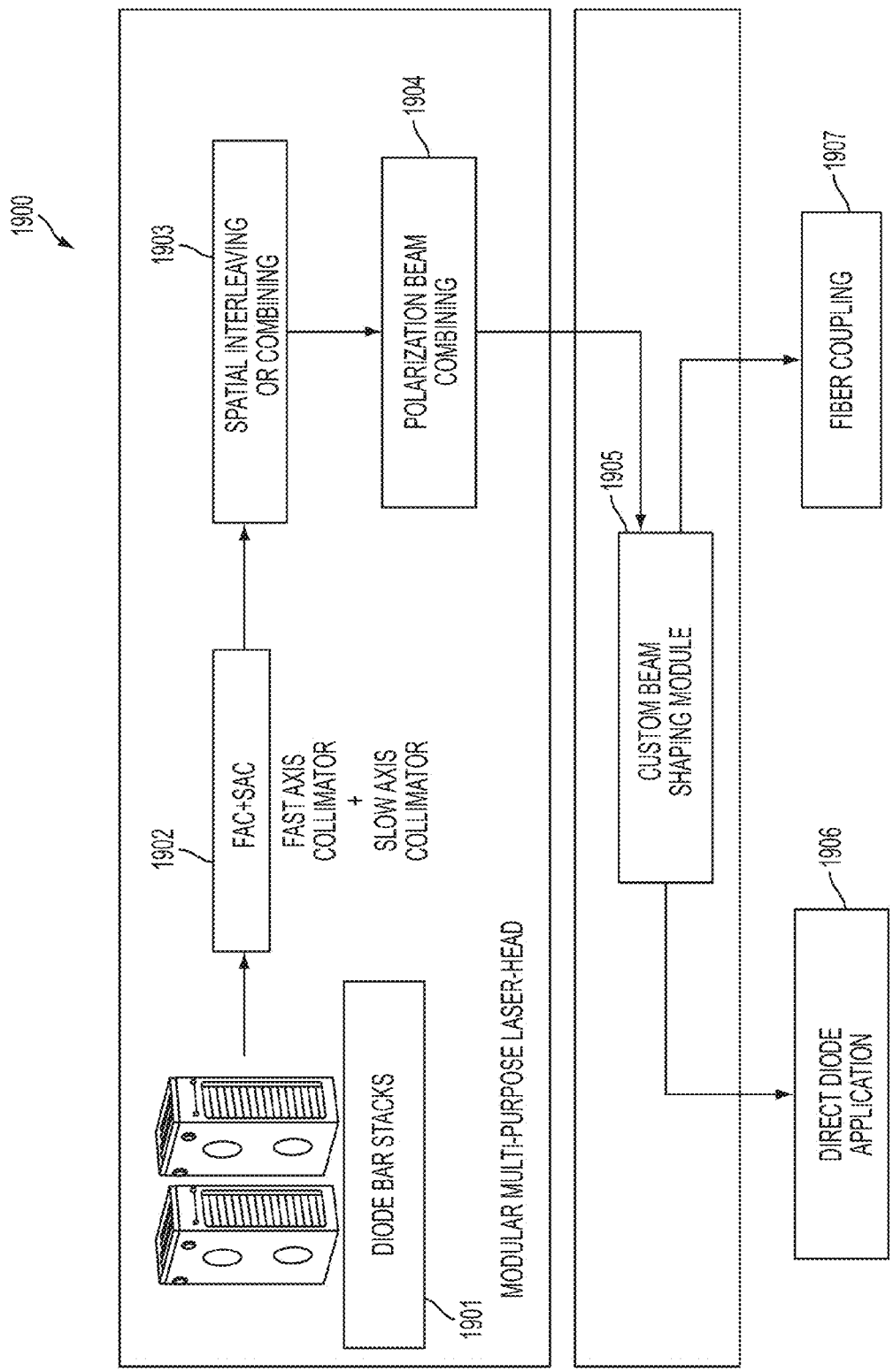
FIG. 19 illustrates a block diagram or building blocks for constructing high power laser diode assemblies.

In yet another embodiment, high power LDs for either direct excitation or to pump fiber lasers and SC light sources may be constructed using one or more laser diode bar stacks. FIG. 19 shows an example block diagram 1900 with building blocks for constructing the high power LDs. In this embodiment, one or more diode bar stacks 1901 may be used, where the diode bar stack may be an array of several single emitter LDs. Since the fast axis (e.g., vertical direction) may be nearly diffraction limited while the slow-axis (e.g., horizontal axis) may be far from diffraction limited, different collimators 1902 may be used for the two axes.

The brightness may be increased by spatially combining the beams from multiple stacks 1903. The combiner may include spatial interleaving, wavelength multiplexing, or a combination of the two. Different spatial interleaving schemes may be used, such as using an array of prisms or mirrors with spacers to bend one array of beams into the beam path of the other. In another embodiment, segmented mirrors with alternate high-reflection and anti-reflection coatings may be used. Moreover, the brightness may be increased by polarization beam combining 1904 the two orthogonal polarizations, such as by using a polarization beam splitter. In a particular embodiment, the output may then be focused or coupled into a large diameter core fiber. As an example, typical dimensions for the large diameter core fiber range from diameters of approximately 100 microns to 400 microns or more. Alternatively or in addition, a custom beam shaping module 1905 may be used, depending on the particular application. For example, the output of the high power LD may be used directly 1906, or it may be fiber coupled 1907 to combine, integrate, or transport the high power LD energy. These high power LDs may grow in importance because the LD powers can rapidly scale up. For example, instead of the power being limited by the power available from a single emitter, the power may increase in multiples depending on the number of diodes multiplexed and the size of the large diameter fiber. Although FIG. 19 is shown as one embodiment, some or all of the elements may be used in a high power LD, or additional elements may also be used.

SWIR Super-Continuum Lasers

Each of the light sources described above have particular strengths, but they also may have limitations. For example, there is typically a trade-off between wavelength range and power output. Also, sources such as lamps, thermal sources, and LEDs produce incoherent beams that may be difficult to focus to a small area and may have difficulty propagating for long distances. An alternative source that may overcome some of these limitations is an SC light source. Some of the advantages of the SC source may include high power and intensity, wide bandwidth, spatially coherent beam that can propagate nearly transform limited over long distances, and easy compatibility with fiber delivery.

Supercontinuum lasers may combine the broadband attributes of lamps with the spatial coherence and high brightness of lasers. By exploiting a modulational instability initiated supercontinuum (SC) mechanism, an all-fiber-integrated SC laser with no moving parts may be built using commercial-off-the-shelf (COTS) components. Moreover, the fiber laser architecture may be a platform where SC in the visible, near-infrared/SWIR, or mid-IR can be generated by appropriate selection of the amplifier technology and the SC generation fiber. But until recently, SC lasers were used primarily in laboratory settings since typically large, table-top, mode-locked lasers were used to pump nonlinear media such as optical fibers to generate SC light. However, those large pump lasers may now be replaced with diode lasers and fiber amplifiers that gained maturity in the telecommunications industry.

Figure 20:
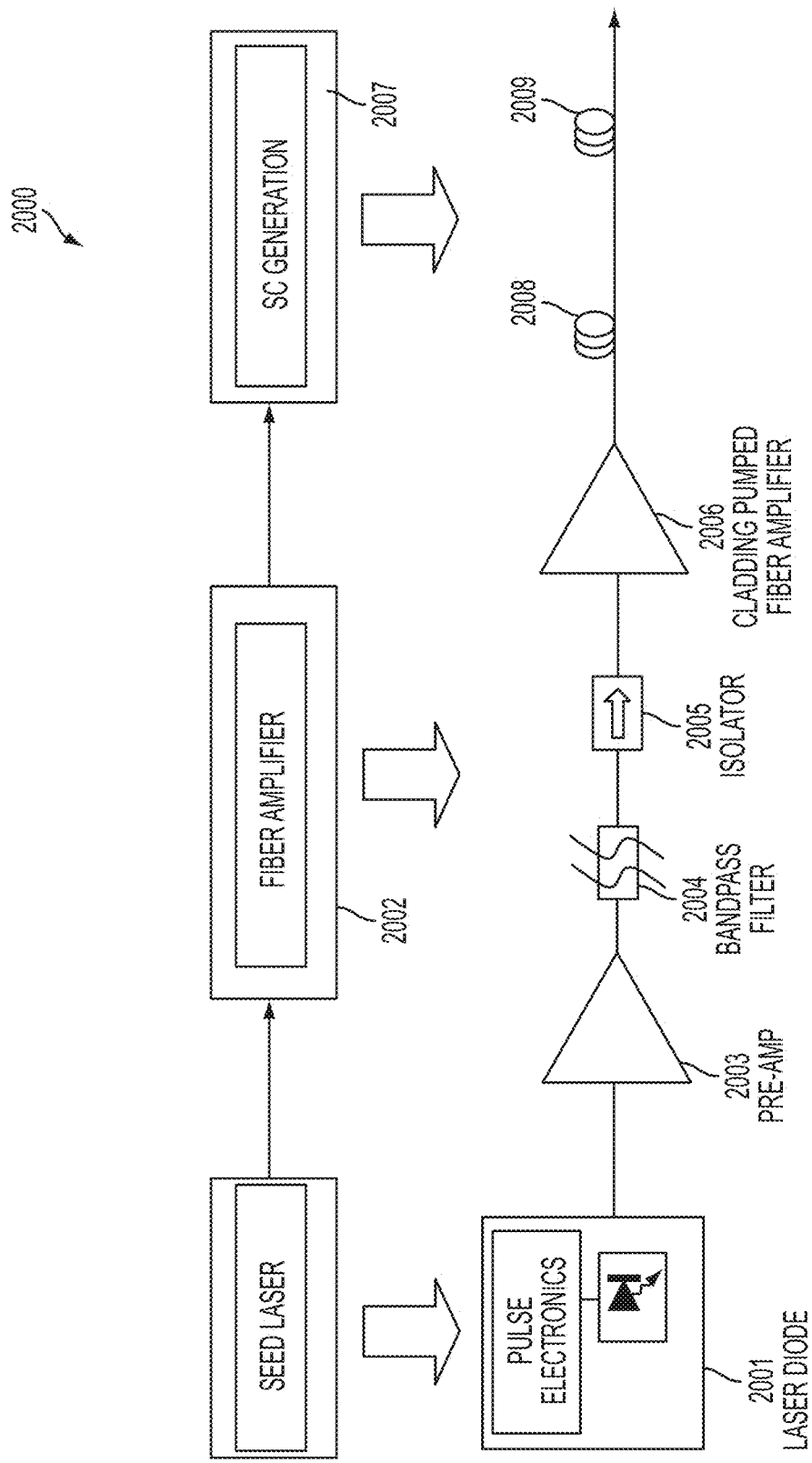
FIG. 20 shows a platform architecture for different wavelength ranges for an all-fiber-integrated, high powered, super-continuum light source.

In one embodiment, an all-fiber-integrated, high-powered SC light source 2000 may be elegant for its simplicity (FIG. 20). The light may be first generated from a seed laser diode 2001. For example, the seed LD 2001 may be a distributed feedback (DFB) laser diode with a wavelength near 1542 nm or 1550 nm, with approximately 0.5-2.0 ns pulsed output, and with a pulse repetition rate between one kilohertz to about 100 MHz or more. The output from the seed laser diode may then be amplified in a multiple-stage fiber amplifier 2002 comprising one or more gain fiber segments. In a particular embodiment, the first stage pre-amplifier 2003 may be designed for optimal noise performance. For example, the pre-amplifier 2003 may be a standard erbium-doped fiber amplifier or an erbium/ytterbium doped cladding pumped fiber amplifier. Between amplifier stages 2003 and 2006, it may be advantageous to use band-pass filters 2004 to block amplified spontaneous emission and isolators 2005 to prevent spurious reflections. Then, the power amplifier stage 2006 may use a cladding-pumped fiber amplifier that may be optimized to minimize nonlinear distortion. The power amplifier fiber 2006 may also be an erbium-doped fiber amplifier, if only low or moderate power levels are to be generated.

The SC generation 2007 may occur in the relatively short lengths of fiber that follow the pump laser. Exemplary SC fiber lengths may range from a few millimeters to 100 m or more. In one embodiment, the SC generation may occur in a first fiber 2008 where the modulational-instability initiated pulse break-up occurs primarily, followed by a second fiber 2009 where the SC generation and spectral broadening occurs primarily.

In one embodiment, one or two meters of standard single-mode fiber (SMF) after the power amplifier stage may be followed by several meters of SC generation fiber. For this example, in the SMF the peak power may be several kilowatts and the pump light may fall in the anomalous group-velocity dispersion regime—often called the soliton regime. For high peak powers in the anomalous dispersion regime, the nanosecond pulses may be unstable due to a phenomenon known as modulational instability, which is basically parametric amplification in which the fiber nonlinearity helps to phase match the pulses. As a consequence, the nanosecond pump pulses may be broken into many shorter pulses as the modulational instability tries to form soliton pulses from the quasi-continuous-wave background. Although the laser diode and amplification process starts with approximately nanosecond-long pulses, modulational instability in the short length of SMF fiber may form approximately 0.5 ps to several-picosecond-long pulses with high intensity. Thus, the few meters of SMF fiber may result in an output similar to that produced by mode-locked lasers, except in a much simpler and cost-effective manner.

The short pulses created through modulational instability may then be coupled into a nonlinear fiber for SC generation. The nonlinear mechanisms leading to broadband SC may include four-wave mixing or self-phase modulation along with the optical Raman effect. Since the Raman effect is self-phase-matched and shifts light to longer wavelengths by emission of optical photons, the SC may spread to longer wavelengths very efficiently. The short-wavelength edge may arise from four-wave mixing, and often times the short wavelength edge may be limited by increasing group-velocity dispersion in the fiber. In many instances, if the particular fiber used has sufficient peak power and SC fiber length, the SC generation process may fill the long-wavelength edge up to the transmission window.

Mature fiber amplifiers for the power amplifier stage 2006 include ytterbium-doped fibers (near 1060 nm), erbium-doped fibers (near 1550 nm), erbium/ytterbium-doped fibers (near 1550 nm), or thulium-doped fibers (near 2000 nm). In various embodiments, candidates for SC fiber 2009 include fused silica fibers (for generating SC between 0.8-2.7 µm), mid-IR fibers such as fluorides, chalcogenides, or tellurites (for generating SC out to 4.5 µm or longer), photonic crystal fibers (for generating SC between 0.4-1.7 µm), or combinations of these fibers. Therefore, by selecting the appropriate fiber-amplifier doping for 2006 and nonlinear fiber 2009, SC may be generated in the visible, near-IR/SWIR, or mid-IR wavelength region.

The configuration 2000 of FIG. 20 is just one particular example, and other configurations can be used and are intended to be covered by this disclosure. For example, further gain stages may be used, and different types of lossy elements or fiber taps may be used between the amplifier stages. In another embodiment, the SC generation may occur partially in the amplifier fiber and in the pig-tails from the pump combiner or other elements. In yet another embodiment, polarization maintaining fibers may be used, and a polarizer may also be used to enhance the polarization contrast between amplifier stages. Also, not discussed in detail are many accessories that may accompany this set-up, such as driver electronics, pump laser diodes, safety shut-offs, and thermal management and packaging.

Figure 21:
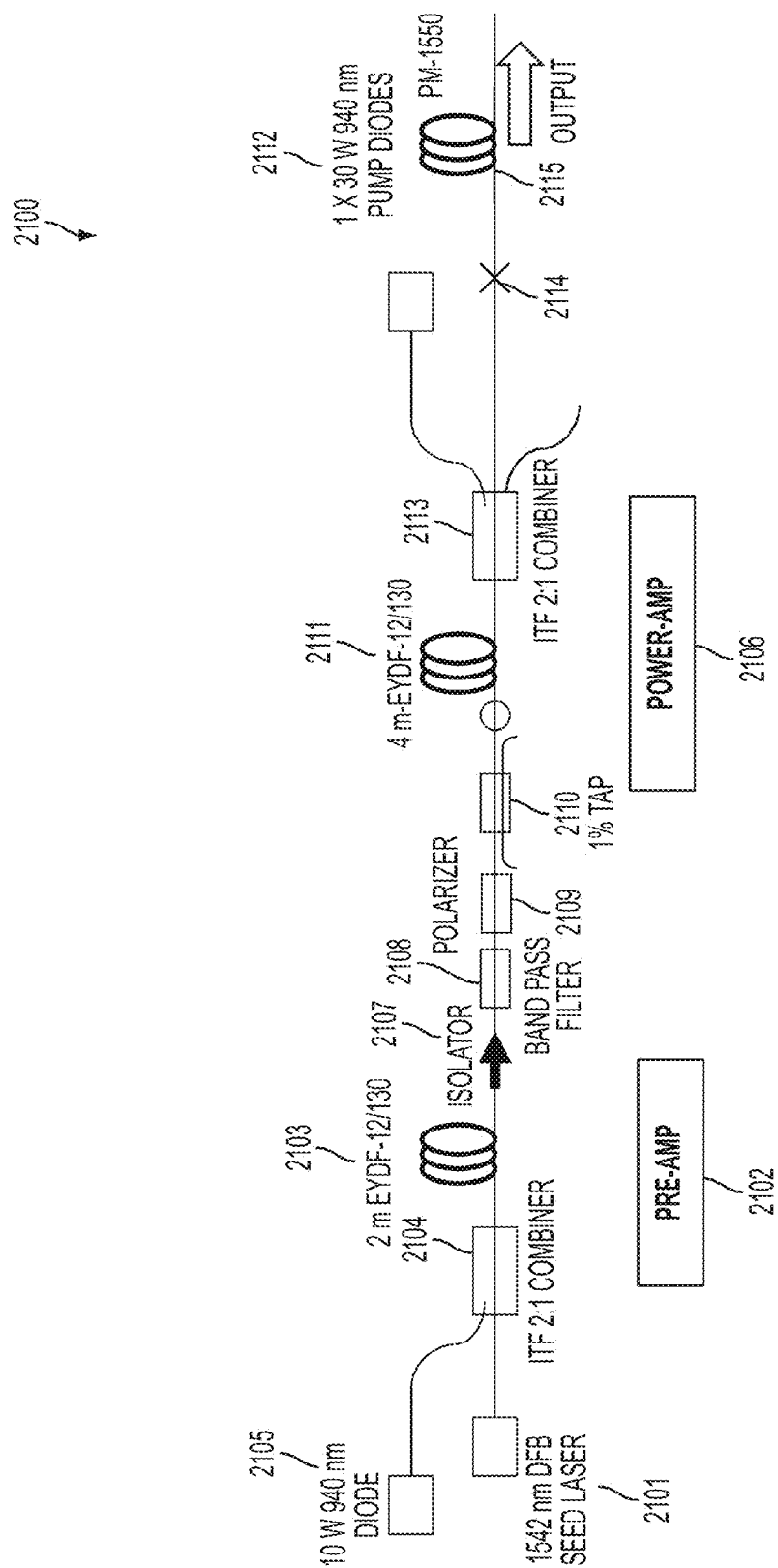
FIG. 21 illustrates one embodiment for a short-wave infrared super-continuum light source.

In one embodiment, one example of the SC laser that operates in the SWIR is illustrated in FIG. 21. This SWIR SC source 2100 produces an output of up to approximately 5 W over a spectral range of about 1.5-2.4 microns, and this particular laser is made out of polarization maintaining components. The seed laser 2101 is a distributed feedback (DFB) laser operating near 1542 nm producing approximately 0.5 nsec pulses at an about 8 MHz repetition rate. The pre-amplifier 2102 is forward pumped and uses about 2 m length of erbium/ytterbium cladding pumped fiber 2103 (often also called dual-core fiber) with an inner core diameter of 12 microns and outer core diameter of 130 microns. The pre-amplifier gain fiber 2103 is pumped using a 10 W laser diode near 940 nm 2105 that is coupled in using a fiber combiner 2104.

In this particular 5 W unit, the mid-stage between amplifier stages 2102 and 2106 comprises an isolator 2107, a band-pass filter 2108, a polarizer 2109 and a fiber tap 2110. The power amplifier 2106 uses an approximately 4 m length of the 12/130 micron erbium/ytterbium doped fiber 2111 that is counter-propagating pumped using one or more 30 W laser diodes near 940 nm 2112 coupled in through a combiner 2113. An approximately 1-2 m length of the combiner pig-tail helps to initiate the SC process, and then a length of PM-1550 fiber 2115 (polarization maintaining, single-mode, fused silica fiber optimized for 1550 nm) is spliced 2114 to the combiner output.

Figure 22:
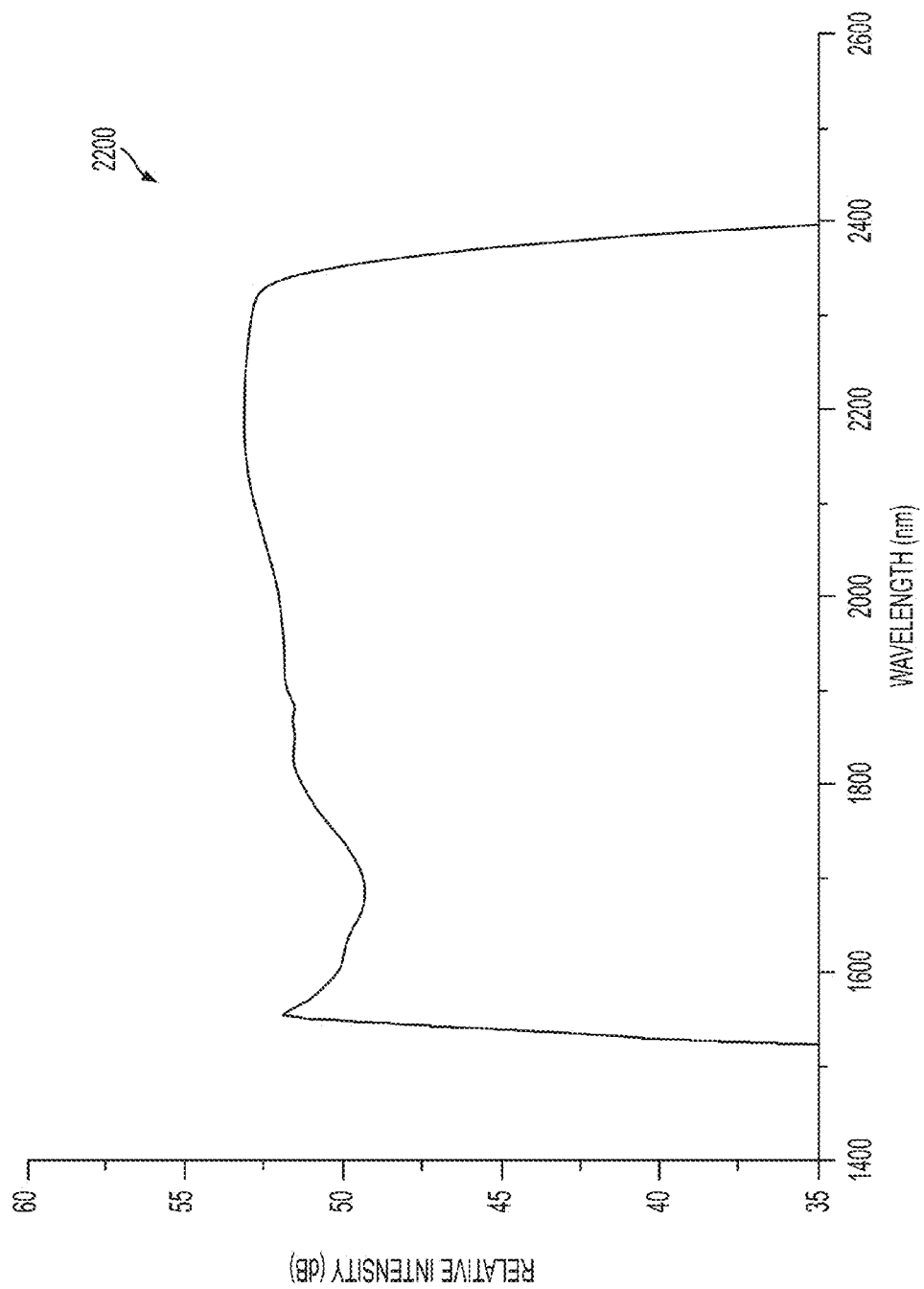
FIG. 22 shows the output spectrum from the SWIR SC laser of FIG. 21 when about a 10 m length of fiber for SC generation is used. This fiber is a single-mode, non-dispersion shifted fiber that is optimized for operation near 1550 nm.

If an output fiber of about 10 m in length is used, then the resulting output spectrum 2200 is shown in FIG. 22. The details of the output spectrum 2200 depend on the peak power into the fiber, the fiber length, and properties of the fiber such as length and core size, as well as the zero dispersion wavelength and the dispersion properties. For example, if a shorter length of fiber is used, then the spectrum actually reaches to longer wavelengths (e.g., a 2 m length of SC fiber broadens the spectrum to about 2500 nm). Also, if extra-dry fibers are used with less O—H content, then the wavelength edge may also reach to a longer wavelength. To generate more spectrum toward the shorter wavelengths, the pump wavelength (in this case around 1542 nm) should be close to the zero dispersion wavelength in the fiber. For example, by using a dispersion shifted fiber or so-called non-zero dispersion shifted fiber, the short wavelength edge may shift to shorter wavelengths.

Although one particular example of a 5 W SWIR-SC has been described, different components, different fibers, and different configurations may also be used consistent with this disclosure. For instance, another embodiment of the similar configuration 2100 in FIG. 21 may be used to generate high powered SC between approximately 1060 nm and 1800 nm. For this embodiment, the seed laser 2101 may be a distributed feedback laser diode around 1064 nm, the pre-amplifier gain fiber 2103 may be a ytterbium-doped fiber amplifier with 10/125 microns dimensions, and the pump laser 2105 may be a 10 W laser diode near 915 nm. A mode field adapter may be included in the mid-stage, in addition to the isolator 2107, band pass filter 2108, polarizer 2109 and tap 2110. The gain fiber 2111 in the power amplifier may be an about 20 m length of ytterbium-doped fiber with 25/400 microns dimension. The pump 2112 for the power amplifier may be up to six pump diodes providing 30 W each near 915 nm. For this much pump power, the output power in the SC may be as high as 50 W or more.

In one embodiment, it may be desirous to generate high power SWIR SC over 1.4-1.8 microns and separately 2-2.5 microns (the window between 1.8 and 2 microns may be less important due to the strong water and atmospheric absorption). For example, the top SC source of FIG. 23 can lead to bandwidths ranging from about 1400 nm to 1800 nm or broader, while the lower SC source of FIG. 23 can lead to bandwidths ranging from about 1900 nm to 2500 nm or broader. Since these wavelength ranges are shorter than about 2500 nm, the SC fiber can be based on fused silica fiber. Exemplary SC fibers include standard single-mode fiber SMF, high-nonlinearity fiber, high-NA fiber, dispersion shifted fiber, dispersion compensating fiber, and photonic crystal fibers. Non-fused-silica fibers can also be used for SC generation, including chalcogenides, fluorides, ZBLAN, tellurites, and germanium oxide fibers.

Figure 23:
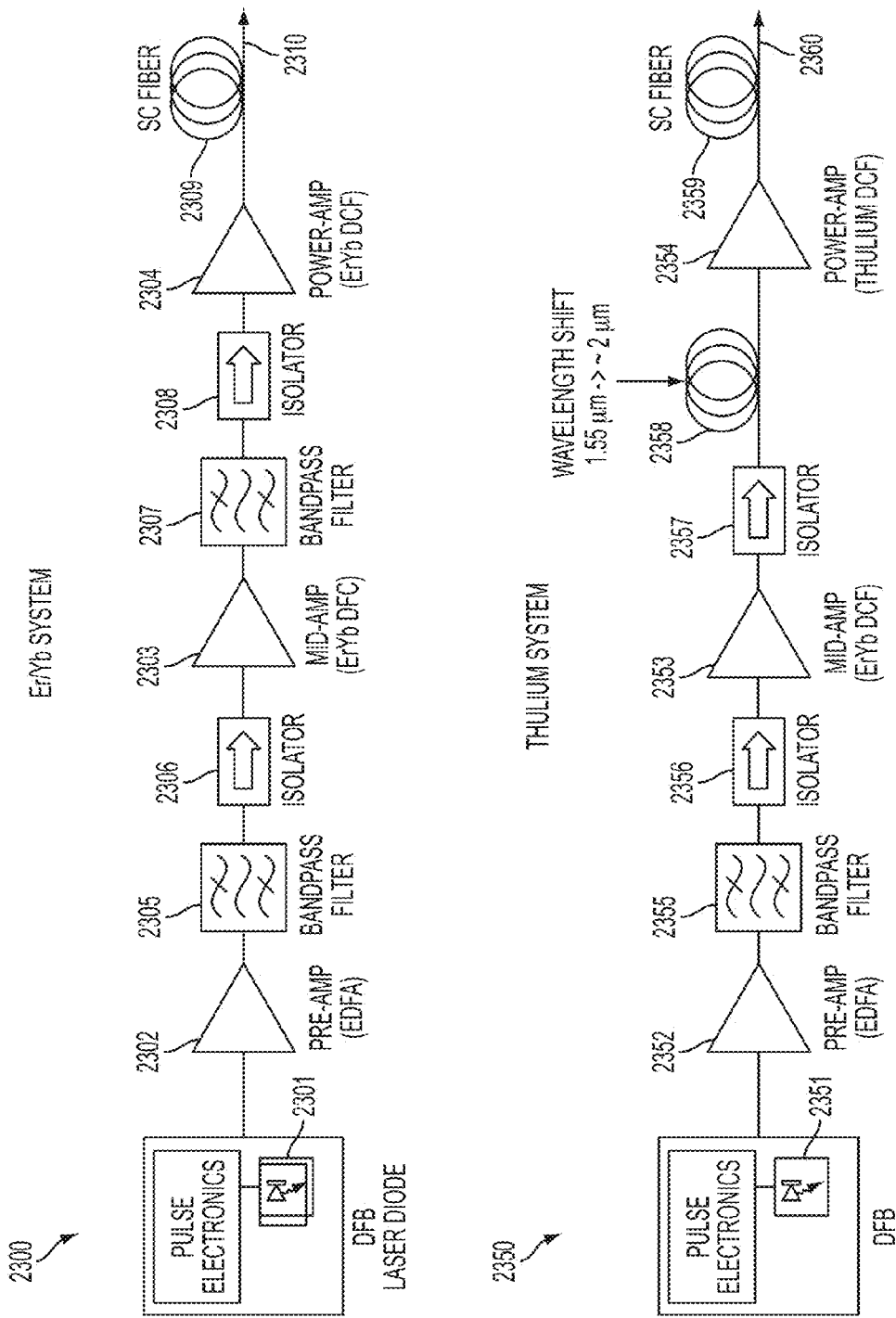
FIG. 23 illustrates high power SWIR-SC lasers that may generate light between approximately 1.4-1.8 microns (top) or approximately 2-2.5 microns (bottom).

In one embodiment, the top of FIG. 23 illustrates an exemplary block diagram for an SC source 2300 capable of generating light between approximately 1400 nm and 1800 nm or broader. As an example, a pump fiber laser similar to FIG. 21 can be used as the input to a SC fiber 2309. The seed laser diode 2301 can comprise a DFB laser that generates, for example, several milliwatts of power around 1542 nm or 1553 nm. The fiber pre-amplifier 2302 can comprise an erbium-doped fiber amplifier or an erbium/ytterbium doped double clad fiber. In this example a mid-stage amplifier 2303 can be used, which can comprise an erbium/ytterbium doped double-clad fiber. A bandpass filter 2305 and isolator 2306 may be used between the pre-amplifier 2302 and mid-stage amplifier 2303. The power amplifier stage 2304 can comprise a larger core size erbium/ytterbium doped double-clad fiber, and another bandpass filter 2307 and isolator 2308 can be used before the power amplifier 2304. The output of the power amplifier can be coupled to the SC fiber 2309 to generate the SC output 2310. This is just one exemplary configuration for an SC source, and other configurations or elements may be used consistent with this disclosure.

In yet another embodiment, the bottom of FIG. 23 illustrates a block diagram for an exemplary SC source 2350 capable of generating light between approximately 1900 nm and 2500 nm or broader. As an example, the seed laser diode 2351 can comprise a DFB or DBR laser that generates, for example, several milliwatts of power around 1542 nm or 1553 nm. The fiber pre-amplifier 2352 can comprise an erbium-doped fiber amplifier or an erbium/ytterbium doped double-clad fiber. In this example a mid-stage amplifier 2353 can be used, which can comprise an erbium/ytterbium doped double-clad fiber. A bandpass filter 2355 and isolator 2356 may be used between the pre-amplifier 2352 and mid-stage amplifier 2353. The power amplifier stage 2354 can comprise a thulium doped double-clad fiber, and another isolator 2357 can be used before the power amplifier 2354. Note that the output of the mid-stage amplifier 2353 can be approximately near 1542 nm, while the thulium-doped fiber amplifier 2354 can amplify wavelengths longer than approximately 1900 nm and out to about 2100 nm. Therefore, for this configuration wavelength shifting may be required between 2353 and 2354. In one embodiment, the wavelength shifting can be accomplished using a length of standard single-mode fiber 2358, which can have a length between approximately 5 m and 50 m, for example. The output of the power amplifier 2354 can be coupled to the SC fiber 2359 to generate the SC output 2360. This is just one exemplary configuration for an SC source, and other configurations or elements can be used consistent with this disclosure. For example, the various amplifier stages can comprise different amplifier types, such as erbium doped fibers, ytterbium doped fibers, erbium/ytterbium co-doped fibers and thulium doped fibers. One advantage of the SC lasers illustrated in FIGS. 20, 21, and 23 are that they may use all-fiber components, so that the SC laser can be all-fiber, monolithically integrated with no moving parts. The all-integrated configuration can consequently be robust and reliable.

FIGS. 20, 21 and 23 are examples of SC light sources that may advantageously be used for near-infrared or SWIR light generation in various spectroscopy, active remote sensing and hyper-spectral imaging applications. However, many other versions of the SC light sources may also be made that are intended to also be covered by this disclosure. For example, the SC generation fiber could be pumped by a mode-locked laser, a gain-switched semiconductor laser, an optically pumped semiconductor laser, a solid state laser, other fiber lasers, or a combination of these types of lasers. Also, rather than using a fiber for SC generation, either a liquid or a gas cell might be used as the nonlinear medium in which the spectrum is to be broadened.

Even within the all-fiber versions illustrated such as in FIG. 21, different configurations could be used consistent with the disclosure. In one embodiment, it may be desirous to have a lower cost version of the SWIR SC laser of FIG. 21. One way to lower the cost could be to use a single stage of optical amplification, rather than two stages, which may be feasible if lower output power is required or the gain fiber is optimized. For example, the pre-amplifier stage 2102 might be removed, along with at least some of the mid-stage elements. In yet another embodiment, the gain fiber could be double passed to emulate a two stage amplifier. In this example, the pre-amplifier stage 2102 might be removed, and perhaps also some of the mid-stage elements. A mirror or fiber grating reflector could be placed after the power amplifier stage 2106 that may preferentially reflect light near the wavelength of the seed laser 2101. If the mirror or fiber grating reflector can transmit the pump light near 940 nm, then this could also be used instead of the pump combiner 2113 to bring in the pump light 2112. The SC fiber 2115 could be placed between the seed laser 2101 and the power amplifier stage 2106 (SC is only generated after the second pass through the amplifier, since the power level may be sufficiently high at that time). In addition, an output coupler may be placed between the seed laser diode 2101 and the SC fiber, which now may be in front of the power amplifier 2106. In a particular embodiment, the output coupler could be a power coupler or divider, a dichroic coupler (e.g., passing seed laser wavelength but outputting the SC wavelengths), or a wavelength division multiplexer coupler. This is just one further example, but a myriad of other combinations of components and architectures could also be used for SC light sources to generate near-infrared or SWIR light that are intended to be covered by this disclosure.

Described herein are just some examples of the beneficial use of near-infrared or SWIR lasers for spectroscopy, active remote sensing or hyper-spectral imaging. However, many other spectroscopy and identification procedures can use the near-infrared or SWIR light consistent with this disclosure and are intended to be covered by the disclosure. As one example, the fiber-based super-continuum lasers may have a pulsed output with pulse durations of approximately 0.5-2 nsec and pulse repetition rates of several Megahertz. Therefore, the near-infrared or SWIR spectroscopy, active remote sensing or hyper-spectral imaging applications may also be combined with LIDAR-type applications. Namely, the distance or time axis can be added to the information based on time-of-flight measurements. For this type of information to be used, the detection system would also have to be time-gated to be able to measure the time difference between the pulses sent and the pulses received. By calculating the round-trip time for the signal, the distance of the object may be judged. In another embodiment, GPS (global positioning system) information may be added, so the near-infrared or SWIR spectroscopy, active remote sensing or hyper-spectral imagery would also have a location tag on the data. Moreover, the near-infrared or SWIR spectroscopy, active remote sensing or hyper-spectral imaging information could also be combined with two-dimensional or three-dimensional images to provide a physical picture as well as a chemical composition identification of the materials. These are just some modifications of the near-infrared or SWIR spectroscopy, active remote sensing or hyper-spectral imaging system described in this disclosure, but other techniques may also be added or combinations of these techniques may be added, and these are also intended to be covered by this disclosure.

Although the present disclosure has been described in several embodiments, a myriad of changes, variations, alterations, transformations, and modifications may be suggested to one skilled in the art, and it is intended that the present disclosure encompass such changes, variations, alterations, transformations, and modifications as falling within the spirit and scope of the appended claims.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure. While various embodiments may have been described as providing advantages or being preferred over other embodiments with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. The embodiments described herein that are described as less desirable than other embodiments or prior art implementations with respect to one or more characteristics are not outside the scope of the disclosure and may be desirable for particular applications.

What is claimed is:

1. A measurement system comprising:
   a light source configured to generate an output optical beam, comprising:
   one or more semiconductor sources configured to generate an input beam;
   one or more optical amplifiers configured to receive at least a portion of the input beam and to deliver an intermediate beam to an output end of the one or more optical amplifiers; and
   one or more optical fibers configured to receive at least a portion of the intermediate beam and to deliver at least the portion of the intermediate beam to a distal end of the one or more optical fibers to form a first optical beam;
   a nonlinear element configured to receive at least a portion of the first optical beam and to broaden a spectrum associated with the at least a portion of the first optical beam to at least 10 nm through a nonlinear effect in the nonlinear element to form the output optical beam with an output beam broadened spectrum; and
   wherein at least a portion of the output beam broadened spectrum comprises a short-wave infrared wavelength between approximately 1400 nanometers and approximately 2500 nanometers, and wherein at least a portion of the one or more fibers is a fused silica fiber with a core diameter less than approximately 400 microns;
   a measurement apparatus configured to receive a received portion of the output optical beam and to deliver a delivered portion of the output optical beam to a sample for a non-destructive and non-contact measurement, wherein the delivered portion of the output optical beam is configured to generate a spectroscopy output beam from the sample;
   a receiver configured to receive at least a portion of the spectroscopy output beam having a bandwidth of at least 10 nanometers and to process the portion of the spectroscopy output beam to generate an output signal, and wherein at least a part of the delivered portion of the output optical beam is at least partially transmitting through a packaging material covering at least a part of the sample, and wherein the output signal is based on a chemical composition of the sample; and
   wherein the delivered portion of the output optical beam is a spatially coherent beam, and wherein the sample is remote from the light source and the receiver.

2. The system of claim 1, wherein the receiver comprises a Fourier transform infrared (FTIR) spectrometer or a dispersive spectrometer.

3. The system of claim 1, wherein the semiconductor sources are selected from the group consisting of semiconductor lasers, super-luminescent diodes, and light emitting diodes.

4. The system of claim 1, wherein the sample comprises an organic compound with an overtone or combinational absorption band in the wavelength range between approximately 1 micron and approximately 2.5 microns.

5. The system of claim 1, wherein the sample comprises a material selected from the group consisting of a pharmaceutical, a counterfeit drug, an illicit drug, a fruit, a vegetable, a grain and a meat.

6. A measurement system comprising:
   a light source configured to generate an output optical beam, comprising:
   a plurality of semiconductor sources configured to generate an input optical beam;
   a multiplexer configured to receive at least a portion of the input optical beam and to form an intermediate optical beam; and
   one or more fibers configured to receive at least a portion of the intermediate optical beam and to form the output optical beam, wherein the output optical beam comprises one or more optical wavelengths;

a measurement apparatus configured to receive a received portion of the output optical beam and to deliver a delivered portion of the output optical beam to a sample, wherein the delivered portion of the output optical beam is configured to generate a spectroscopy output beam from the sample; and a receiver configured to receive at least a portion of the spectroscopy output beam and to process the portion of the spectroscopy output beam to generate an output signal, wherein the receiver comprises a Fourier transform infrared (FTIR) spectrometer or a dispersive spectrometer;

wherein at least a part of the delivered portion of the output optical beam is at least partially transmitting through a packaging material covering at least a part of the sample.

7. The system of claim 6, wherein the light source comprises a super-continuum laser.

8. The system of claim 6, wherein the semiconductor sources are selected from the group consisting of semiconductor lasers, super-luminescent diodes, and light emitting diodes.

9. The system of claim 6, wherein the delivered portion of the output optical beam is a spatially coherent beam and wherein the sample is remote from the light source and the receiver.

10. The system of claim 6, wherein at least a portion of the one or more optical wavelengths comprises a short-wave infrared wavelength between approximately 1400 nanometers and approximately 2500 nanometers.

11. The system of claim 6, wherein the sample comprises an organic compound with an overtone or combinational absorption band in the wavelength range between approximately 1 micron and approximately 2.5 microns.

12. The system of claim 6, wherein the spectroscopy output beam has a bandwidth of at least 10 nanometers, and wherein the output signal identifies the sample based at least in part on a chemical composition of the sample.

13. The system of claim 6, wherein the measurement apparatus is configured for a non-destructive and non-contact measurement.

14. The system of claim 6, wherein the sample comprises a material selected from the group consisting of a pharmaceutical, a counterfeit drug, an illicit drug, a fruit, a vegetable, a grain and a meat.

15. The system of claim 6, wherein the output signal is configured for on-line inspection, drug detection, quality assessment or process control.

16. A method of measuring, comprising:
generating an output optical beam, comprising:
generating an input optical beam from a plurality of semiconductor sources;
multiplexing at least a portion of the input optical beam and forming an intermediate optical beam; and
guiding at least a portion of the intermediate optical beam and forming the output optical beam, wherein the output optical beam comprises one or more optical wavelengths;

receiving a received portion of the output optical beam and delivering a delivered portion of the output optical beam to a sample, wherein the sample comprises an organic compound with an overtone or combinational absorption band in the wavelength range between approximately 1 micron and approximately 2.5 microns;

generating a spectroscopy output beam having a bandwidth of at least 10 nanometers from the sample using a Fourier transform infrared (FTIR) spectrometer or a dispersive spectrometer;

receiving at least a portion of the spectroscopy output beam; and processing the portion of the spectroscopy output beam and generating an output signal.

17. The method of claim 16, wherein the one or more optical wavelengths comprises a short-wave infrared wavelength between approximately 1400 nanometers and approximately 2500 nanometers.

18. The method of claim 16, wherein at least a part of the delivered portion of the output optical beam is at least partially transmitting through a packaging material covering at least a part of the sample.

19. The method of claim 16, wherein the output signal is configured for on-line inspection, drug detection, quality assessment or process control.

* * * * *